(12) United States Patent
Bolduc et al.

(10) Patent No.: US 9,968,353 B2
(45) Date of Patent: May 15, 2018

(54) CATHETER BASED FASTENER IMPLANTATION APPARATUS AND METHODS

(71) Applicant: Medtronic Vascular, Inc., Santa Rosa, CA (US)

(72) Inventors: Lee Bolduc, Redwood City, CA (US); Juan Parodi, Buenos Aires (AR)

(73) Assignee: Medtronic Vascular, Inc., Minneapolis, MN (US)

( * ) Notice: Subject to any disclaimer, the term of this patent is extended or adjusted under 35 U.S.C. 154(b) by 139 days.

(21) Appl. No.: 14/937,697

(22) Filed: Nov. 10, 2015

(65) Prior Publication Data
US 2016/0058438 A1  Mar. 3, 2016

Related U.S. Application Data

(60) Division of application No. 12/315,015, filed on Nov. 26, 2008, now abandoned, which is a division of
(Continued)

(51) Int. Cl.
*A61B 17/064* (2006.01)
*A61B 17/068* (2006.01)
(Continued)

(52) U.S. Cl.
CPC .......... *A61B 17/064* (2013.01); *A61B 17/068* (2013.01); *A61B 17/0644* (2013.01);
(Continued)

(58) Field of Classification Search
CPC . A61B 17/064; A61B 17/0644; A61B 17/068; A61B 2017/00398;
(Continued)

(56) References Cited

U.S. PATENT DOCUMENTS 2,033,039 A  3/1936 Limpert
3,499,222 A  3/1970 Linkow et al.
(Continued)

FOREIGN PATENT DOCUMENTS

AU  2002353807  6/2003
AU  2004277897  4/2005
(Continued)

OTHER PUBLICATIONS

5mm Origin Tracker⊥ It Runs in Circles Around Staples, 1995 Advertising Literature.
(Continued)

*Primary Examiner* — Julian W Woo

(57) ABSTRACT

Apparatus and methods utilize an intraluminal fastener applier having a guide body with a longitudinal axis. The guide body is sized and configured for intraluminal deployment in a hollow body organ. An actuated assembly is carried by the guide body that is selectively operable to generate an implantation force to implant at least one fastener into tissue within the hollow body organ. The actuated assembly includes a driven member extending generally along the longitudinal axis, which is sized and configured to engage a selected fastener. The actuated assembly also includes a drive member coupled to the driven member to impart the implantation force to the driven element in a direction that is at an angle to the longitudinal axis of the guide body.

12 Claims, 38 Drawing Sheets

Related U.S. Application Data application No. 10/669,881, filed on Sep. 24, 2003, now Pat. No. 7,491,232, which is a continuation-in-part of application No. 10/307,226, filed on Nov. 29, 2002, now Pat. No. 8,075,570, which is a continuation-in-part of application No. 10/271,334, filed on Oct. 15, 2002, now Pat. No. 6,960,217, which is a continuation-in-part of application No. 10/099,149, filed on Mar. 15, 2002, now Pat. No. 6,800,081, which is a division of application No. 09/787,135, filed on Jun. 4, 2001, now Pat. No. 6,592,593.

(51) Int. Cl.
*A61F 2/06* (2013.01)
*A61F 2/07* (2013.01)
*A61B 17/10* (2006.01)
*A61B 17/00* (2006.01)
*A61B 17/29* (2006.01)
*A61F 2/848* (2013.01)
*A61F 2/89* (2013.01)

(52) U.S. Cl.
CPC .............. *A61B 17/10* (2013.01); *A61F 2/064* (2013.01); *A61F 2/07* (2013.01); *A61B 2017/00398* (2013.01); *A61B 2017/00539* (2013.01); *A61B 2017/00544* (2013.01); *A61B 2017/00734* (2013.01); *A61B 2017/0647* (2013.01); *A61B 2017/0648* (2013.01); *A61B 2017/0649* (2013.01); *A61B 2017/2905* (2013.01); *A61F 2/848* (2013.01); *A61F 2/89* (2013.01); *A61F 2002/065* (2013.01)

(58) Field of Classification Search
CPC ........... A61B 2017/00539; A61B 2017/00544; A61B 2017/00734; A61B 2017/0647; A61B 2017/0648; A61B 2017/0649; A61B 2017/2905; A61F 2002/065; A61F 2/064; A61F 2/07; A61F 2/848; A61F 2/89

See application file for complete search history.

(56) References Cited

U.S. PATENT DOCUMENTS

| | | |
|---|---|---|
| 3,686,740 A | 8/1972 | Shiley |
| 3,799,172 A | 3/1974 | Szpur |
| 4,140,126 A | 2/1979 | Choudhury |
| 4,255,820 A | 3/1981 | Rothermel et al. |
| 4,307,722 A | 12/1981 | Evans |
| 4,580,568 A | 4/1986 | Gianturco |
| 4,586,923 A | 5/1986 | Gould et al. |
| 4,625,597 A | 12/1986 | Cast |
| 4,694,827 A | 9/1987 | Weiner et al. |
| 4,781,682 A | 11/1988 | Patel |
| 4,822,345 A | 4/1989 | Danforth |
| 4,898,577 A | 2/1990 | Badger et al. |
| 4,899,747 A | 2/1990 | Garren et al. |
| 4,921,484 A | 5/1990 | Hillstead |
| 4,990,151 A | 2/1991 | Wallsten |
| 4,994,071 A | 2/1991 | MacGregor |
| 5,030,204 A | 7/1991 | Badger et al. |
| 5,042,707 A | 8/1991 | Taheri |
| 5,044,519 A | 9/1991 | Aoyama |
| 5,071,407 A | 12/1991 | Termin et al. |
| 5,104,399 A | 4/1992 | Lazarus |
| 5,185,004 A | 2/1993 | Lashinski |
| 5,192,314 A | 3/1993 | Daskalakis |
| 5,195,968 A | 3/1993 | Lundauist et al. |
| 5,199,950 A | 4/1993 | Schmitt et al. |
| 5,207,695 A | 5/1993 | Trout, III |
| 5,282,824 A | 2/1994 | Gianturco |
| 5,290,295 A | 3/1994 | Querals et al. |
| 5,318,525 A | 6/1994 | West et al. |
| 5,320,630 A | 6/1994 | Ahmed |
| 5,330,490 A | 7/1994 | Wilk et al. |
| 5,330,503 A | 7/1994 | Yoon |
| 5,334,196 A | 8/1994 | Scott et al. |
| 5,352,197 A | 10/1994 | Hammersmark et al. |
| 5,364,351 A | 11/1994 | Heinzelman et al. |
| 5,383,880 A | 1/1995 | Hooven |
| 5,387,235 A | 2/1995 | Chuter |
| 5,409,498 A | 4/1995 | Braddock et al. |
| 5,456,713 A | 10/1995 | Chutter |
| 5,456,714 A | 10/1995 | Owen |
| 5,470,337 A | 11/1995 | Moss |
| 5,474,568 A | 12/1995 | Scott |
| 5,480,382 A | 1/1996 | Hammerslag et al. |
| 5,480,423 A | 1/1996 | Ravenscroft et al. |
| 5,489,295 A | 2/1996 | Piplani et al. |
| 5,522,881 A | 6/1996 | Lentz |
| 5,531,686 A | 7/1996 | Lundquist et al. |
| 5,534,007 A | 7/1996 | St. Germain et al. |
| 5,562,728 A | 10/1996 | Lazarus et al. |
| 5,571,171 A | 11/1996 | Barone et al. |
| 5,571,173 A | 11/1996 | Parodi |
| 5,582,616 A | 12/1996 | Bolduc et al. |
| 5,591,195 A | 1/1997 | Taheri et al. |
| 5,609,627 A | 3/1997 | Goicechea et al. |
| 5,626,613 A | 5/1997 | Schmieding |
| 5,628,788 A | 5/1997 | Pinchuk |
| 5,632,772 A | 5/1997 | Alcime et al. |
| 5,634,936 A | 6/1997 | Linden et al. |
| 5,639,278 A | 6/1997 | Dereume et al. |
| 5,662,675 A | 9/1997 | Polanskyj Stockert et al. |
| 5,662,683 A | 9/1997 | Kay |
| 5,662,700 A | 9/1997 | Lazarus |
| 5,676,696 A | 10/1997 | Marcade |
| 5,676,697 A | 10/1997 | McDonald |
| 5,683,450 A | 11/1997 | Goicechea et al. |
| 5,693,084 A | 12/1997 | Chuter |
| 5,693,086 A | 12/1997 | Goicechea et al. |
| 5,700,269 A | 12/1997 | Pinchuk et al. |
| 5,702,343 A | 12/1997 | Alferness |
| 5,702,365 A | 12/1997 | King |
| 5,702,408 A | 12/1997 | Wales et al. |
| 5,707,376 A | 1/1998 | Kavteledze et al. |
| 5,713,907 A | 2/1998 | Hogendijk et al. |
| 5,733,325 A | 3/1998 | Robinson et al. |
| 5,749,921 A | 5/1998 | Lenker et al. |
| 5,755,777 A | 5/1998 | Chuter |
| 5,762,458 A | 6/1998 | Wang et al. |
| 5,769,884 A | 6/1998 | Solovay |
| 5,776,142 A | 7/1998 | Gunderson |
| 5,779,731 A | 7/1998 | Leavitt |
| 5,782,844 A | 7/1998 | Yoon et al. |
| 5,797,933 A | 8/1998 | Snow et al. |
| 5,800,528 A | 9/1998 | Lederman et al. |
| 5,810,882 A | 9/1998 | Bolduc et al. |
| 5,814,016 A | 9/1998 | Valley et al. |
| 5,824,008 A | 10/1998 | Bolduc et al. |
| 5,824,037 A | 10/1998 | Fogarty et al. |
| 5,824,041 A | 10/1998 | Lenker et al. |
| 5,830,221 A | 11/1998 | Stein et al. |
| 5,830,229 A | 11/1998 | Kanya et al. |
| 5,843,160 A | 12/1998 | Rhodes |
| 5,855,565 A | 1/1999 | Bar-Cohen et al. |
| 5,855,598 A | 1/1999 | Pinchuk |
| 5,861,003 A | 1/1999 | Latson et al. |
| 5,865,791 A | 2/1999 | Whayne |
| 5,876,432 A | 3/1999 | Lau et al. |
| 5,904,713 A | 5/1999 | Leschinsky |
| 5,906,619 A | 5/1999 | Olson et al. |
| 5,906,641 A | 5/1999 | Thomson et al. |
| 5,916,263 A | 6/1999 | Goicechea et al. |
| 5,944,750 A | 8/1999 | Tanner et al. |
| 5,957,940 A | 9/1999 | Tanner et al. |
| 5,964,772 A | 10/1999 | Bolduc et al. |
| 5,968,053 A | 10/1999 | Revelas |
| 5,972,003 A | 10/1999 | Rousseau et al. |
| 5,972,023 A | 10/1999 | Tanner et al. |

(56) References Cited

U.S. PATENT DOCUMENTS

| | | |
|---|---|---|
| 5,980,548 A | 11/1999 | Evans et al. |
| 5,993,401 A | 11/1999 | Inbe et al. |
| 5,993,466 A | 11/1999 | Yoon |
| 5,997,556 A | 12/1999 | Tanner |
| 6,016,810 A | 1/2000 | Ravenscroft |
| 6,024,703 A | 2/2000 | Zanelli et al. |
| 6,024,763 A | 2/2000 | Lenker et al. |
| 6,027,462 A | 2/2000 | Greene et al. |
| 6,070,589 A | 6/2000 | Keith et al. |
| 6,074,418 A | 6/2000 | Buchanan et al. |
| 6,077,214 A | 6/2000 | Mortier et al. |
| 6,077,297 A | 6/2000 | Robinson et al. |
| 6,086,582 A | 7/2000 | Altman et al. |
| 6,090,137 A | 7/2000 | Schmitt |
| 6,123,722 A | 9/2000 | Fogarty et al. |
| 6,126,685 A | 10/2000 | Lenker et al. |
| 6,145,509 A | 11/2000 | Tanner |
| 6,146,339 A | 11/2000 | Biagtan et al. |
| 6,152,144 A | 11/2000 | Lesh et al. |
| 6,162,168 A | 12/2000 | Schweich et al. |
| 6,168,610 B1 | 1/2001 | Marin et al. |
| 6,174,323 B1 | 1/2001 | Biggs et al. |
| 6,179,809 B1 | 1/2001 | Khairkhahan et al. |
| 6,197,049 B1 | 3/2001 | Shaolian et al. |
| 6,203,550 B1 | 3/2001 | Olson |
| 6,203,568 B1 | 3/2001 | Lombardi et al. |
| 6,206,827 B1 | 3/2001 | Chin et al. |
| 6,217,597 B1 | 4/2001 | Tanner |
| 6,224,540 B1 | 5/2001 | Lederman et al. |
| 6,231,561 B1 | 5/2001 | Frazier et al. |
| 6,248,118 B1 | 6/2001 | Tanner et al. |
| 6,250,974 B1 | 6/2001 | Kerek |
| 6,258,021 B1 | 7/2001 | Wilk |
| 6,258,119 B1 | 7/2001 | Hussein et al. |
| 6,270,516 B1 | 8/2001 | Tanner et al. |
| 6,273,858 B1 | 8/2001 | Fox et al. |
| 6,286,514 B1 | 9/2001 | Lemelson |
| 6,287,315 B1 | 9/2001 | Wijeratne et al. |
| 6,287,335 B1 | 9/2001 | Drasler et al. |
| 6,293,906 B1 | 9/2001 | Vanden Hoek et al. |
| 6,296,656 B1 | 10/2001 | Bolduc et al. |
| 6,302,906 B1 | 10/2001 | Goicoechea et al. |
| 6,309,403 B1 | 10/2001 | Minor et al. |
| 6,319,278 B1 | 11/2001 | Quinn |
| 6,336,933 B1 | 1/2002 | Parodi |
| 6,343,605 B1 | 2/2002 | Lafontaine |
| 6,346,118 B1 | 2/2002 | Baker et al. |
| 6,352,561 B1 | 3/2002 | Leopold et al. |
| 6,371,919 B1 | 4/2002 | Tanner et al. |
| 6,398,803 B1 | 6/2002 | Layne et al. |
| 6,402,680 B2 | 6/2002 | Mortier et al. |
| 6,402,780 B2 | 6/2002 | Williamson et al. |
| 6,406,420 B1 | 6/2002 | McCarthy et al. |
| 6,409,757 B1 | 6/2002 | Trout, III et al. |
| 6,416,365 B1 | 7/2002 | Iwahori |
| 6,416,522 B1 | 7/2002 | Strecker |
| 6,423,059 B1 | 7/2002 | Hanson et al. |
| 6,425,856 B1 | 7/2002 | Shapland et al. |
| 6,428,565 B1 | 8/2002 | Wisselink |
| 6,454,796 B1 | 9/2002 | Barkman et al. |
| 6,458,152 B1 | 10/2002 | Khosravi et al. |
| 6,461,365 B2 | 10/2002 | Bolduc et al. |
| 6,468,260 B1 | 10/2002 | Bumbalough et al. |
| 6,482,224 B1 | 11/2002 | Michler et al. |
| 6,520,974 B2 | 2/2003 | Tanner et al. |
| 6,544,253 B1 | 4/2003 | Tanner |
| 6,558,425 B2 | 5/2003 | Rockwood, Jr. |
| 6,562,051 B1 | 5/2003 | Bolduc et al. |
| 6,565,597 B1 | 5/2003 | Fearnot et al. |
| 6,576,009 B2 | 6/2003 | Ryan et al. |
| 6,580,417 B2 | 6/2003 | Rosenbera et al. |
| 6,592,593 B1 | 7/2003 | Parodi et al. |
| 6,592,615 B1 | 7/2003 | Marcade et al. |
| 6,595,912 B2 | 7/2003 | Lau et al. |
| 6,607,555 B2 | 8/2003 | Patterson et al. |
| 6,616,684 B1 | 9/2003 | Vidlund et al. |
| 6,639,278 B2 | 10/2003 | Sumida et al. |
| 6,652,555 B1 | 11/2003 | Vantassel et al. |
| 6,652,572 B2 | 11/2003 | Kugler et al. |
| 6,663,558 B2 | 12/2003 | Lau et al. |
| 6,675,809 B2 | 1/2004 | Stack et al. |
| 6,685,620 B2 | 2/2004 | Gifford, III et al. |
| 6,702,763 B2 | 3/2004 | Murphy et al. |
| 6,702,844 B1 | 3/2004 | Lazarus |
| 6,709,442 B2 | 3/2004 | Miller et al. |
| 6,719,174 B1 | 4/2004 | Swift |
| 6,730,119 B1 | 5/2004 | Smalling |
| 6,746,460 B2 | 6/2004 | Gannoe et al. |
| 6,800,081 B2 | 10/2004 | Parodi |
| 6,878,164 B2 | 4/2005 | Kujawski et al. |
| 6,929,661 B2 | 8/2005 | Bolduc et al. |
| 6,960,217 B2 | 11/2005 | Bolduc |
| 6,984,241 B2 | 1/2006 | Lubbers et al. |
| 6,986,775 B2 | 1/2006 | Morales et al. |
| 6,986,784 B1 | 1/2006 | Weiser et al. |
| 7,033,384 B2 | 4/2006 | Gannoe et al. |
| 7,037,343 B2 | 5/2006 | Imran |
| 7,060,021 B1 | 6/2006 | Wilk |
| 7,060,023 B2 | 6/2006 | French et al. |
| 7,081,086 B2 | 7/2006 | Lau et al. |
| 7,081,129 B2 | 7/2006 | Chobotoy |
| 7,128,754 B2 | 10/2006 | Bolduc |
| 7,147,657 B2 | 12/2006 | Chiang et al. |
| 7,155,295 B2 | 12/2006 | Lau et al. |
| 7,179,225 B2 | 2/2007 | Shluzas et al. |
| 7,306,623 B2 | 12/2007 | Watson |
| 7,335,213 B1 | 2/2008 | Hyde et al. |
| 7,361,137 B2 | 4/2008 | Taylor et al. |
| 7,404,824 B1 | 7/2008 | Webler et al. |
| 7,422,558 B2 | 9/2008 | Lau et al. |
| 7,491,232 B2 | 2/2009 | Bolduc et al. |
| 7,544,198 B2 | 6/2009 | Parodi |
| 7,563,267 B2 | 7/2009 | Goldfarb et al. |
| 7,591,842 B2 | 9/2009 | Parodi |
| 7,637,932 B2 | 12/2009 | Bolduc et al. |
| 7,704,269 B2 | 4/2010 | St. Goar et al. |
| 7,727,189 B2 | 6/2010 | Vantassel et al. |
| 7,753,922 B2 | 7/2010 | Starksen |
| 7,811,295 B2 | 10/2010 | Kortenbach |
| 7,823,267 B2 | 11/2010 | Bolduc |
| 7,828,267 B2 | 11/2010 | Iwabuchi et al. |
| 7,828,838 B2 | 11/2010 | Bolduc et al. |
| 7,959,663 B2 | 6/2011 | Bolduc |
| 7,959,670 B2 | 6/2011 | Bolduc |
| 8,075,570 B2 | 12/2011 | Bolduc et al. |
| 8,080,050 B2 | 12/2011 | Chiang et al. |
| 8,083,752 B2 | 12/2011 | Bolduc |
| 8,092,519 B2 | 1/2012 | Bolduc |
| 8,231,639 B2 | 7/2012 | Bolduc et al. |
| 8,685,044 B2 | 4/2014 | Bolduc et al. |
| 8,690,897 B2 | 4/2014 | Bolduc |
| 2001/0041821 A1 | 11/2001 | Wilk |
| 2002/0026144 A1 | 2/2002 | Patterson |
| 2002/0029077 A1 | 3/2002 | Leopold et al. |
| 2002/0058855 A1 | 5/2002 | Cyril, Jr. et al. |
| 2002/0065485 A1 | 5/2002 | DuBois et al. |
| 2002/0087169 A1 | 7/2002 | Brock et al. |
| 2002/0099432 A1 | 7/2002 | Yee |
| 2002/0133054 A1 | 9/2002 | Murphy et al. |
| 2002/0156365 A1 | 10/2002 | Tsekos |
| 2002/0156521 A1 | 10/2002 | Ryan et al. |
| 2002/0183827 A1 | 12/2002 | Derus et al. |
| 2003/0018358 A1 | 1/2003 | Saadat |
| 2003/0060674 A1 | 3/2003 | Hanson, III et al. |
| 2003/0078465 A1 | 4/2003 | Pai et al. |
| 2003/0100943 A1 | 5/2003 | Bolduc |
| 2003/0105384 A1 | 6/2003 | Sharkey et al. |
| 2003/0105519 A1 | 6/2003 | Fasol et al. |
| 2003/0130731 A1 | 7/2003 | Vidlund et al. |
| 2003/0149463 A1 | 8/2003 | Solymar et al. |
| 2003/0158570 A1 | 8/2003 | Ferrazzi |
| 2003/0163085 A1 | 8/2003 | Tanner et al. |
| 2003/0233140 A1 | 12/2003 | Hartley et al. |
| 2004/0002731 A1 | 1/2004 | Aqanon et al. |

(56) References Cited

U.S. PATENT DOCUMENTS

| | | |
|---|---|---|
| 2004/0039405 A1 | 2/2004 | Petrovic et al. |
| 2004/0044364 A1 | 3/2004 | Devries et al. |
| 2004/0049207 A1 | 3/2004 | Goldfarb et al. |
| 2004/0054352 A1 | 3/2004 | Adams et al. |
| 2004/0093057 A1 | 5/2004 | Bolduc et al. |
| 2004/0127916 A1 | 7/2004 | Bolduc et al. |
| 2004/0138734 A1 | 7/2004 | Chobotov et al. |
| 2004/0153143 A1 | 8/2004 | Quiachon et al. |
| 2004/0186566 A1 | 9/2004 | Hindrichs et al. |
| 2004/0206363 A1 | 10/2004 | Mccarthy et al. |
| 2004/0210304 A1 | 10/2004 | Seguin et al. |
| 2004/0243170 A1 | 12/2004 | Suresh et al. |
| 2004/0254594 A1 | 12/2004 | Alfaro |
| 2004/0260322 A1 | 12/2004 | Rudko et al. |
| 2004/0260383 A1 | 12/2004 | Stelter et al. |
| 2005/0038506 A1 | 2/2005 | Webler et al. |
| 2005/0043790 A1 | 2/2005 | Seguin |
| 2005/0070992 A1 | 3/2005 | Bolduc et al. |
| 2005/0113906 A9 | 5/2005 | Bolduc et al. |
| 2005/0154401 A1 | 7/2005 | Weldon et al. |
| 2005/0177180 A1 | 8/2005 | Kaganov et al. |
| 2005/0187613 A1 | 8/2005 | Bolduc |
| 2005/0197716 A1 | 9/2005 | Sharkey et al. |
| 2005/0215874 A1 | 9/2005 | Wang et al. |
| 2005/0240258 A1 | 10/2005 | Bolduc et al. |
| 2005/0240260 A1 | 10/2005 | Bolduc |
| 2006/0100640 A1 | 5/2006 | Bolduc et al. |
| 2006/0184224 A1 | 8/2006 | Angel |
| 2006/0253186 A1 | 11/2006 | Bates |
| 2006/0259125 A1 | 11/2006 | Peacock |
| 2006/0287661 A1 | 12/2006 | Bolduc et al. |
| 2007/0021753 A1 | 1/2007 | Bolduc et al. |
| 2007/0021829 A1 | 1/2007 | Bolduc et al. |
| 2007/0032860 A1 | 2/2007 | Brooks et al. |
| 2007/0073389 A1 | 3/2007 | Bolduc et al. |
| 2007/0083255 A1 | 4/2007 | Chiang et al. |
| 2008/0065115 A1 | 3/2008 | Parodi |
| 2008/0065117 A1 | 3/2008 | Bolduc et al. |
| 2008/0065189 A1 | 3/2008 | Bolduc |
| 2008/0097489 A1 | 4/2008 | Goldfarb et al. |
| 2008/0132996 A1 | 6/2008 | Drasler et al. |
| 2009/0099650 A1 | 4/2009 | Bolduc et al. |
| 2009/0112302 A1 | 4/2009 | Stafford |
| 2009/0112303 A1 | 4/2009 | Bolduc |
| 2009/0138072 A1 | 5/2009 | Gendreau |
| 2010/0094400 A1 | 4/2010 | Bolduc et al. |
| 2011/0087320 A1 | 4/2011 | Bolduc et al. |
| 2011/0238088 A1 | 9/2011 | Bolduc et al. |
| 2011/0276062 A1 | 11/2011 | Bolduc |
| 2012/0065661 A1 | 3/2012 | Bolduc |
| 2012/0316578 A1 | 12/2012 | Bolduc et al. |
| 2014/0194902 A1 | 7/2014 | Bolduc et al. |
| 2014/0214051 A1 | 7/2014 | Bolduc |

FOREIGN PATENT DOCUMENTS

| | | |
|---|---|---|
| AU | 2008243229 | 12/2008 |
| AU | 2011253682 | 12/2011 |
| AU | 2006305688 | 12/2012 |
| AU | 2011224089 | 7/2014 |
| CA | 2265131 | 9/1999 |
| CA | 2344252 | 3/2000 |
| CA | 2729464 | 6/2003 |
| CA | 2539265 | 5/2005 |
| CA | 2625082 | 4/2007 |
| CA | 2626505 | 4/2007 |
| CA | 2626106 | 5/2007 |
| CA | 2740831 | 4/2010 |
| CA | 2464048 | 6/2010 |
| CA | 2464900 | 4/2011 |
| CA | 2554022 | 11/2012 |
| CN | 1019461 | 12/1992 |
| CN | 1422139 | 6/2003 |
| CN | 1596087 | 3/2005 |
| CN | 1596088 | 3/2005 |
| CN | 1856280 | 11/2006 |
| CN | 1870949 | 11/2006 |
| CN | 1997318 | 7/2007 |
| CN | 101267788 | 9/2008 |
| CN | 101330882 | 12/2008 |
| CN | 101352375 | 1/2009 |
| CN | 201360466 | 2/2009 |
| CN | 101460104 | 6/2009 |
| CN | 101466316 | 6/2009 |
| CN | 100525719 | 8/2009 |
| CN | 101330882 | 4/2011 |
| CN | 101466316 | 6/2012 |
| DE | 3333427 | 5/1991 |
| DE | 69228184 | 9/1999 |
| DE | 10034105 | 4/2002 |
| DE | 10297483 | 12/2004 |
| EP | 0321912 | 12/1987 |
| EP | 0663184 | 1/1994 |
| EP | 0835642 | 8/2002 |
| EP | 1369098 | 12/2003 |
| EP | 1440673 | 7/2004 |
| EP | 1448117 | 8/2004 |
| EP | 1675528 | 7/2006 |
| EP | 1725172 | 11/2006 |
| EP | 1734872 | 12/2006 |
| EP | 1948080 | 7/2008 |
| EP | 2349086 | 8/2011 |
| FR | 2299548 | 1/1975 |
| FR | 2865926 | 8/2005 |
| GB | 2396824 | 7/2004 |
| GB | 2417208 | 2/2006 |
| HK | 1073240 | 8/2009 |
| JP | 2001509398 | 7/2001 |
| JP | 2001522292 | 11/2001 |
| JP | 2001526574 | 12/2001 |
| JP | 2002526193 | 8/2002 |
| JP | 2005046648 | 2/2005 |
| JP | 2005510293 | 4/2005 |
| JP | 2005510303 | 4/2005 |
| JP | 2007508894 | 4/2007 |
| JP | 2007535339 | 12/2007 |
| JP | 2009512497 | 3/2009 |
| JP | 2009512498 | 3/2009 |
| JP | 2009512499 | 3/2009 |
| JP | 2009078172 | 4/2009 |
| JP | 2009106768 | 5/2009 |
| JP | 2009106775 | 5/2009 |
| JP | 2009112827 | 5/2009 |
| JP | 2009519046 | 5/2009 |
| JP | 4405262 | 1/2010 |
| JP | 10506026 | 2/2010 |
| JP | 2010051786 | 3/2010 |
| JP | 4465359 | 5/2010 |
| JP | 2011062570 | 3/2011 |
| JP | 4699445 | 6/2011 |
| WO | WO9300868 | 1/1993 |
| WO | WO9521592 | 8/1995 |
| WO | WO9603925 | 2/1996 |
| WO | WO97/03616 | 2/1997 |
| WO | WO9712562 | 4/1997 |
| WO | WO9717039 | 5/1997 |
| WO | WO9717913 | 5/1997 |
| WO | WO9811814 | 3/1998 |
| WO | WO9853761 | 12/1998 |
| WO | WO9933402 | 7/1999 |
| WO | WO9933402 | 9/1999 |
| WO | WO99/53845 | 10/1999 |
| WO | WO00/16701 | 3/2000 |
| WO | WO0035350 | 6/2000 |
| WO | WO0064357 | 11/2000 |
| WO | WO0160432 | 8/2001 |
| WO | WO03032870 | 4/2003 |
| WO | WO03045283 | 6/2003 |
| WO | WO03045467 | 6/2003 |
| WO | WO03079935 | 10/2003 |
| WO | WO2004008975 | 1/2004 |
| WO | WO2004021872 | 3/2004 |
| WO | WO200503707 | 4/2005 |
| WO | WO2005032333 | 4/2005 |

(56) References Cited

FOREIGN PATENT DOCUMENTS

| WO | WO2005044073 | 5/2005 |
|---|---|---|
| WO | WO2005044147 | 5/2005 |
| WO | WO2005044148 | 5/2005 |
| WO | WO2005067660 | 7/2005 |
| WO | WO2005081936 | 9/2005 |
| WO | WO2005102181 | 11/2005 |
| WO | WO2005067660 | 4/2007 |
| WO | WO2007046953 | 4/2007 |
| WO | WO2007046954 | 4/2007 |
| WO | WO2007046955 | 4/2007 |
| WO | WO2007047023 | 4/2007 |
| WO | WO2007053233 | 5/2007 |
| WO | WO2007053233 | 1/2008 |
| WO | WO2010004856 | 1/2010 |
| WO | WO2010044851 | 4/2010 |
| WO | WO2010044854 | 4/2010 |
| WO | WO2010044855 | 4/2010 |
| WO | WO2010044856 | 4/2010 |

OTHER PUBLICATIONS

"The Spiral Tracker: A New Technique for Stabilizing Prosthetic Mesh in Laparoscopic Hernia Repair" Nov. 1995 Surgical Rounds.
"Laparoscopic Surgery", MedPro Month Oct. 1995, p. 190.
"Assisted TAPP Procedure" Newman III et al., Circa 1995.
"Extraperitoneal Endoscopic Burch Repair Using a Tacker Mesh Technique" Hatchett et al. Circa 1999.
U.S. Appl. No. 12/288,031, Non Final Office Action dated Feb. 17, 2015, 17pgs.
U.S. Appl. No. 12/288,034, Final Office Action dated Dec. 1, 2014, 8pgs.
U.S. Appl. No. 13/257,242, Notice of Allowance dated Jan. 14, 2015, 8pgs.
U.S. Appl. No. 13/162,384, Non-Final Office Action dated Feb. 24, 2015, 14 pgs.
U.S. Appl. No. 14/595,928, Preliminary Amendment filed Jan. 14, 2015, 9pgs.
European Application Serial No. 04788653.6, European Search Report, dated Aug. 6, 2014, 3pgs.
European Application Serial No. 04788653.6, Response filed Oct. 21, 2014 to European Search Report dated Aug. 6, 2014, 4pgs.
U.S. Appl. No. 12/288,031, Response filed Nov. 15, 2013 to Non Final Office Action dated Jul. 15, 2013, 11pgs.
U.S. Appl. No. 12/288,034, Final Office Action dated Nov. 4, 2013, 8pgs.
U.S. Appl. No. 12/917,842, Notice of Allowance dated Dec. 2, 2013, 7pgs.
U.S. Appl. No. 12/942,232 Non Final Office Action dated Oct. 9, 2013, 13pgs.
U.S. Appl. No. 13/157,242 Non Final Office Action dated Oct. 31, 2013, 6pgs.
U.S. Appl. No. 13/162,384 Advisory Action dated Nov. 15, 2013, 3pgs.
U.S. Appl. No. 13/162,384, Response filed Oct. 18, 2013 to Final Office Action dated Aug. 27, 2013, 5pgs.
U.S. Appl. No. 13/495,836, Notice of Allowance dated Dec. 4, 2013, 9pgs.
U.S. Appl. No. 13/495,836, Response filed Nov. 5, 2013 to Non Final Office Action dated Aug. 5, 2013, 8pgs.
European Application Serial No. 06802580.8, Extended European Search Report dated Sep. 24, 2013, 8pgs.
Response to Non Final Office Action dated Nov. 22, 2004, for U.S. Appl. No. 10/271,334, filed on Oct. 15, 2002, 10pages.
Supplemental Response to Non-Final Office Action dated Jan. 28, 2005 for U.S. Appl. No. 10/271,334, filed on Oct. 15, 2002, 10pages.
U.S. Appl. No. 12/942,232, Response filed Jan. 9, 2014 to Non Final Office Action dated Oct. 9, 2013, 11pgs.
U.S. Appl. No. 13/157,242, Notice of Allowance dated Feb. 26, 2014, 8pgs.
U.S. Appl. No. 13/157,242 Notice of Allowance dated May 9, 2014 8pgs.
U.S. Appl. No. 13/157,242 Response filed Jan. 28, 2014 to Non Final Office Action dated Oct. 31, 2013 11 pgs.
U.S. Appl. No. 14/210,683 Preliminary Amendment dated Mar. 24, 2014 7 pgs.
Australian Application Serial No. 2011224089 Response filed Mar. 21, 2014 to First Examiners Report dated Mar. 27, 2013 74pgs.
Canadian Application Serial No. 2626403 Response filed Feb. 12, 2014 to Office Action dated Apr. 2, 2013, 20pgs.
European Application Serial No. 05713941.2 European Search Report dated Apr. 10, 2014, 6pgs.
U.S. Appl. No. 11/254,619 Non Final Office Action dated Jan. 6, 2014 19pgs.
U.S. Appl. No. 11/254,619 Response filed May 16, 2014 to Non Final Office Action dated Jan. 6, 2014 10pgs.
U.S. Appl. No. 11/488,305 Non Final Office Action dated Jan. 29, 2014 10pgs.
U.S. Appl. No. 11/488,305 Response filed Apr. 29, 2014 to Non Final Office Action dated Jan. 29, 2014 9pgs.
U.S. Appl. No. 12/288,031 Final Office Action dated Mar. 12, 2014 14pgs.
U.S. Appl. No. 12/288,031 Non Final Office Action May 10, 2012 7pgs.
U.S. Appl. No. 12/288,031 Response filed Jun. 5, 2014 to Final Office Action dated Mar. 12, 2014 15pgs.
U.S. Appl. No. 12/288,034 Advisory Action dated Feb. 25, 2014 3pgs.
U.S. Appl. No. 12/288,034 Non Final Office Action dated May 8, 2014 8pgs.
U.S. Appl. No. 12/288,034 Response filed Feb. 4, 2014 to Final Office Action dated Nov. 4, 2013 12 pgs.
U.S. Appl. No. 12/942,232 Final Office Action dated May 22, 2014 17pgs.
U.S. Appl. No. 12/288,034 Response filed Aug. 1, 2014 to Non Final Office Action dated May 8, 2014, 11pgs.
U.S. Appl. No. 12/942,232, Advisory Action dated Aug. 7, 2014, 3pgs.
U.S. Appl. No. 12/942,232 Response filed Jul. 21, 2014 to Final Office Action dated May 22, 2014 11pgs.
U.S. Appl. No. 13/157,242 Notice of Allowance dated Aug. 21, 2014 8pgs.
U.S. Appl. No. 13/162,384 Examiner Interview Summary dated Oct. 22, 2014 3pgs.
U.S. Appl. No. 13/162,384 Non Final Office Action dated Jul. 21, 2014 15pgs.
U.S. Appl. No. 13/162,384 Response filed Oct. 20, 2014 to Non Final Office Action dated Jul. 21, 2014 12pgs.
European Application Serial No. 05713941.2 Examination Notification Art 94(3) dated Jun. 5, 2014 7pgs.
European Application Serial No. 05723408.0 Examination Notification Art 94(3) dated Jul. 10, 2014 6pgs.
European Application Serial No. 06802580.8 Response filed Apr. 17, 2014 to Extended European Search Report dated Sep. 24, 2013 2pgs.
U.S. Appl. No. 11/254,619, Advisory Action dated Sep. 24, 2014 3pgs.
U.S. Appl. No. 11/254,619, Examiner Interview Summary dated Sep. 18, 2014 3pgs.
U.S. Appl. No. 11/254,619, Final Office Action dated Jun. 19, 2014 17pgs.
U.S. Appl. No. 11/254,619, Final Office Action dated Jun. 30, 2010, 10pgs.
U.S. Appl. No. 11/254,619, Final Office Action dated Oct. 20, 2011, 11pgs.
U.S. Appl. No. 11/254,619, Non Final Office Action dated Feb. 3, 2011, 8pgs.
U.S. Appl. No. 11/254,619, Non Final Office Action dated Oct. 1, 2009, 5pgs.
U.S. Appl. No. 11/254,619, Response filed Sep. 15, 2014 to Final Office Action dated Jun. 19, 2014 12pgs.
U.S. Appl. No. 11/488,305, Final Office Action dated Aug. 14, 2014, 11pgs.

(56) References Cited

OTHER PUBLICATIONS

U.S. Appl. No. 12/288,031, Advisory Action dated Jul. 7, 2014, 4pgs.
U.S. Appl. No. 12/288,031, Response filed Sep. 10, 2014 to Advisory Action dated Jul. 7, 2014, 16pgs.
Non Final Office Action dated May 18, 2004, for U.S. Appl. No. 10/271,334, filed on Oct. 15, 2002, 8 pages.
Examiner's Interview Summary dated Feb. 11, 2005, for U.S. Appl. No. 10/271,334, filed on Oct. 15, 2002, 1 page.
Notice of Allowability dated Feb. 11, 2005, for U.S. Appl. No. 10/271,334, filed on Oct. 15, 2002, 4 pages.
Notice of Allowance dated Mar. 17, 2005, for U.S. Appl. No. 10/271,334, filed on Oct. 15, 2002, 3 pages.
Notice of Allowance dated Aug. 26, 2005, for U.S. Appl. No. 10/271,334, filed on Oct. 15, 2002, 3 pages.
Non Final Office Action dated May 5, 2009, for U.S. Appl. No. 11/166,411, filed on Jun. 24, 2005, 7 pages.
Final Office Action dated Dec. 3, 2009, for U.S. Appl. No. 11/166,411, filed on Jun. 24, 2005, 5 pages.
Notice of Allowance dated Jan. 6, 2011, for U.S. Appl. No. 11/166,411, filed on Jun. 24, 2005, 4 pages.
Notice of Allowance dated Aug. 23, 2011, for U.S. Appl. No. 11/166,411, filed on Jun. 24, 2005, 5 pages.
Non-Final Office Action dated Oct. 6, 2008, for U.S. Appl. No. 11/540,427, filed on Sep. 29, 2006, 9 pages.
Final Office Action dated Jul. 21, 2009, for U.S. Appl. No. 11/540,427, filed on Sep. 29, 2006, 8 pages.
Notice of Allowance dated Apr. 29, 2011, for U.S. Appl. No. 11/540,427, filed on Sep. 29, 2006, 8 pages.
Non-Final Office Action dated Nov. 12, 2010, for U.S. Appl. No. 11/540,428, filed on Sep. 29, 2006, 7 pages.
Final Office Action dated Aug. 4, 2011, for U.S. Appl. No. 11/540,428, filed on Sep. 29, 2006, 9 pages.
Non-Final Office Action dated May 20, 2010, for U.S. Appl. 11/978,752, filed Oct. 30, 2007, 5 pages.
Final Office Action dated Dec. 22, 2010, for U.S. Appl. 11/978,752, filed Oct. 30, 2007, 6 pages.
Notice of Allowance dated Aug. 31, 2011, for U.S. Appl. 11/978,752, filed Oct. 30, 2007, 5 pages.
Non-Final Office Action dated Sep. 3, 2010, for U.S. Appl. 11/978,753, filed Oct. 30, 2007, 7 pages.
Final Office Action dated May 2, 2011, for U.S. Appl. 11/978,753, filed Oct. 30, 2007, 8 pages.
Non-Final Office Action dated Mar. 13, 2006, for U.S. Appl. No. 10/307,226, filed on Nov. 29, 2002, 6 pages.
Final Office Action dated Dec. 12, 2006, for U.S. Appl. No. 10/307,226, filed on Nov. 29, 2002, 5 pages.
Non-Final Office Action dated Jun. 12, 2007, for U.S. Appl. No. 10/307,226, filed on Nov. 29, 2002, 5 pages.
Final Office Action dated Jun. 27, 2008, for U.S. Appl. No. 10/307,226, filed on Nov. 29, 2002, 5 pages.
Non-Final Office Action dated Sep. 9, 2009, for U.S. Appl. No. 10/307,226, filed on Nov. 29, 2002, 6 pages.
Non-Final Office Action dated Jan. 27, 2006, for U.S. Appl. 10/669,881, filed Sep. 24, 2003, 5 pages.
Final Office Action dated Jan. 25, 2008, for U.S. Appl. 10/669,881, filed Sep. 24, 2003, 7 pages.
Notice of Allowance dated Oct. 8, 2008, for U.S. Appl. 10/669,881, filed Sep. 24, 2003, 6 pages.
Notice of Allowance dated Mar. 9, 2010, for U.S. Appl. No. 11/254,444, filed Oct. 20, 2005, 6 pages.
Notice of Allowance dated Jun. 29, 2010, for U.S. Appl. No. 11/254,444, filed Oct. 20, 2005, 6 pages.
Non-Final Office Action dated Oct. 1, 2009, for U.S. Appl. 11/254,619, filed Oct. 20, 2005, 5 pages.
Final Office Action dated Jun. 30, 2010, for U.S. Appl. 11/254,619, filed Oct. 20, 2005, 10 pages.
Non-Final Office Action dated Feb. 3, 2011, for U.S. Appl. No. 11/254,619, filed Oct. 20, 2005, 8 pages.
Final Office Action dated Oct. 20, 2011, for U.S. Appl. No. 11/254,619, filed Oct. 20, 2005, 11 pages.
Non-Final Office Action dated Mar. 30, 2009, for U.S. Appl. No. 11/254,950, filed on Oct. 20, 2005, 5 pages.
Notice of Allowance dated Feb. 26, 2010, for U.S. Appl. No. 11/254,950, filed on Oct. 20, 2005, 4 pages.
Notice of Allowance dated Jun. 22, 2010 for U.S. Appl. No. 11/254,950 filed on Oct. 20, 2005, 4 pages.
Non-Final Office Action dated May 14, 2008, for U.S. Appl. No. 11/255,116, filed Oct. 20, 2005, 14 pages.
Notice of Allowance dated Aug. 10, 2009, for U.S. Appl. No. 11/255,116 filed Oct. 20, 2005, 4 pages.
Non-Final Office Action dated Jul. 23, 2007, for U.S. Appl. No. 10/786,465, filed on Feb. 25, 2004, 6 pages.
Final Office Action dated Jan. 21, 2009, for U.S. Appl. No. 10/786,465, filed on Feb. 25, 2004, 7 pages.
Non-Final Office Action dated Mar. 26, 2010, for U.S. Appl. No. 10/786,465, filed on Feb. 25, 2004, 7 pages.
Notice of Allowance dated Mar. 14, 2012, for U.S. Appl. No. 10/786,465, filed on Feb. 25, 2004, 10 pages.
Non-Final Office Action dated Sep. 1, 2010, for U.S. Appl. No. 11/488,305, filed Jul. 18, 2006, 7 pages.
Final Office Action dated Apr. 13, 2011, for U.S. Appl. No. 11/488,305, filed Jul. 18, 2006, 8 pages.
Non-Final Office Action dated Oct. 31, 2011, for U.S. Appl. No. 11/488,305, filed on Jul. 18, 2006, 6 pages.
International Search Report dated Mar. 6, 2003, for PCT Patent Application No. PCT/US02/32753, filed on Oct. 15, 2002, one page.
Written Opinion dated Aug. 26, 2003, for PCT Patent Application No. PCT/US02/32753, filed on Oct. 15, 2002, 4 pages.
International Preliminary Report on Patentability dated Sep. 1, 2004, for PCT Patent Application No. PCT/US02/32753, filed on Oct. 15, 2002, 3 pages.
International Search Report dated May 8, 2003, for PCT Patent Application No. PCT/US02/38365, filed on Nov. 29, 2002, 4 pages.
Written Opinion dated Oct. 27, 2003, for PCT Patent Application No. PCT/US02/38365, filed on Nov. 29, 2002, 4 pages.
International Preliminary Report on Patentability dated Mar. 1, 2004, for PCT Patent Application No. PCT/US02/38365, filed on Nov. 29, 2002, 3 p pages.
International Search Report dated Feb. 24, 2006, for PCT Patent Application No. PCT/US2004/029402, filed on Sep. 10, 2004, 3 pages.
Written Opinion dated Feb. 24, 2006, for PCT Patent Application No. PCT/US2004/029402, filed on Sep. 10, 2004, 3 pages.
International Preliminary Report on Patentability dated Jul. 10, 2006, for PCT Patent Application No. PCT/US2004/029402, filed on Sep. 10, 2004, 3 pages.
International Search Report dated Mar. 30, 2007, for PCT Patent Application No. PCT/US2006/033741, filed on Aug. 29, 2006, 2 pages.
Written Opinion dated Mar. 30, 2007, for PCT Patent Application No. PCT/US2006/033741, filed on Aug. 29, 2006, 4 pages.
International Preliminary Examination Report dated Jul. 28, 2007, for PCT Patent Application No. PCT/US2006/033741, filed on Aug. 29, 2006, 5 pages.
International Search Report dated Aug. 15, 2007, for PCT Patent Application No. PCT/US2006/033748, filed on Aug. 29, 2006, 3 pages.
Written Opinion dated Aug. 15, 2007, for PCT Patent Application No. PCT/US2006/033748, filed on Aug. 29, 2006, 5 pages.
International Preliminary Report on Patentability dated Jun. 18, 2008, for PCT Patent Application No. PCT/US2006/033748, filed on Aug. 29, 2006, 7 pages.
International Search Report dated Aug. 15, 2007, for PCT Patent Application No. PCT/US06/033749, filed on Aug. 29, 2006, 3 pages.
Written Opinion dated Aug. 15, 2007, for PCT Patent Application No. PCT/US06/033749, filed on Aug. 29, 2006, 5 pages.
International Preliminary Report on Patentability dated Jun. 18, 2008, for PCT Patent Application No. PCT/US06/033749, filed on Aug. 29, 2006, 6 pages.

(56) References Cited

OTHER PUBLICATIONS

International Search Report dated Jul. 8, 2008, for PCT Patent Application No. PCT/US2006/033747, filed on Aug. 29, 2006, 2 pages.
Written Opinion dated Jul. 8, 2008, for PCT Patent Application No. PCT/US2006/033747, filed on Aug. 29, 2006, 3 pages.
International Search Report dated Sep. 25, 2007, PCT Patent Application No. PCT/US05/005627, filed Feb. 22, 2005, 3 pages.
Written Opinion dated Sep. 25, 2007, PCT Patent Application No. PCT/US05/005627, filed Feb. 22, 2005, 3 pages.
International Preliminary Examination Report dated Apr. 7, 2009, PCT Patent Application No. PCT/US05/005627, filed Feb. 22, 2005, 5 pages.
International Search Report dated Aug. 30, 2007, for PCT/US2006/037085, filed on Sep. 22, 2006, one pages.
Written Opinion dated Aug. 30, 2007, for PCT/US2006/037085, filed on Sep. 22, 2006, 7 pages.
International Preliminary Report on Patentability dated Jul. 24, 2008, for PCT/US2006/037085, filed on Sep. 22, 2006, 9 pages.
International Search Report dated Dec. 11, 2009, for PCT/US2009/005604, filed on Oct. 14, 2009, 3 pages.
Written Opinion dated Dec. 11, 2009, for PCT/US2009/005604, filed on Oct. 14, 2009, 7 pages.
International Search Report dated Dec. 18, 2009, for PCT/US2009/005609, filed Oct. 14, 2009, 3 pages.
Written Opinion dated Dec. 18, 2009, for PCT/US2009/005609, filed Oct. 14, 2009, 6 pages.
U.S. Appl. No. 13/162,384, filed Jun. 16, 2011 by Bolduc.
"U.S. Appl. No. 10/099,149, Non Final Office Action dated Sep. 10, 2003", 6 pgs.
"U.S. Appl. No. 10/099,149, Notice of Allowance dated Jun. 24, 2004", 4 pgs.
"U.S. Appl. No. 10/099,149, Response filed Mar. 12, 2004 to Non Final Office Action dated Sep. 10, 2003", 5 pgs.
"U.S. Appl. No. 10/271,334, Non Final Office Action dated May 18, 2004", 9 pgs.
"U.S. Appl. No. 10/271,334, Notice of Allowance dated Feb. 11, 2005", 6 pgs.
"U.S. Appl. No. 10/271,334, Notice of Allowance dated Aug. 26, 2005", 3 pgs.
"U.S. Appl. No. 10/271,334, Response filed Mar. 15, 2004 to Restriction Requirement dated Sep. 23, 2003", 1 pg.
"U.S. Appl. No. 10/271,334, Restriction Requirement dated Sep. 23, 2003", 4 pgs.
"U.S. Appl. No. 10/307,226, 312 Amendment filed Oct. 24, 2011", 3 pgs.
"U.S. Appl. No. 10/307,226, Appeal Brief filed Oct. 14, 2010", 15 pgs.
"U.S. Appl. No. 10/307,226, Final Office Action dated Jun. 27, 2008", 6 pgs.
"U.S. Appl. No. 10/307,226, Final Office Action dated Dec. 12, 2006", 5 pgs.
"U.S. Appl. No. 10/307,226, Non Final Office Action dated Mar. 13, 2006", 6 pgs.
"U.S. Appl. No. 10/307,226, Non Final Office Action dated Jun. 12, 2007", 5 pgs.
"U.S. Appl. No. 10/307,226, Non Final Office Action Sep. 9, 2009", 16 pgs.
"U.S. Appl. No. 10/307,226, Notice of Allowance dated Jul. 22, 2011 ", 8 pgs.
"U.S. Appl. No. 10/307,226, Preliminary Amendment filed Jul. 22, 2005", 3 pgs.
"U.S. Appl. No. 10/307,226, PTO Response to 312 Amendment dated Nov. 10, 2011", 3 loas.
"U.S. Appl. No. 10/307,226, Response filed Apr. 9, 2007 to Final Office Action dated Dec. 12, 2006", 7 DOS.
"U.S. Appl. No. 10/307,226, Response filed Jun. 23, 2009 to Final Office Action dated Jun. 27, 2008", 10 DOS.
"U.S. Appl. No. 10/307,226, Response filed Sep. 15, 2006 to Non Final Office Action dated Mar. 13, 2006", 6 pgs.
"U.S. Appl. No. 10/307,226, Response filed Dec. 14, 2007 to Non Final Office Action dated Jun. 12, 2007", 7 pgs.
"U.S. Appl. No. 10/669,881, Final Office Action dated Jan. 25, 2008", 7 pgs.
"U.S. Appl. No. 10/669,881, Non Final Office Action dated Jan. 27, 2006", 5 pgs.
"U.S. Appl. No. 10/669,881, Notice of Allowance dated Oct. 8, 2008", 16 pgs.
"U.S. Appl. No. 10/669,881, Preliminary Amendment dated May 6, 2005", 3 pgs.
"U.S. Appl. No. 10/669,881, Response filed Mar. 11, 2008 to Final Office Action dated Jan. 25, 2008", 8 pgs.
"U.S. Appl. No. 10/669,881, Response filed May 15, 2006 to Non Final Office Action dated Jan. 27, 2006", 9 pgs.
"U.S. Appl. No. 10/669,881, Response filed Sep. 7, 2007 to Restriction Requirement dated Sep. 7, 2007", 4 pgs.
"U.S. Appl. No. 10/669,881, Response filed Oct. 2, 2006 to Restriction Requirement dated Jul. 27, 2006", 6 pgs.
"U.S. Appl. No. 10/669,881, Restriction Requirement dated Jul. 27, 2006", 5 pgs.
"U.S. Appl. No. 10/669,881, Restriction Requirement dated Jun. 19, 2007", 5 pgs.
"U.S. Appl. No. 10/692,282, Non Final Office Action dated Aug. 30, 2005", 6 pgs.
"U.S. Appl. No. 10/692,282, Notice of Allowance dated Jun. 13, 2006", 6 pgs.
"U.S. Appl. No. 10/692,282, Response filed Feb. 22, 2005 to Restriction Requirement dated Aug. 17, 2004", 4 pgs.
"U.S. Appl. No. 10/692,282, Response filed Feb. 28, 2006 to Non Final Office Action dated Aug. 30, 2005", 5 pgs.
"U.S. Appl. No. 10/692,282, Restriction Requirement dated Aug. 17, 2004", 6 pgs.
"U.S. Appl. No. 10/693,255, Examiner Interview Summary dated Feb. 17, 2005", 3 pgs.
"U.S. Appl. No. 10/693,255, Non Final Office Action dated Dec. 9, 2004", 6 pgs.
"U.S. Appl. No. 10/693,255, Notice of Allowance dated Mar. 9, 2005", 9 pgs.
"U.S. Appl. No. 10/752,435, Final Office Action dated May 14, 2010", 8 pgs.
"U.S. Appl. No. 10/752,435, Final Office Action dated Jul. 12, 2007", 8 pgs.
"U.S. Appl. No. 10/752,435, Final Office Action dated Dec. 8, 2008", 8 pgs.
"U.S. Appl. No. 10/752,435, Non Final Office Action dated Mar. 18, 2008", 7 pgs.
"U.S. Appl. No. 10/752,435, Non Final Office Action dated Jul. 21, 2009", 7 pgs.
"U.S. Appl. No. 10/752,435, Non Final Office Action dated Oct. 19, 2006", 17 pgs.
"U.S. Appl. No. 10/786,465, Applicant's Summary of Examiner Interview filed Jun. 6, 2012", 2 DOS.
"U.S. Appl. No. 10/786,465, Corrected Notice of Allowability dated Jul. 2, 2012", 4 pgs.
"U.S. Appl. No. 10/786,465, Examiner Interview Summary dated Mar. 3, 2008", 2 pgs.
"U.S. Appl. No. 10/786,465, Examiner Interview Summary dated Apr. 26, 2011", 3 pgs.
"U.S. Appl. No. 10/786,465, Preliminary Amendment filed May 16, 2005", 3 pgs.
"U.S. Appl. No. 10/786,465, Response filed Jan. 25, 2008 to Non Final Office Action dated Jul. 23, 2007", 8 pgs.
"U.S. Appl. No. 10/786,465, Response filed Apr. 9, 2007 to Restriction Requirement dated Dec. 8, 2006", 4 pgs.
"U.S. Appl. No. 10/786,465, Response filed Apr. 26, 2011 to Non Final Office Action dated Mar. 26, 2010", 14 pgs.
"U.S. Appl. No. 10/786,465, Response filed Jul. 22, 2009 to Final Office Action dated Jan. 21, 2009", 5 pgs.
"U.S. Appl. No. 10/786,465, Response filed Sep. 19, 2008 to Restriction Requirement dated Jul. 24, 2008", 4 pgs.
"U.S. Appl. No. 10/786,465, Restriction Requirement dated Jul. 24, 2008", 5 pgs.

(56) References Cited

OTHER PUBLICATIONS

"U.S. Appl. No. 10/786,465, Restriction Requirement dated Dec. 8, 2006", 6 pgs.
"U.S. Appl. No. 10/786,465, Supplemental Amendment filed Mar. 18, 2008", 8 pgs.
"U.S. Appl. No. 10/786,465, Supplemental Notice of Allowability dated May 8, 2012", 6 pgs.
"U.S. Appl. No. 10/808,216, Preliminary Amendment filed Jun. 15, 2005", 3 pgs.
"U.S. Appl. No. 11/166,411, 312 Amendment filed Nov. 23, 2011", 3 pgs.
"U.S. Appl. No. 11/166,411, Final Office Action dated Dec. 3, 2009", 5 pgs.
"U.S. Appl. No. 11/166,411, Non Final Office Action dated May 5, 2009", 8 pgs.
"U.S. Appl. No. 11/166,411, Preliminary Amendment filed Oct. 2, 2006", 5 pgs.
"U.S. Appl. No. 11/166,411, PTO Response to 312 Communication dated Dec. 13, 2011", 2 pgs.
"U.S. Appl. No. 11/166,411, Response filed Jan. 12, 2009 to Restriction Requirement dated Jul. 15, 2008", 5 pgs.
"U.S. Appl. No. 11/166,411, Response filed Jun. 7, 2010 to Final Office Action dated Dec. 3, 2009", 5 pgs.
"U.S. Appl. No. 11/166,411, Response filed Nov. 9, 2009 to Non Final Office Action dated May 5, 2009", 8 pgs.
"U.S. Appl. No. 11/166,411, Restriction Requirement dated Jul. 15, 2008", 5 pgs.
"U.S. Appl. No. 11/166,411, Supplemental Preliminary Amendment filed Oct. 30, 2007", 7 pgs.
"U.S. Appl. No. 11/166,428, Final Office Action dated Jan. 12, 2009", 10 pgs.
"U.S. Appl. No. 11/166,428, Final Office Action dated Mar. 16, 2010", 8 pgs.
"U.S. Appl. No. 11/166,428, Non Final Office Action dated May 14, 2008", 6 pgs.
"U.S. Appl. No. 11/166,428, Non Final Office Action dated Jun. 16, 2009", 10 pgs.
"U.S. Appl. No. 11/254,444, Notice of Allowance dated Apr. 5, 2010", 4 pgs.
"U.S. Appl. No. 11/254,444, Preliminary Amendment filed Oct. 20, 2005".
"U.S. Appl. No. 11/254,444, Preliminary Amendment filed Nov. 15, 2005", 8 pgs.
"U.S. Appl. No. 11/254,444, Response filed Dec. 18, 2009 to Restriction Requirement dated Jun. 19, 2009", 2 pgs.
"U.S. Appl. No. 11/254,444, Restriction Requirement dated Jun. 19, 2009", 6 pgs.
"U.S. Appl. No. 11/254,619, Response filed Apr. 1, 2010 to Non Final Office Action dated Oct. 1, 2009", 5 pgs.
"U.S. Appl. No. 11/254,619, Response filed Apr. 20, 2012 to Final Office Action dated Oct. 20, 2011", 11 pgs.
"U.S. Appl. No. 11/254,619, Response filed Aug. 3, 2011 to Non Final Office Action dated Feb. 3, 2011 ", 13 pgs.
"U.S. Appl. No. 11/254,619, Response filed Dec. 20, 2010 to Final Office Action dated Jun. 30, 2010", 12 pgs.
"U.S. Appl. No. 11/254,950, Preliminary Amendment filed Nov. 18, 2005", 4 pgs.
"U.S. Appl. No. 11/254,950, Response filed Jan. 5, 2009 to Restriction Requirement dated Jul. 9, 2008", 7 pgs.
"U.S. Appl. No. 11/254,950, Response filed Oct. 5, 2009 to Non Final Office Action dated Mar. 30, 2009", 5 pgs.
"U.S. Appl. No. 11/254,950, Restriction Requirement dated Jul. 9, 2008", 9 pgs.
"U.S. Appl. No. 11/255,116, Preliminary Amendment filed Nov. 18, 2005", 4 pgs.
"U.S. Appl. No. 11/255,116, Response filed May 20, 2009 to Restriction Requirement dated Mar. 18, 2009", 4 pgs.
"U.S. Appl. No. 11/255,116, Response filed Nov. 17, 2008 to Non Final Office Action dated May 24, 2008", 7 pgs.
"U.S. Appl. No. 11/255,116, Restriction Requirement dated Mar. 18, 2009", 7 pgs.
"U.S. Appl. No. 11/365,056, Final Office Action dated Dec. 9, 2010", 13 pgs.
"U.S. Appl. No. 11/365,056, Non Final Office Action dated Mar. 23, 2010", 11 pgs.
"U.S. Appl. No. 11/365,056, Response filed Sep. 28, 2010 to Non Final Office Action dated Mar. 23, 2010", 5 pgs.
"U.S. Appl. No. 11/365,056, Response filed Dec. 10, 2009 to Restriction Requirement dated Jun. 10, 2009", 44 pgs.
"U.S. Appl. No. 11/365,056, Restriction Requirement dated Jun. 10, 2009", 5 pgs.
"U.S. Appl. No. 11/488,305, Advisory Action dated Jun. 7, 2013", 3 pgs.
"U.S. Appl. No. 11/488,305, Final Office Action dated Mar. 6, 2013", 9 pgs.
"U.S. Appl. No. 11/488,305, Non Final Office Action dated Sep. 14, 2012", 9 pgs.
"U.S. Appl. No. 11/488,305, Response filed Feb. 1, 2011 to Non Final Office Action dated Sep. 1, 2010", 12 pgs.
"U.S. Appl. No. 11/488,305, Response filed Feb. 13, 2013 to Non Final Office Action dated Sep. 14, 2012", 10 pgs.
"U.S. Appl. No. 11/488,305, Response filed Apr. 26, 2012 to Non Final Office Action dated Oct. 31, 2011", 12 pgs.
"U.S. Appl. No. 11/488,305, Response filed May 3, 2013 to Final Office Action dated Mar. 6, 2013", 11 pgs.
"U.S. Appl. No. 11/488,305, Response filed Jul. 2, 2010 to Restriction Requirement dated Jan. 5, 2010", 8 pgs.
"dated U.S. Appl. No. 11/488,305, Response filed Oct. 13, 2011 to Final Office Action dated Apr. 13, 2011", 11 pgs.
"U.S. Appl. No. 11/488,305, Restriction Requirement dated Jan. 5, 2010", 6 pgs.
"U.S. Appl. No. 11/540,427, Appeal Brieffiled Aug. 26, 2010", 26 pgs.
"U.S. Appl. No. 11/540,427, Notice of Allowance dated Apr. 11, 2011 ", 8 pgs.
"U.S. Appl. No. 11/540,427, Preliminary Amendment filed Oct. 3, 2007", 5 pgs.
"U.S. Appl. No. 11/540,427, Response filed Apr. 10, 2009 to Non Final Office Action dated Oct. 6, 2008", 6 pgs.
"U.S. Appl. No. 11/540,428, Response filed May 12, 2011 to Non Final Office Action dated Nov. 12, 2010", 12 pgs.
"U.S. Appl. No. 11/540,428, Response filed Oct. 1, 2010 to Restriction Requirement dated Mar. 29, 2010", 6 pgs.
"U.S. Appl. No. 11/540,428, Restriction Requirement dated Mar. 29, 2010", 9 pgs.
"U.S. Appl. No. 11/580,584, Appeal Brieffiled Nov. 15, 2010", 11 pgs.
"U.S. Appl. No. 11/580,584, Final Office Action dated Jan. 22, 2009", 9 pgs.
"U.S. Appl. No. 11/580,584, Final Office Action dated Oct. 16, 2009", 8 pgs.
"U.S. Appl. No. 11/580,584, Non Final Office Action dated Apr. 18, 2008", 6 pgs.
"U.S. Appl. No. 11/580,584, Notice of Allowance dated Feb. 4, 2011 ", 7 pgs.
"U.S. Appl. No. 11/580,584, Response filed Jul. 22, 2009 to Final Office Action dated Jan. 22, 2009", 6 pgs.
"U.S. Appl. No. 11/580,584, Response filed Oct. 20, 2008 to Non Final Office Action dated Apr. 18, 2008", 5 pgs.
"U.S. Appl. No. 11/978,752, Final Office Action dated Dec. 22, 2010", 6 pgs.
"dated U.S. Appl. No. 11/978,752, Response filed May 10, 2010 to Restriction Requirement dated Nov. 6, 2009", 4 pgs.
"U.S. Appl. No. 11/978,752, Response filed Nov. 5, 2010 to Non Final Office Action dated May 20, 2010", 4 pgs.
"U.S. Appl. No. 11/978,752, Restriction Requirement dated Nov. 6, 2009", 7 pgs.
"U.S. Appl. No. 11/978,753, Response filed Mar. 3, 2011 to Non Final Office Action dated Sep. 3, 2010", 9 pgs.
"U.S. Appl. No. 11/981, 112, Final Office Action dated Apr. 29, 2010", 9 pgs.

(56) References Cited

OTHER PUBLICATIONS

"U.S. Appl. No. 11/981, 112, Non Final Office Action dated Jul. 8, 2009", 11 pgs.
"U.S. Appl. No. 12/288,031, Advisory Action dated Apr. 12, 2013", 3 pgs.
"U.S. Appl. No. 12/288,031, Final Office Action dated Jan. 3, 2012", 9 pgs.
"U.S. Appl. No. 12/288,031, Non Final Office Action dated May 10, 2012", 8 pgs.
"U.S. Appl. No. 12/288,031, Non Final Office Action dated Jul. 15, 2013", 9 pgs.
"U.S. Appl. No. 12/288,031, Response filed Mar. 25, 2013 to Final Office Action dated Jan. 3, 2013", 11 DOS.
"U.S. Appl. No. 12/288,031, Response filed Apr. 4, 2012 to Restriction Requirement dated Nov. 4, 2011", 3 pgs.
"U.S. Appl. No. 12/288,031, Response filed Oct. 10, 2012 to Non Final Office Action dated May 10, 2012", 11 pgs.
"U.S. Appl. No. 12/288,031, Restriction Requirement dated Nov. 4, 2011", 9 pgs.
"U.S. Appl. No. 12/288,032, Restriction Requirement dated Nov. 4, 2011", 9 pgs.
"U.S. Appl. No. 12/288,034, Non Final Office Action dated Jun. 22, 2012", 7 pgs.
"U.S. Appl. No. 12/288,034, Response filed May 1, 2012 to Restriction Requirement dated Nov. 3, 2011", 4 pgs.
"U.S. Appl. No. 12/288,034, Response filed Dec. 21, 2012 to Non Final Office Action dated Jun. 22, 2012", 12 pgs.
"U.S. Appl. No. 12/288,034, Restriction Requirement dated Nov. 3, 2011", 9 pgs.
"U.S. Appl. No. 12/288,045, Restriction Requirement dated Nov. 16, 2011", 9 pgs.
"U.S. Appl. No. 12/653,219, Non Final Office Action dated May 30, 2012", 16 pgs.
"U.S. Appl. No. 12/917,842, Non Final Office Action dated Nov. 13, 2012", 6 pgs.
"U.S. Appl. No. 12/917,842, Notice of Allowance dated May 20, 2013", 8 pgs.
"U.S. Appl. No. 12/917,842, Notice of Allowance dated Aug. 27, 2013", 6 pgs.
"U.S. Appl. No. 12/917,842, Response filed Apr. 15, 2013 to Non Final Office Action dated Nov. 13, 2012", 9 pgs.
"U.S. Appl. No. 12/917,842, Response filed Oct. 15, 2012 to Restriction Requirement dated Sep. 14, 2012", 2 pgs.
"U.S. Appl. No. 12/917,842, Restriction Requirement dated Sep. 14, 2012", 5 pgs.
"U.S. Appl. No. 13/157,242, Advisory Action dated Jul. 30, 2013", 3 pgs.
"U.S. Appl. No. 13/157,242, Final Office Action dated May 16, 2013", 7 pgs.
"U.S. Appl. No. 13/157,242, Non Final Office Action dated Jun. 18, 2012", 9 pgs.
"U.S. Appl. No. 13/157,242, Preliminary Amendment filed Jun. 9, 2011", 7 pgs.
"U.S. Appl. No. 13/157,242, Response filed Jun. 1, 2012 to Restriction Requirement dated May 1 2012", 3 pgs.
"U.S. Appl. No. 13/157,242, Response filed Jul. 16, 2013 to Final Office Action dated May 16, 2013", 9 pgs.
"U.S. Appl. No. 13/157,242, Response filed Dec. 18, 2012 to Non Final Office Action dated Jun. 18, 2012", 11 pgs.
"U.S. Appl. No. 13/157,242, Restriction Requirement dated May 1, 2012", 6 pgs.
"U.S. Appl. No. 13/162,384, Final Office Action dated Aug. 27, 2013", 14 pgs.
"U.S. Appl. No. 13/162,384, Non Final Office Action dated Mar. 28, 2013", 8 pgs.
"U.S. Appl. No. 13/162,384, Preliminary Amendment filed Jun. 16, 2011", 7 pgs.
"U.S. Appl. No. 13/162,384, Response filed Jun. 27, 2013", 9 pgs.
"U.S. Appl. No. 13/495,836, Non Final Office Action dated Aug. 5, 2013", 7 pgs.
"U.S. Appl. No. 13/495,836, Non Final Office Action dated Dec. 26, 2012", 9 pgs.
"U.S. Appl. No. 13/495,836, Preliminary Amendment filed Jun. 13, 2012", 8 pgs.
"U.S. Appl. No. 13/495,836, Response filed May 25, 2013 to Non Final Office Action dated Dec. 26, 2012", 9 pgs.
"Australian Application Serial No. 2002351188, Office Action dated Mar. 30, 2007", 1 pg.
"Australian Application Serial No. 2002351188, Office Action dated Dec. 8, 2008", 3 pgs.
"Australian Application Serial No. 2002353807, First Examiner Report dated Nov. 16, 2006", 2 IDOS.
"Australian Application Serial No. 2004277897, First Examiner Report dated Oct. 14, 2009", 2 pgs.
"Australian Application Serial No. 2004277897, Response filed Jul. 14, 2011 to First Examiner Report dated Oct. 14, 2009", 9 pgs.
"Australian Application Serial No. 2004287354, Office Action dated Oct. 13, 2009", 2 pgs.
"Australian Application Serial No. 2005235108, Office Action dated Feb. 26, 2010", 3 pgs.
"Australian Application Serial No. 2006302908, Office Action dated Mar. 4, 2011", 8 pgs.
"Australian Application Serial No. 2006305688, First Examiner Report dated Mar. 10, 2011", 3 loas.
"Australian Application Serial No. 2006305688, Response filed Oct. 22, 2012 to First Examiner Report dated Mar. 10, 2011", 16 pgs.
"Australian Application Appl. No. 2006305689, Office Action dated Sep. 5, 2011", 3 pgs.
"Australian Application Serial No. 2006309241, Office Action dated Mar. 4, 2011", 6 pgs.
"Australian Application Serial No. 2008243229, First Examiner Report dated Mar. 13, 2010", 2 pgs.
"Australian Application Serial No. 2008243229, Response filed May 13, 2011 to Office Action dated Mar. 13, 2010", 15 pgs.
"Australian Application Serial No. 2011224089, First Examiners Report dated Mar. 27, 2013", 3 IPQS.
"Australian Application Serial No. 2011253682, Office Action dated Sep. 27, 2012", 4 pgs.
"Australian Application Serial No. 2011253682, Response filed Jul. 17, 2013 to Office Action dated Sep. 27, 2012", 19 pgs.
"Canadian Application Serial No. 2,464,900, Office Action dated Sep. 29, 2009", 3 pgs.
"Canadian Application Serial No. 2,539,585, Office Action dated Aug. 31, 2010", 2 pgs.
"Canadian Application Serial No. 2,539,585, Office Action dated Sep. 19, 2012", 2 pgs.
"Canadian Application Serial No. 2,546,681, Office Action dated Feb. 25, 2011", 3 pgs.
"Canadian Application Serial No. 2,554,022, Office Action dated Jun. 22, 2011", 3 pgs.
"Canadian Application Serial No. 2,554,022, Office Action dated Aug. 31, 2010", 2 pgs.
"Canadian Application Serial No. 2,558,317, Office Action dated Aug. 31, 2010", 2 pgs.
"Canadian Application Serial No. 2,558,317, Office Action dated Sep. 28, 2011", 3 pgs.
"Canadian Application Serial No. 2,626,403, Office Action dated Apr. 2, 2013", 3 pgs.
"Chinese Application Serial No. 02823581.9, Office Action dated Mar. 1, 2006", 7 pgs.
"Chinese Application Serial No. 02823581.9, Office Action dated Apr. 18, 2008", 6 pgs.
"Chinese Application Serial No. 02823581.9, Office Action dated Aug. 8, 2007", 4 pgs.
"Chinese Application Serial No. 02823581.9, Office Action dated Nov. 17, 2006", 7 pgs.
"Chinese Application Serial No. 02823581.9, Response filed Jan. 31, 2007 to Office Action dated Nov. 17, 2006", 8 pgs.
"Chinese Application Serial No. 02823581.9, Response filed Apr, 7, 2006 to Office Action dated Mar. 1, 2006", 4 pgs.
"Chinese Application Serial No. 02823581. 9, Response filed May 19, 2008 to Office Action dated Apr. 18, 2008", 38 pgs.

(56) References Cited

OTHER PUBLICATIONS

"Chinese Application Serial No. 02823581.9, Response filed Dec. 3, 2007 to Office Action dated Aug. 8, 2007", 6 pgs.
"Chinese Application Serial No. 200480027649.7, Office Action dated Jun. 23, 2008", w/Enqlish translation, 5 Dos.
"Chinese Application Serial No. 200480027649.7, Office Action dated Sep. 4, 2009", w/Enqlish translation, 18 Dos.
"Chinese Application Serial No. 200480027649.7, Office Action dated Dec. 24, 2010", w/English translation, 6 Dos.
"Chinese Application Serial No. 200480027649.7, Response filed Jan. 19, 2010 to Office Action dated Sep. 4, 2009", 5 pgs.
"Chinese Application Serial No. 200480027649.7, Response filed Mar. 8, 2011 to Office Action dated Dec. 24, 2010", w/Enqlish translation, 7 Dos.
"Chinese Application Serial No. 200480031226.2, Office Action dated Jan. 23, 2009", 9 pgs.
"Chinese Application Serial No. 200480031226.2, Office Action dated Apr. 27, 2010", 7 pgs.
"Chinese Application Serial No. 200480031226.2, Office Action ated Dec. 21, 2010", 10 pgs.
"Chinese Application Serial No. 200480031226.2, Response filed Feb. 25, 2011 to Office Action dated Dec. 21, 2010", 18 pgs.
"Chinese Application Serial No. 200480031226.2, Response filed May 22, 2009 to Office Action dated Jan. 23, 2009", 5 pgs.
"Chinese Application Serial No. 200480031226.2, Response filed Jul. 12, 2010 to Office Action dated Apr. 27, 2010", Chinese only, 5 pgs.
"Chinese Application Serial No. 200580006169.7, Office Action dated Mar. 1, 2010", w/English translation, 12 Dos.
"Chinese Application Serial No. 200580006169.7, Response filed Jul. 14, 2010 to Office Action dated Mar. 1, 2010", w/English translation, 32 pgs.
"Chinese Application Serial No. 200580009570.6, Office Action dated May 9, 2008".
"Chinese Application Serial No. 200580009570.6, Response filed Nov. 21, 2008 to Office Action dated May 9, 2008", 7 pgs.
"Chinese Application Serial No. 200680034052.4, Office Action dated May 11, 2010", w/English translation, 7 pgs.
"Chinese Application Serial No. 200680034052.4, Office Action dated Aug. 14, 2009", w/English translation, 13 pgs.
"Chinese Application Serial No. 200680034052.4, Response filed Mar. 1, 2010 to Office Action dated Aug. 14, 2009", 4 pgs.
"Chinese Application Serial No. 200680034052.4, Response filed Sep. 26, 2010 to Office Action dated May 11, 2010", 5 pgs.
"Chinese Application Serial No. 200680038882.4, Office Action dated May 11, 2010", 18 pgs.
"Chinese Application Serial No. 200680046854.7, Office Action dated Apr. 14, 2010", 18 pgs.
"Chinese Application Serial No. 200680046854.7, Response filed Sep. 26, 2010 to Office Action dated Apr. 14, 2010", 10 pgs.
"Chinese Application Serial No. 200680047552.1, Office Action dated Jun. 4, 2010", 7 pgs.
"Chinese Application Serial No. 200680047552.1, Response filed Dec. 20, 2010 to Office Action dated Jun. 4, 2010", 10 pgs.
"Chinese Application Serial No. 200810210922.X, Office Action dated Jan. 19, 2012", 6 pgs.
"Chinese Application Serial No. 200810210922.X, Office Action dated Apr. 2, 2010", 4 pgs.
"Chinese Application Serial No. 200810210922.X, Office Action dated Aug. 23, 2011 ", 6 pgs.
"Chinese Application Serial No. 200810210922.X, Response filed Jun. 1, 2012 to Office Action dated Jan. 19, 2012", 5 pgs.
"Chinese Application Serial No. 200810210922.X, Response filed Aug. 12, 2010 to Office Action dated Apr. 2, 2010", 10 pgs.
"Chinese Application Serial No. 200910139527.1, Office Action dated Jul. 12, 2010", w/English translation, 9 pgs.
"Chinese Application Serial No. 200910139527.1, Response filed Nov. 28, 2011 to Office Action dated Jul. 12, 2010", 9 pgs.
"European Application Serial No. 02789196.9, European Search Report dated Aug. 14, 2009", 5 pgs.
"European Application Serial No. 02789196.9, Office Action dated Feb. 6, 2012", 4 pgs.
"European Application Serial No. 02789196.9, Office Action dated Mar. 7, 2012", 3 pgs.
"European Application Serial No. 02789196.9, Office Action dated Apr. 19, 2010", 4 pgs.
"European Application Serial No. 02789196.9, Office Action dated Jul. 14, 2011", 3 pgs.
"European Application Serial No. 02789196.9, Response filed Jan. 18, 2012 to Office Action dated Jul. 14, 2011", 19 pgs.
"European Application Serial No. 02789196.9, Response filed Feb. 16, 2012 to Office Action dated Feb. 6, 2012", 9 pgs.
"European Application Serial No. 02789196.9, Response filed Apr. 5, 2012 to Office Action dated Mar. 7, 2012", 5 pgs.
"European Application Serial No. 02789196.9, Response filed Oct. 25, 2010 to Office Action dated Apr. 19, 2010", 16 pgs.
"European Application Serial No. 04788653.6, Office Action dated May 19, 2006", 2 pgs.
"European Application Serial No. 05713941.2, Office Action dated Dec. 13, 2007", 2 pgs.
"European Application Serial No. 06802573.3, Extended European Search Report dated Feb. 15, 2012", 6 pgs.
"European Application Serial No. 06802573.3, Office Action dated Mar. 5, 2012", 1 pg.
"European Application Serial No. 06802573.3, Office Action dated May 28, 2008", 2 pgs.
"European Application Serial No. 06802573.3, Response filed Sep. 3, 2012 to Office Action dated Mar. 5, 2012", 15 pgs.
"European Application Serial No. 06802578.2, European Search Report dated Mar. 7, 2013", 10 pgs.
"European Application Serial No. 06802580.8, Office Action dated Feb. 25, 2013", 3 pgs.
"European Application Serial No. 09820886.1, Office Action dated Jun. 7, 2011", 2 pgs.
"European Application Serial No. 09820886.1, Response filed Dec. 8, 2011 to Office Action dated Jun. 7, 2011 ", 3 pgs.
"German Application Serial No. 10297483.7, Office Action dated Jan. 9, 2006", 4 pgs.
"German Application Serial No. 10297483.7, Office Action dated Jul. 8, 2006", 2 pgs.
"German Application Serial No. 10297483.7, Office Action mailed and Response filed Oct. 30, 2006", 8 oas.
"German Application Serial No. 10297483.7, Response filed Jul. 7, 2006 to Office Action dated Jan. 9, 2006", 14 pgs.
"German Application Serial No. 10297483.7, Response filed Oct. 26, 2006 to Office Action dated Jul. 8, 2006", 3 pgs.
"Great Britain Application Serial No. 0411107 .6, Office Action dated Feb. 28, 2005", 3 pgs.
"Great Britain Application Serial No. 0411107 .6, Office Action dated Sep. 29, 2005", 1 pg.
"Great Britain Application Serial No. 0411107 .6, Response filed Aug. 23, 2005 to Office Action dated Feb. 28, 2005", 3 pgs.
"Great Britain Application Serial No. 0411107 .6, Response filed Oct. 31, 2005 to Office Action dated Sep. 29, 2005", 4 pgs.
"Great Britain Application Serial No. 0522152.8, Office Action dated Dec. 5, 2005", 5 pgs.
"Great Britain Application Serial No. 0522152.8, Response filed Apr. 26, 2006 to Office Action dated Dec. 5, 2005", 48 pgs.
"International Application Serial No. PCT/US2002/032753, International Preliminary Examination Report dated Aug. 16, 2004", 3 oas.
"International Application Serial No. PCT/US2002/032753, International Search Report dated Mar. 6, 2003", 1 pg.
"International Application Serial No. PCT/US2004/027589, International Preliminary Report on Patentability dated Apr. 6, 2005", 4 oas.
"International Application Serial No. PCT/US2004/027589, International Search Report dated Apr. 6, 2005", 1 pg.
"International Application Serial No. PCT/US2004/027589, Written Opinion dated Apr. 6, 2005", 3 pgs.
"International Application Serial No. PCT/US2004/027590, International Preliminary Examination Report dated Feb. 16, 2006", 3 pgs.

(56) References Cited

OTHER PUBLICATIONS

"International Application Serial No. PCT/US2004/027590, International Search Report dated Jan. 12, 2005", 1 pg.
"International Application Serial No. PCT/US2004/027590, Written Opinion dated Jan. 12, 2005", 3 pgs.
"International Application Serial No. PCT/US2005/00059, International Preliminary Report on Patentability dated May 18, 2007", 8 pgs.
"International Application Serial No. PCT/US2005/00059, International Search Report dated Jan. 5, 2007", 3 pgs.
"International Application Serial No. PCT/US2005/00059, Written Opinion dated Jan. 5, 2007", 8 DOS.
"International Application Serial No. PCT/US2005/005453, International Preliminary Examination Report dated Mar. 13, 2006", 3 Dos.
"International Application Serial No. PCT/US2005/005453, International Preliminary Report on Patentability dated Feb. 16, 2006", 3 pgs.
"International Application Serial No. PCT/US2005/005453, International Search Report dated Aug. 30, 2005", 1 pg.
"International Application Serial No. PCT/US2005/005453, International Written Opinion dated Aug. 30, 2005", 3 pgs.
"International Application Serial No. PCT/US2005/005453, Written Opinion dated Aug. 30, 2005", 3 pgs.
"International Application Serial No. PCT/US2006/037085, International Preliminary Report on Patentability dated Jul. 24, 2008", 9 pgs.
"International Application Serial No. PCT/US2009/005604, International Preliminary Report on Patentability dated Jan. 13, 2011", 10 pgs.
"International Application Serial No. PCT/US2009/005607, International Preliminary Report on Patentability dated Jan. 9, 2011", 9 Dos.
"International Application Serial No. PCT/US2009/005607, International Search Report dated Dec. 11, 2009", 2 pgs.
"International Application Serial No. PCT/US2009/005607, Written Opinion dated Dec. 11, 2009", 6 pgs.
"International Application Serial No. PCT/US2009/005608, International Preliminary Report on Patentability dated Jan. 14, 2011", 7 pgs.
"International Application Serial No. PCT/US2009/005608, International Search Report dated Dec. 10, 2009", 2 pgs.
"International Application Serial No. PCT/US2009/005608, Written Opinion dated Dec. 10, 2009", 4 pgs.
"International Application Serial No. PCT/US2009/005609, International Preliminary Report on Patentability dated Jan. 9, 2011", 9 pgs.
"Japanese Application Serial No. 2003-546789, Office Action dated Feb. 26, 2009", w/English translation, 7 pgs.
"Japanese Application Serial No. 2003-546789, Office Action dated Jun. 16, 2008", w/English translation, 6 pgs.
"Japanese Application Serial No. 2003-546789, Office Action dated Oct. 7, 2009", 3 pgs.
"Japanese Application Serial No. 2003-546789, Response filed May 21, 2009 to Office Action dated Feb. 26, 2009", 6 pgs.
"Japanese Application Serial No. 2003-546789, Response filed Dec. 11, 2008 to Office Action dated Jun. 17, 2008", w/English translation, 9 pgs.
"Japanese Application Serial No. 2006-528036, Office Action dated Jan. 19, 2010", 3 pgs.
"Japanese Application Serial No. 2006-528036, Office Action dated Feb. 26, 2009", w/English translation, 5 pgs.
"Japanese Application Serial No. 2006-528036, Office Action dated Jun. 23, 2008", w/English translation, 5 pgs.
"Japanese Application Serial No. 2006-528036, Response filed Dec. 25, 2008 to Office Action dated Jun. 23, 2008", w/English translation, 9 pgs.
"Japanese Application Serial No. 2006-536616, Office Action dated Jun. 23, 2008", 8 pgs.
"Japanese Application Serial No. 2006-536616, Response filed Dec. 19, 2008 to Office Action dated Jun. 23, 2008", 9 pgs.
"Japanese Application Serial No. 2007500928, Office Action dated Jul. 1, 2010", w/English translation, 10 pgs.
"Japanese Application Serial No. 2007504965, Office Action dated Mar. 7, 2012", w/English translation, 4 pgs.
"Japanese Application Serial No. 2007504965, Office Action dated Jun. 14, 2011 ", w/English translation, 4 pgs.
"Japanese Application Serial No. 2007504965, Office Action dated Sep. 14, 2010", English translation, 1 pg.
"Japanese Application Serial No. 2007504965, Response filed Mar. 11, 2011 to Office Action dated Sep. 14, 2010", 8 pgs.
"Japanese Application Serial No. 2008-316282, Office Action dated May 16, 2011 ", 2 pgs.
"Japanese Application Serial No. 2008-316296, Office Action dated Feb. 28, 2011 ", 2 pgs.
"Japanese Application Serial No. 2008-316296, Office Action dated Jun. 22, 2010", 2 pgs.
"Japanese Application Serial No. 2008-323279, Office Action dated Sep. 30, 2010", 1 pg.
"Japanese Application Serial No. 2008-323290, Office Action dated Jun. 6, 2012", 8 pgs.
"Japanese Application Serial No. 2008-323290, Office Action dated Jun. 8, 2011 ", 8 pgs.
"Japanese Application Serial No. 2008-323290, Response filed Dec. 7, 2011 to Office Action dated Jun. 8, 2011 ", 16 pgs.
"Japanese Application Serial No. 2008-536574, Office Action dated Mar. 11, 2010", English only, 4 oas.
"Japanese Application Serial No. 2008-536574, Office Action dated Oct. 3, 2011", 7 pgs.
"Japanese Application Serial No. 2008-536575, Office Action dated Jul. 7, 2011 ", 5 pgs.
"Japanese Application Serial No. 2008-536576, Office Action dated Jul. 19, 2011 ", 4 pgs.
"Japanese Application Serial No. 2008-536577, Notice of Allowance dated May 30, 2012", 3 pgs.
"Japanese Application Serial No. 2008-536577, Office Action dated Jul. 8, 2011 ", w/English translation, 4 pgs.
"Japanese Application Serial No. 2008-536577, Response filed Jan. 6, 2012 to Office Action dated Jul. 8, 2011 ", 3 pgs.
Bolduc, Lee, "Devices, Systems, and Methods for Prosthesis Delivery and Implantation, Including the Use of a Fastener Tool", U.S. Appl. No. 12/917,842, filed Nov. 2, 2010, 120 pgs.

CATHETER BASED FASTENER IMPLANTATION APPARATUS AND METHODS

RELATED APPLICATIONS

This application is a divisional of U.S. patent application Ser. No. 12/315,015, filed Nov. 26, 2008 (now abandoned), which is a divisional of U.S. patent application Ser. No. 10/669,881, filed Sep. 24, 2003, (now U.S. Pat. No. 7,491, 232) which is a continuation-in-part of U.S. patent application Ser. No. 10/307,226, filed Nov. 29, 2002 (now U.S. Pat. No. 8,075,570), and which is also a continuation-in-part of U.S. patent application Ser. No. 10/271,334, filed Oct. 15, 2002 (now U.S. Pat. No. 6,960,217), and which is also a continuation-in-part of U.S. patent application Ser. No. 10/099,149, filed Mar. 15, 2002, (now U.S. Pat. No. 6,800, 081) which is a divisional of U.S. patent application Ser. No. 09/787,135, filed Jun. 4, 2001 (now U.S. Pat. No. 6,592, 593), and which claims the benefit of U.S. Provisional Application Ser. No. 60/101,050 filed Sep. 18, 1998.

FIELD OF THE INVENTION

The invention relates generally to the delivery of a prosthesis to a targeted site within the body, e.g., for the repair of diseased and/or damaged sections of a hollow body organ and/or blood vessel.

BACKGROUND OF THE INVENTION

The weakening of a vessel wall from damage or disease can lead to vessel dilatation and the formation of an aneurysm. Left untreated, an aneurysm can grow in size and may eventually rupture.

For example, aneurysms of the aorta primarily occur in abdominal region, usually in the infrarenal area between the renal arteries and the aortic bifurcation. Aneurysms can also occur in the thoracic region between the aortic arch and renal arteries. The rupture of an aortic aneurysm results in massive hemorrhaging and has a high rate of mortality.

Open surgical replacement of a diseased or damaged section of vessel can eliminate the risk of vessel rupture. In this procedure, the diseased or damaged section of vessel is removed and a prosthetic graft, made either in a straight of bifurcated configuration, is installed and then permanently attached and sealed to the ends of the native vessel by suture. The prosthetic grafts for these procedures are usually unsupported woven tubes and are typically made from polyester, ePTFE or other suitable materials. The grafts are longitudinally unsupported so they can accommodate changes in the morphology of the aneurysm and native vessel. However, these procedures require a large surgical incision and have a high rate of morbidity and mortality. In addition, many patients are unsuitable for this type of major surgery due to other co-morbidities.

Endovascular aneurysm repair has been introduced to overcome the problems associated with open surgical repair. The aneurysm is bridged with a vascular prosthesis, which is placed intraluminally. Typically these prosthetic grafts for aortic aneurysms are delivered collapsed on a catheter through the femoral artery. These grafts are usually designed with a fabric material attached to a metallic scaffolding (stent) structure, which expands or is expanded to contact the internal diameter of the vessel. Unlike open surgical aneurysm repair, intraluminally deployed grafts are not sutured to the native vessel, but rely on either barbs extending from the stent, which penetrate into the native vessel during deployment, or the radial expansion force of the stent itself is utilized to hold the graft in position. These graft attachment means do not provide the same level of attachment when compared to suture and can damage the native vessel upon deployment.

SUMMARY OF THE INVENTION

The invention provides apparatus and methods for implanting a fastener in a targeted body region, e.g., within a hollow body organ or an intraluminal space.

One aspect of the invention provides an intraluminal fastener applier comprising a guide body having a longitudinal axis sized and configured for intraluminal deployment in a hollow body organ. The fastener applier includes an actuated assembly carried by the guide body that is selectively operable to generate an implantation force to implant at least one fastener into tissue within the hollow body organ. The actuated assembly includes a driven member extending generally along the longitudinal axis, which is sized and configured to engage a selected fastener. The actuated assembly also includes a drive member coupled to the driven member to impart the implantation force to the driven element in a direction that is at an angle to the longitudinal axis of the guide body.

In one embodiment, the actuated assembly includes structure that maintains the angle between the driven member and the drive member at about ninety-degrees or less.

In one embodiment, the actuated assembly includes structure that maintains a fixed angle between the driven member and the drive member, which can be, e.g., ninety-degrees or less.

In one embodiment, the actuated assembly includes a control mechanism to articulate the driven member relative to the drive member to adjust the angle.

In one embodiment, stabilization means is associated with the guide body for applying a resolving force in a direction different than the implantation force direction to resolve at least a portion of the implantation force within the hollow body organ.

Another aspect of the invention provides a method that deploys an intraluminal fastener applier hollow body organ. The intraluminal fastener applier comprises a guide body having a longitudinal axis sized and configured for intraluminal deployment in a hollow body organ. The fastener applier includes an actuated assembly carried by the guide body that is selectively operable to generate an implantation force to implant at least one fastener into tissue within the hollow body organ. The actuated assembly includes a driven member extending generally along the longitudinal axis, which is sized and configured to engage a selected fastener. The actuated assembly also includes a drive member coupled to the driven member to impart the implantation force to the driven element in a direction that is at an angle to the longitudinal axis of the guide body.

The method places the driven member into contact with tissue along a side wall of the hollow body while the longitudinal axis of the guide body remains substantially aligned with a long axis of the hollow body organ. The method operates the drive member to impart the implantation force to the driven element in the direction that is at an angle to the longitudinal axis of the guide body, to thereby implant the fastener in the side wall while the guide body remains substantially aligned with the long axis of the hollow body organ.

In one embodiment, the method applies a resolving force at or near the drive member to resolve within the hollow body organ at least a portion of the implantation force.

In one embodiment, the guide body includes a catheter body having a column strength that applies a resolving force in a direction different than the implantation force direction to resolve at least a portion of the implantation force within the hollow body organ.

Another aspect of the invention provides a method that advances an intraluminal fastener applier to a location within a prosthesis that has been deployed at a target site along a side wall of an aorta where a diseased or damaged section exists. The intraluminal fastener applier comprises a guide body having a longitudinal axis sized and configured for intraluminal deployment in a hollow body organ. The fastener applier includes an actuated assembly carried by the guide body that is selectively operable to generate an implantation force to implant at least one fastener into tissue within the hollow body organ. The actuated assembly includes a driven member extending generally along the longitudinal axis, which is sized and configured to engage a selected fastener. The actuated assembly also includes a drive member coupled to the driven member to impart the implantation force to the driven element in a direction that is at an angle to the longitudinal axis of the guide body.

The method places the driven member in alignment with a desired fastening site on the prosthesis along the side wall of the aorta. Due to the angle, the longitudinal axis of the guide body remains substantially aligned with a long axis of the aorta. The method anchors the prosthesis to a side wall of the aorta by operating the drive member to impart the implantation force to the driven element in the direction that is at an angle to the longitudinal axis of the guide body. The method thereby implants the fastener into tissue in a side wall of the aorta, while the longitudinal axis of the guide body remains substantially aligned with a long axis of the aorta.

In one embodiment, the method applies a resolving force at or near the drive member to resolve within the aorta at least a portion of the implantation force.

In one embodiment, the guide body includes a catheter body having a column strength that applies a resolving force in a direction different than the implantation force direction to resolve at least a portion of the implantation force within the aorta.

According to any aspect of the invention, the fastener includes a tissue-piercing fastener having a sharpened distal tip for piercing and penetrating tissue. The tissue-piercing fastener can comprise, e.g., a helical fastener.

BRIEF DESCRIPTION OF THE DRAWINGS

The invention will be understood from the following detailed description of preferred embodiments, taken in conjunction with the accompanying drawings, wherein.

DETAILED DESCRIPTION OF THE INVENTION

I. Delivering a Prosthesis

Figure 1:
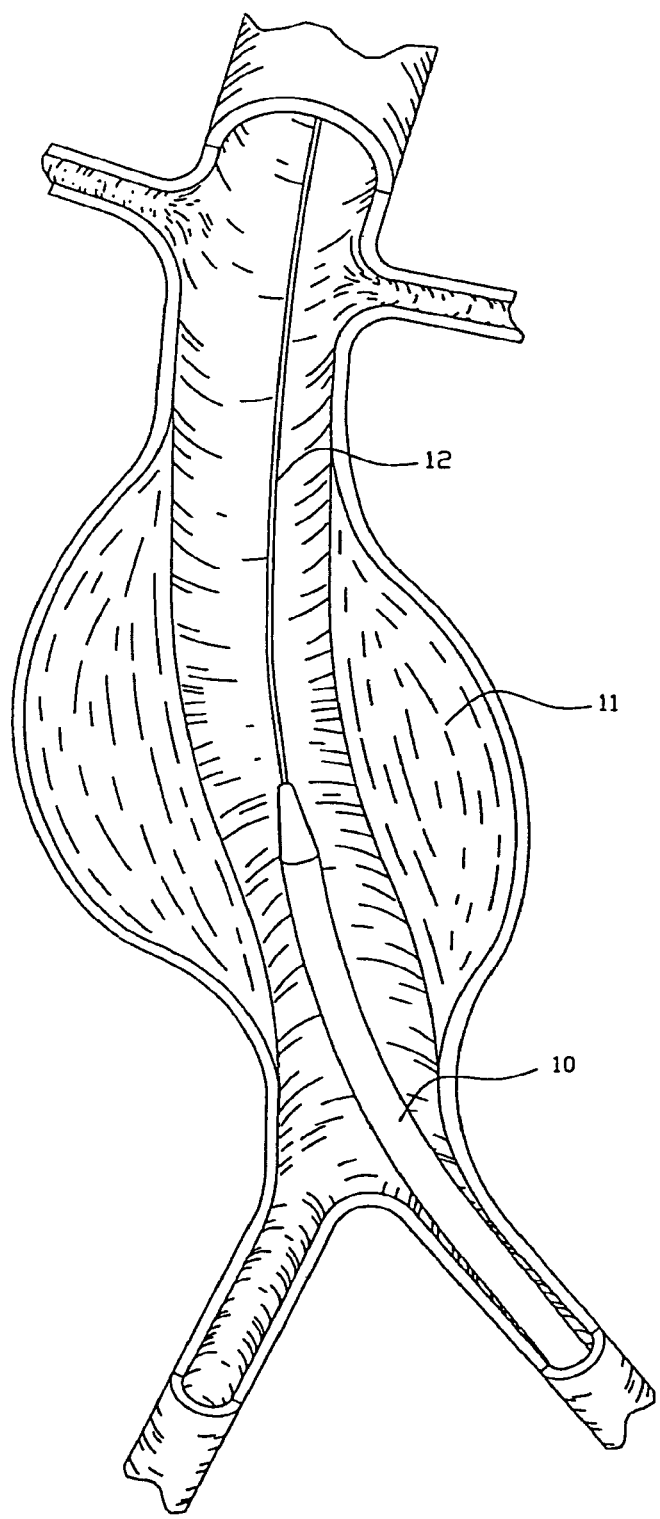
FIG. 1 is a perspective view of one embodiment of an endovascular graft delivery device shown positioned within an abdominal aortic aneurysm.

FIG. 1 depicts an endovascular graft delivery catheter 10 as it is being positioned over a guidewire 12 in a body lumen. The catheter 10 carries a prosthesis 14 (see FIG. 2), which is placed at a targeted site, e.g., by radial expansion of the prosthesis 14 (see FIG. 3). After partial or complete expansion of the prosthesis 14, one or more fasteners 28 (see FIGS. 15 and 16) are introduced by a fastener attachment assembly (as will be described in greater detail later) to anchor the prosthesis 14 in place.

For the purposes of illustration, FIG. 1 shows the targeted site as being within an abdominal aortic aneurysm 11. The targeted site can be elsewhere in the body. In the illustrated arrangement, the prosthesis 14 takes the form of an endovascular graft.

Figure 2:
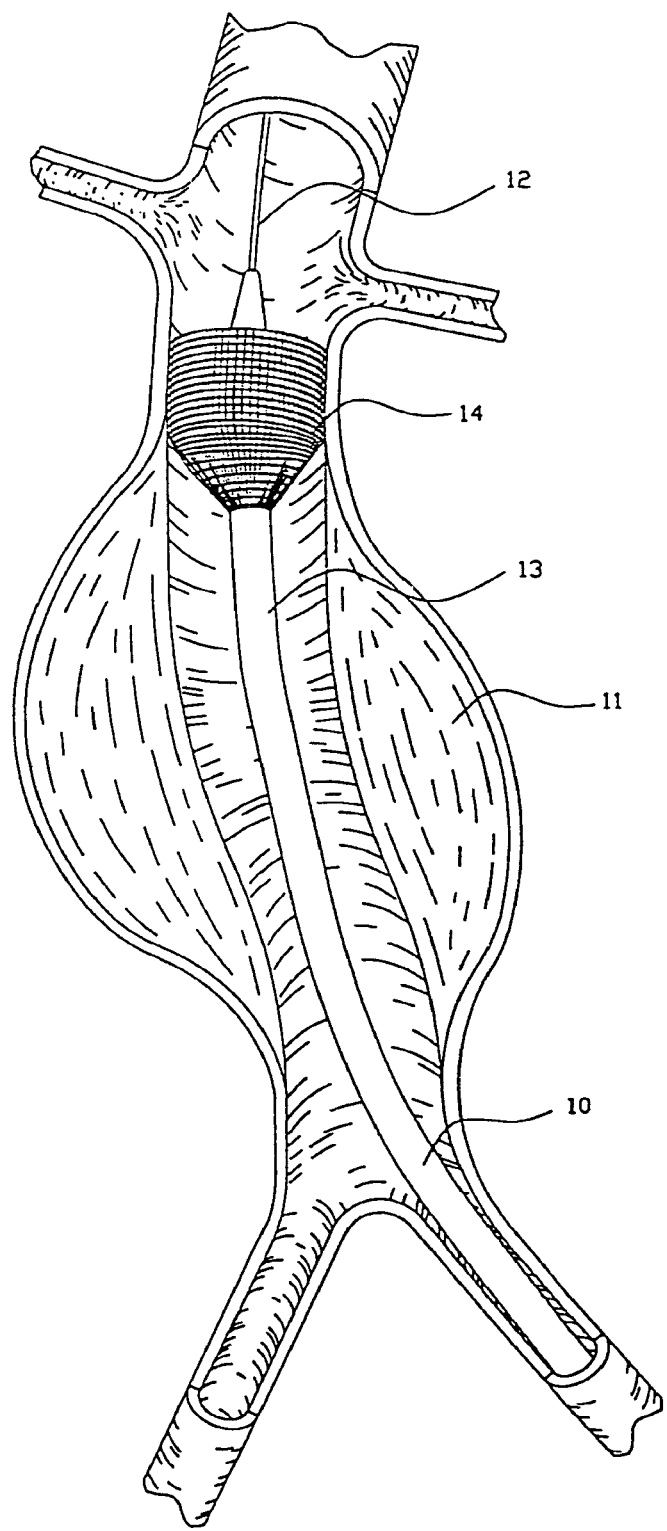
FIG. 2 is a perspective view of one embodiment the deployment of an endovascular graft within the aneurysm of FIG. 1.

FIG. 2 depicts the initial stage of graft deployment at the targeted site. While the deployment method can vary, in the illustrated embodiment, the delivery catheter 10 has a movable cover 13, which overlays the graft 14. When the cover 13 is pulled proximally, the graft 14 is free to radially expand, thereby enlarging to contact the internal walls of the blood vessel. The graft is shown to be self-expanding. Alternatively, the graft 14 can utilize an expanding member, such as a balloon or mechanical expander.

Figure 3:
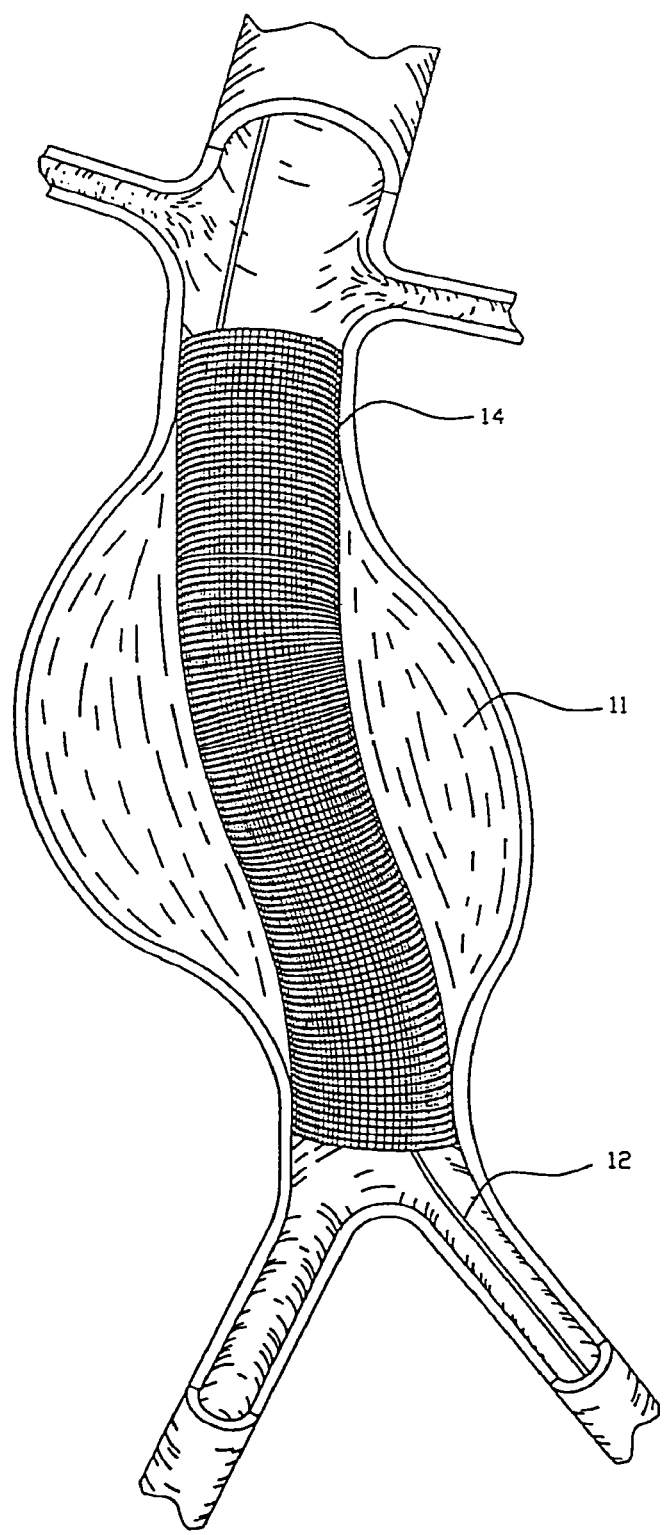
FIG. 3 is a perspective view of a fully deployed straight endovascular graft of FIG. 2.
Figure 4:
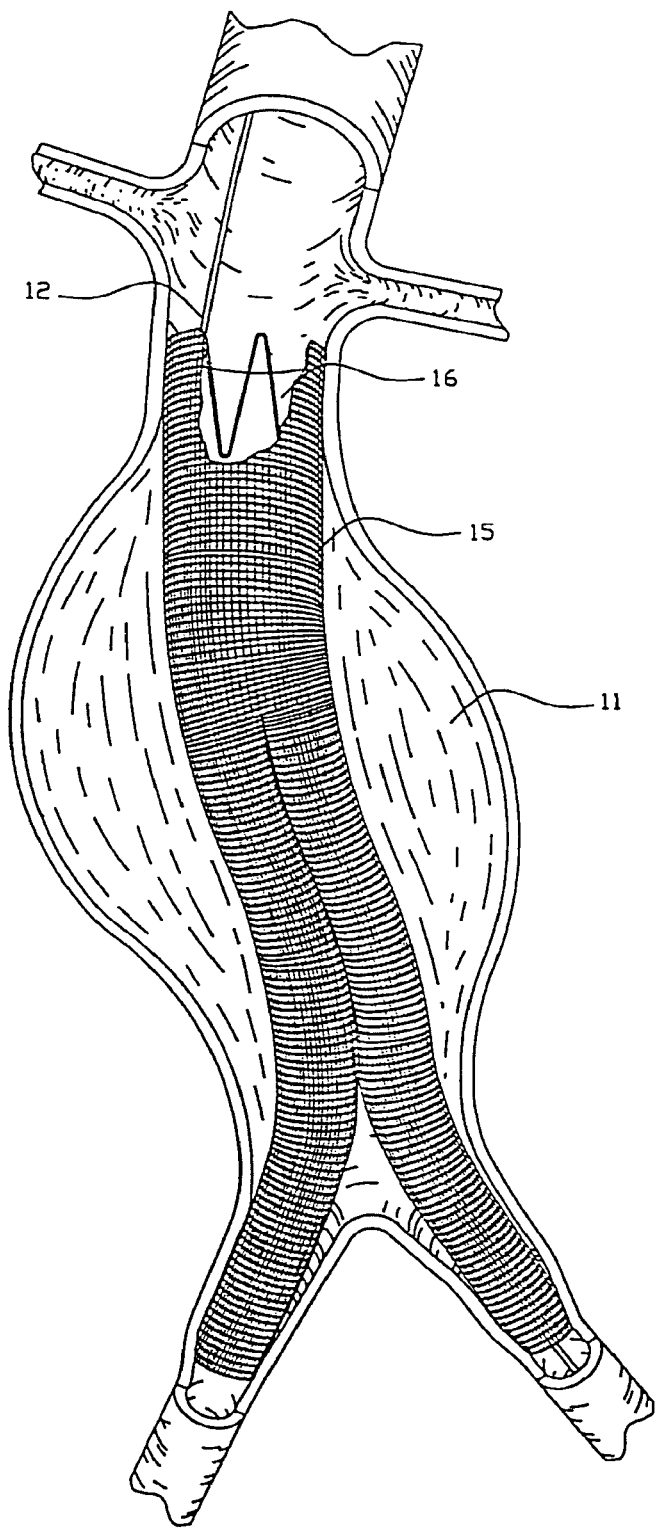
FIG. 4 is a perspective view of a fully deployed bifurcated endovascular graft broken away to show an anchoring scaffold at one end.

The process of graft deployment is continued, until the graft 14 is fully deployed or partially deployed within the vessel. The graft 14 can be sized and configured to be either straight or bifurcated form. FIG. 3 depicts a completely deployed straight graft 14. FIG. 4 depicts a completely deployed bifurcated graft 15.

A. The Prosthesis

The graft 14 desirably incorporates a support frame or scaffold 16. The scaffold 16 may be elastic, e.g., comprised of a shape memory alloy elastic stainless steel, or the like. For elastic scaffolds, expanding typically comprises releasing the scaffolding from a constraint to permit the scaffold to self-expand at the implantation site. In the illustrated arrangement, the cover 13 serves as a radial constraint. Alternatively, placement of a tubular catheter, delivery sheath, or the like over the scaffold 16 can serve to maintain the scaffold in a radially reduced configuration. In this arrangement, self-expansion of the scaffold 16 is achieved by pulling back on the radial constraining member, to permit the scaffold 16 to assume its larger diameter configuration.

Alternatively, the scaffold 16 may be constrained in an axially elongated configuration, e.g., by attaching either end of the scaffold to an internal tube, rod, catheter or the like. This maintains the scaffold 16 in the elongated, reduced diameter configuration. The scaffold 16 may then be released from such axial constraint in order to permit self-expansion.

Alternatively, the scaffold 16 may be formed from a malleable material, such as malleable stainless steel of other metals. Expansion may then comprise applying a radially expansive force within the scaffold to cause expansion, e.g., inflating a scaffold delivery catheter within the scaffold in order to affect the expansion. In this arrangement, the positioning and deployment of the endograft can be accomplished by the use of an expansion means either separate or incorporated into the deployment catheter. This will allow the endograft to be positioned within the vessel and partially deployed while checking relative position within the vessel. The expansion can be accomplished either via a balloon or mechanical expansion device. Additionally, this expansion stabilizes the position of the endograft within the artery by resisting the force of blood on the endograft until the endograft can be fully deployed.

The graft 14 may have a wide variety of conventional configurations. It can typically comprise a fabric or some other blood semi-impermeable flexible barrier which is supported by the scaffold 16, which can take the form of a stent structure. The stent structure can have any conventional stent configuration, such as zigzag, serpentine, expanding diamond, or combinations thereof. The stent structure may extend the entire length of the graft, and in some instances can be longer than the fabric components of the graft. Alternatively, the stent structure can cover only a small portion of the prosthesis, e.g., being present at the ends. The stent structure may have three or more ends when it is configured to treat bifurcated vascular regions, such as the treatment of abdominal aortic aneurysms, when the stent graft extends into the iliac arteries. In certain instances, the stent structures can be spaced apart along the entire length, or at least a major portion of the entire length, of the stent-graft, where individual stent structures are not connected to each other directly, but rather connected to the fabric or other flexible component of the graft.

Figure 5:
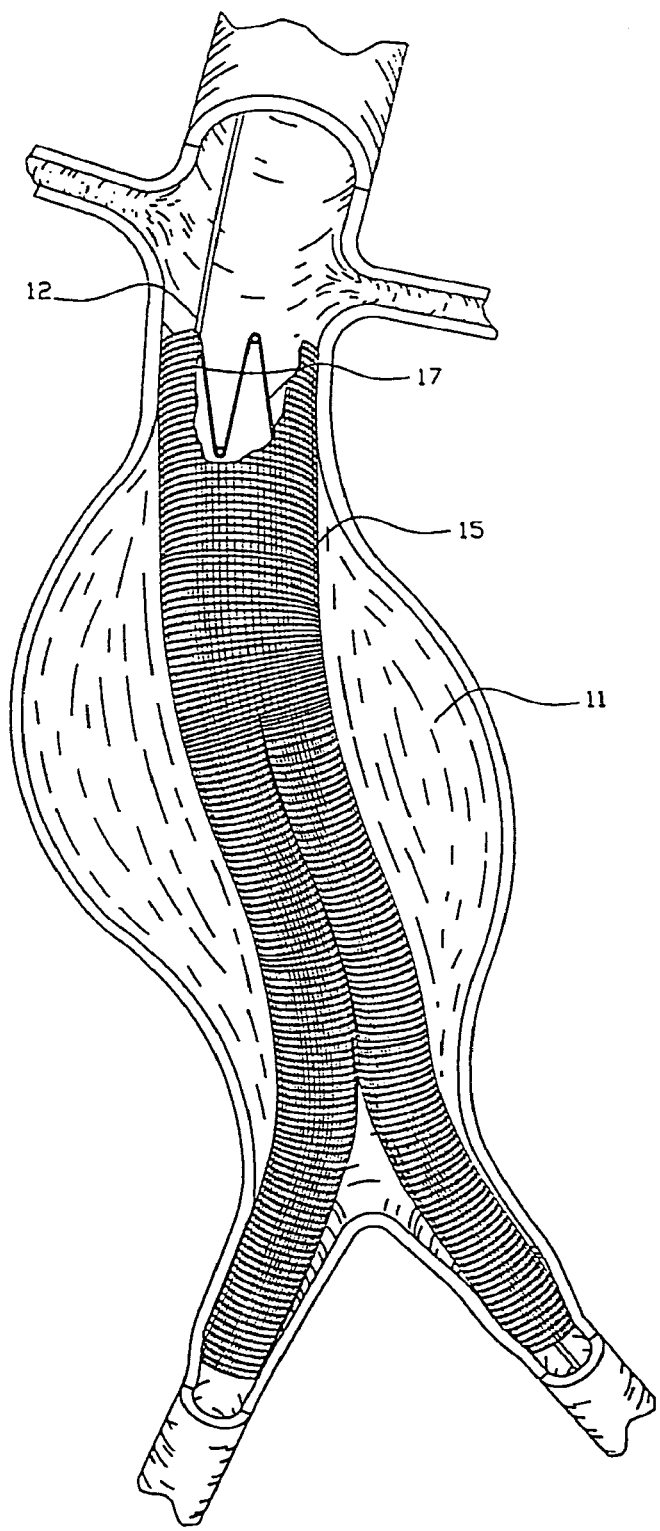
FIG. 5 is a perspective view similar to FIG. 5 showing an alternative scaffold structure.

One illustrative embodiment of the graft scaffold 16 or stent structure is illustrated in the area broke away in FIG. 4. Here, the stent structure is in the form of a simple zigzag pattern, however it is contemplated that the stent design could involve more complex patterns 17 as depicted in FIG. 5. Although only one stent structure within the graft is depicted, in FIGS. 4 and 5, it is contemplated that multiple independent stent structures could be incorporated into the graft, as previously described.

Figure 40:
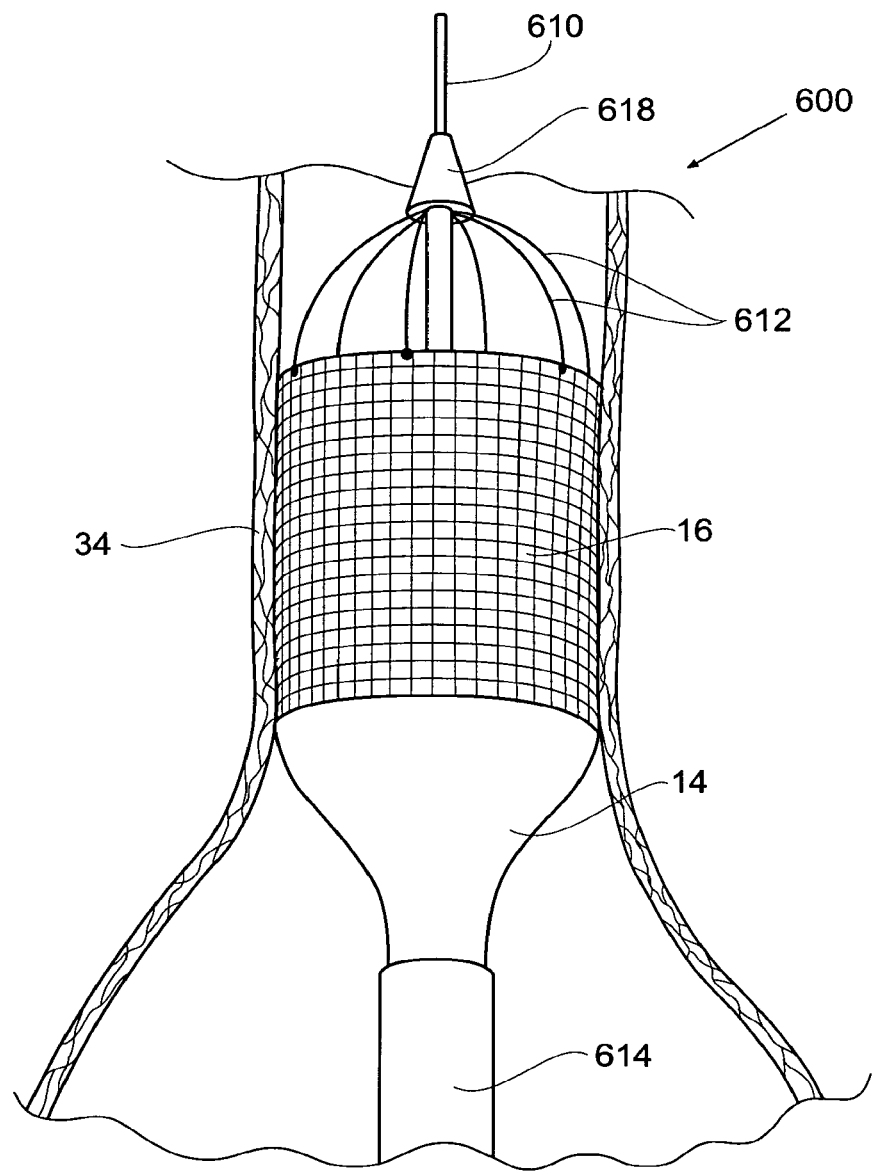
FIG. 40 is an embodiment of a prosthesis delivery catheter for a prostheses in which the stent structure covers only a portion of the prosthesis, the catheter including an array of stabilization struts to help hold the prosthesis in position against the flow of blood.

FIG. 40 shows an embodiment of a prosthesis delivery catheter 600 for a prostheses 14 in which the stent structure 16 covers only a portion of the prosthesis, e.g., being present only at the ends. As shown in FIG. 40, the prosthesis delivery catheter 600 (which is shown deployed over a guidewire 610) includes an array of stabilization struts 612 that are releasably coupled to the stent structure 16 at the end of the prosthesis 14, e.g., by sutures that can be released by pulling on a drawstring (not shown) that passes through a lumen in the catheter 600. The stabilization struts 612 hold the self-expanding stent structure 16 in position against the vessel wall 34, while the remainder of the prosthesis 14 is being deployed (by withdrawal of a delivery sheath 614). The struts 612 support the stent structure 16 (and thus the overall prosthesis 14) against the force of blood flow through the vessel during prosthesis deployment. The catheter 600 can also include a nose cone 618 at its distal end to diffuse blood flow toward the vessel wall, to aid in supporting the prosthesis 14 during its deployment. Upon deployment of the prosthesis 14, the struts 612 can be detached from the stent structure 14 by pulling upon the drawstring to release the sutures, and the catheter 600 is withdrawn over the guidewire 610 through the delivery sheath 614 (the struts 612, freed from the stent structure 16, fold back upon the catheter 600 during passage through the delivery sheath 614).

Figure 41:
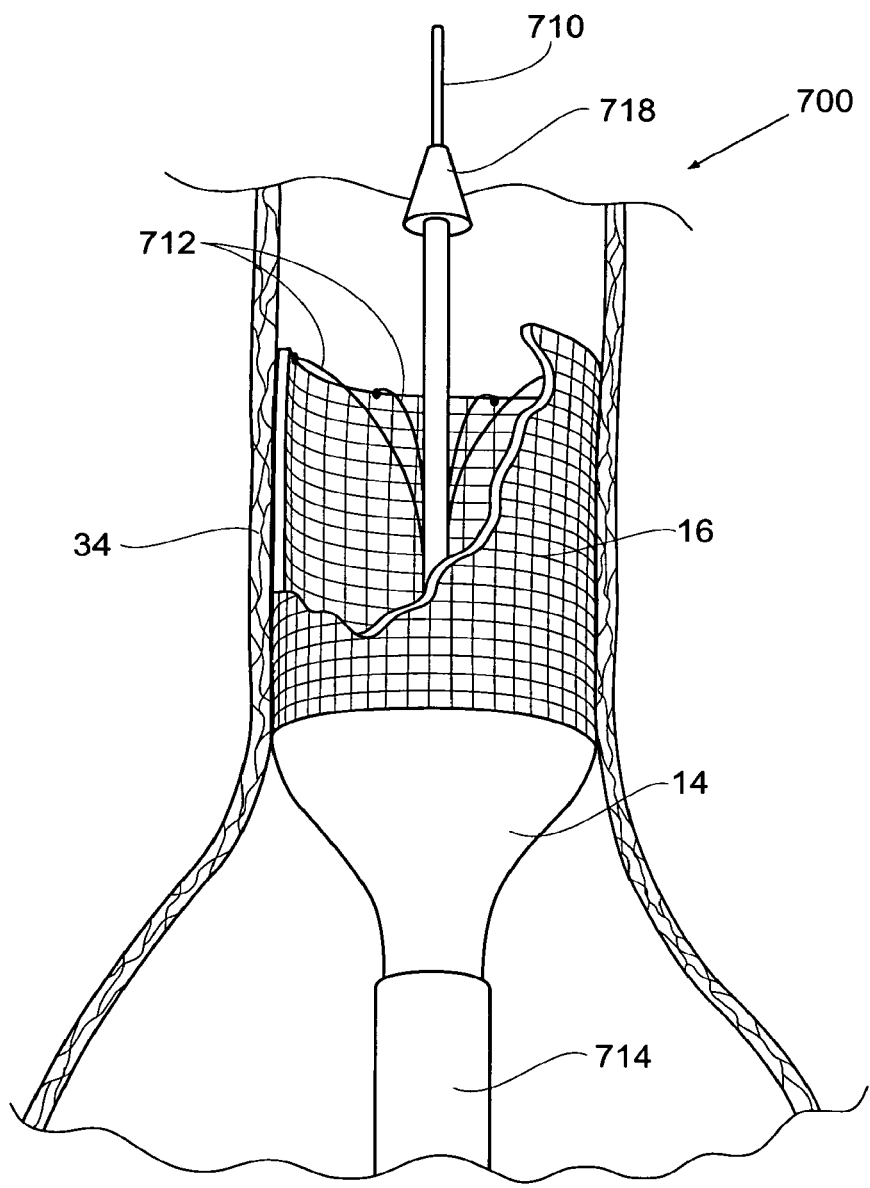
FIG. 41 is another embodiment of a prosthesis delivery catheter for a prostheses in which the stent structure covers only a portion of the prosthesis, the catheter including an array of inverted stabilization struts to help hold the prosthesis in position against the flow of blood.

FIG. 41 shows an alternative embodiment of a prosthesis delivery catheter 700 for a prostheses 14 in which the stent structure 16 covers only a portion of the prosthesis, e.g., being present at the ends. As shown in FIG. 40, the prosthesis delivery catheter 700 (which is also shown deployed over a guidewire 710) includes an array of inverted stabilization struts 712 that are releasably coupled to the stent structure 16 at the end of the prosthesis 14, e.g., by sutures that can be released by pulling on a drawstring (not shown) that passes through a lumen in the catheter 700. The inverted stabilization struts 712, like the struts 612 shown in FIG. 40, hold the self-expanding stent structure 16 in position against the vessel wall 34, while the remainder of the prosthesis 14 is being deployed (by withdrawal of a delivery sheath 714). Like the catheter 600 in FIG. 40, the catheter 700 can also include a nose cone 718 at its distal end to diffuse blood flow toward the vessel wall. Upon deployment of the prosthesis 14, the struts 712 are detached from the stent structure 14 by pulling upon the drawstring not shown), and the catheter 700 is withdrawn over the guidewire 710 through the delivery sheath 714 (the struts 612, freed from the stent structure 16, fold back upon the catheter 600 during passage through the delivery sheath 614).

Figure 42:
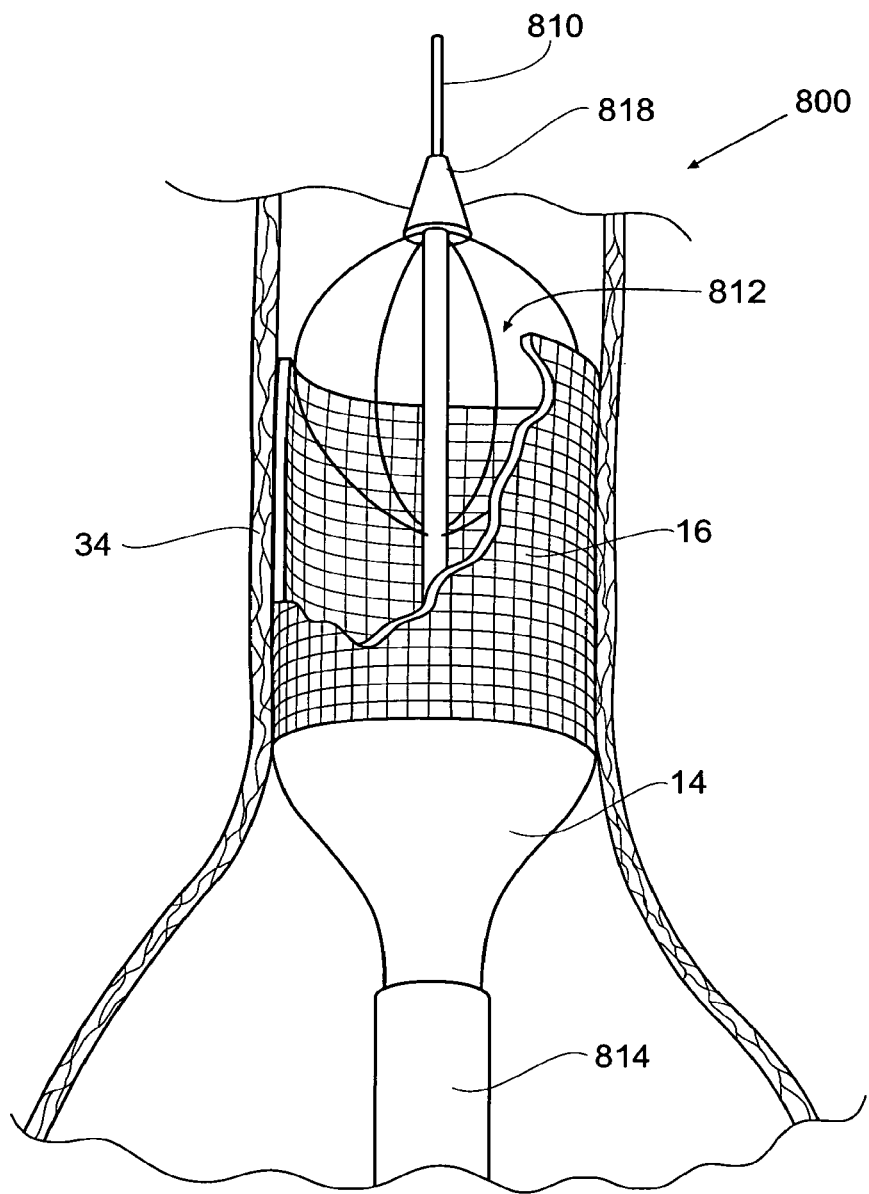
FIG. 42 is another embodiment of a prosthesis delivery catheter for a prostheses in which the stent structure covers only a portion of the prosthesis, the catheter including a stabilization basket to help hold the prosthesis in position against the flow of blood.

FIG. 42 shows another alternative embodiment of a prosthesis delivery catheter 800 for a prostheses 14 in which the stent structure 16 covers only a portion of the prosthesis, e.g., being present at the ends. As shown in FIG. 42, the prosthesis delivery catheter 800 (which is also shown deployed over a guidewire 810) includes a self-expanding stabilization basket 812. The stabilization basket 812 holds the self-expanding stent structure 16 in position against the vessel wall, while the remainder of the prosthesis 14 is being deployed (by withdrawal of a delivery sheath 814). Like the catheters 600 and 700 in FIGS. 40 and 41, the catheter 800 can also include a nose cone 818 at its distal end to diffuse blood flow toward the vessel wall. Upon complete deployment of the prosthesis 14, the stabilization basket can be placed into a collapsed condition by withdrawal through the delivery sheath 814, as the catheter 800 is withdrawn over the guidewire 810.

In all of the just-described embodiments, if the prosthesis 14 has been fully deployed prior to the introduction of the fasteners 28, and/or the prosthesis delivery catheter 600, 700, or 800 has been withdrawn from the targeted site, the guidewire 610, 710, 810 can be subsequently used to deploy a fastener attachment assembly for the prosthesis 14 to the targeted site, as will be described in greater detail next. Alternatively, if the prosthesis 14 has not been fully deployed at the time the fasteners 28 are applied—or if, for whatever reason, withdrawal of the prosthesis delivery catheter 600, 700, or 800 is not desired—the prosthesis delivery catheter 600, 700, or 800, and its respective guidewire 610, 710, or 810, can be retained at the targeted site, while a fastener attachment assembly for the prosthesis 14 is introduced into the targeted site over a separate guidewire from another body access point. In this arrangement, deployment of the prosthesis 14 and/or withdrawal of the prosthesis delivery catheter 600, 700, or 800 can be completed after the fasteners 28 have been applied.

II. Fastening the Prosthesis

In a desired embodiment, a fastener attachment assembly is provided that makes possible intraluminal fastener attachment. The attachment assembly can be variously constructed.

A. Two Component Fastener Guide and Attachment Assembly

In one arrangement, the fastener attachment assembly comprises a fastener guide or directing component 18 and a fastener applier component 27. The guide component 18 desirably has a steerable or deflectable distal tip, which is initially deployed over the guidewire 12. In use in the illustrated embodiment, the guidewire 12 that is used to deliver and position the prosthesis 14 remains within the vessel for subsequent deployment of the fastener guide component 18. Alternatively, another guidewire from a different body access point can be used for deployment of the fastener guide component 18. In either arrangement, the fastener applier component 27 is desirably deployed through the guide component 18 after removal of the guidewire over which the guide component 18 has been delivered. The fastener applier 27 carries at least one fastener 28 and a fastener drive mechanism 100 for advancing the fastener 28, so that it penetrates the prosthesis 14 and underlying vessel wall, to thereby anchor the prosthesis 14 firmly in place.

1. Fastener Directing Component

Figure 6:
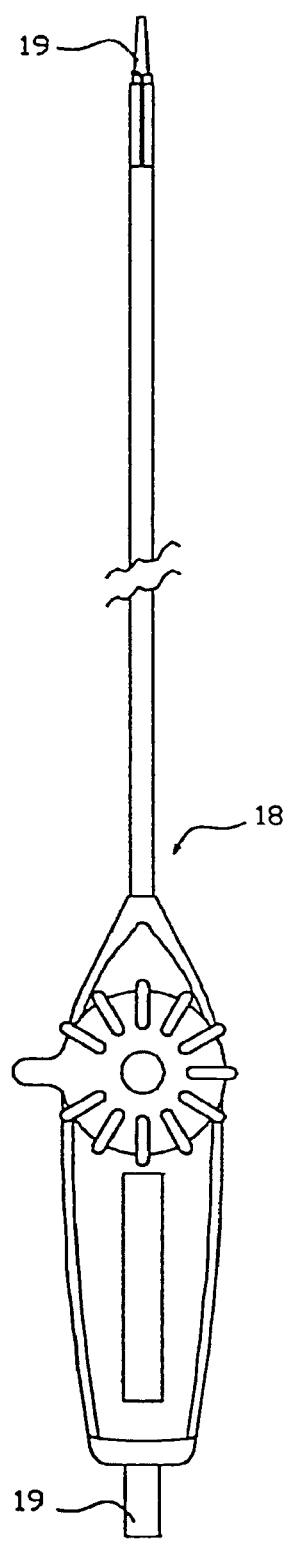
FIG. 6 is a perspective view showing one embodiment of a device for directing the fastener applier.
Figure 7:
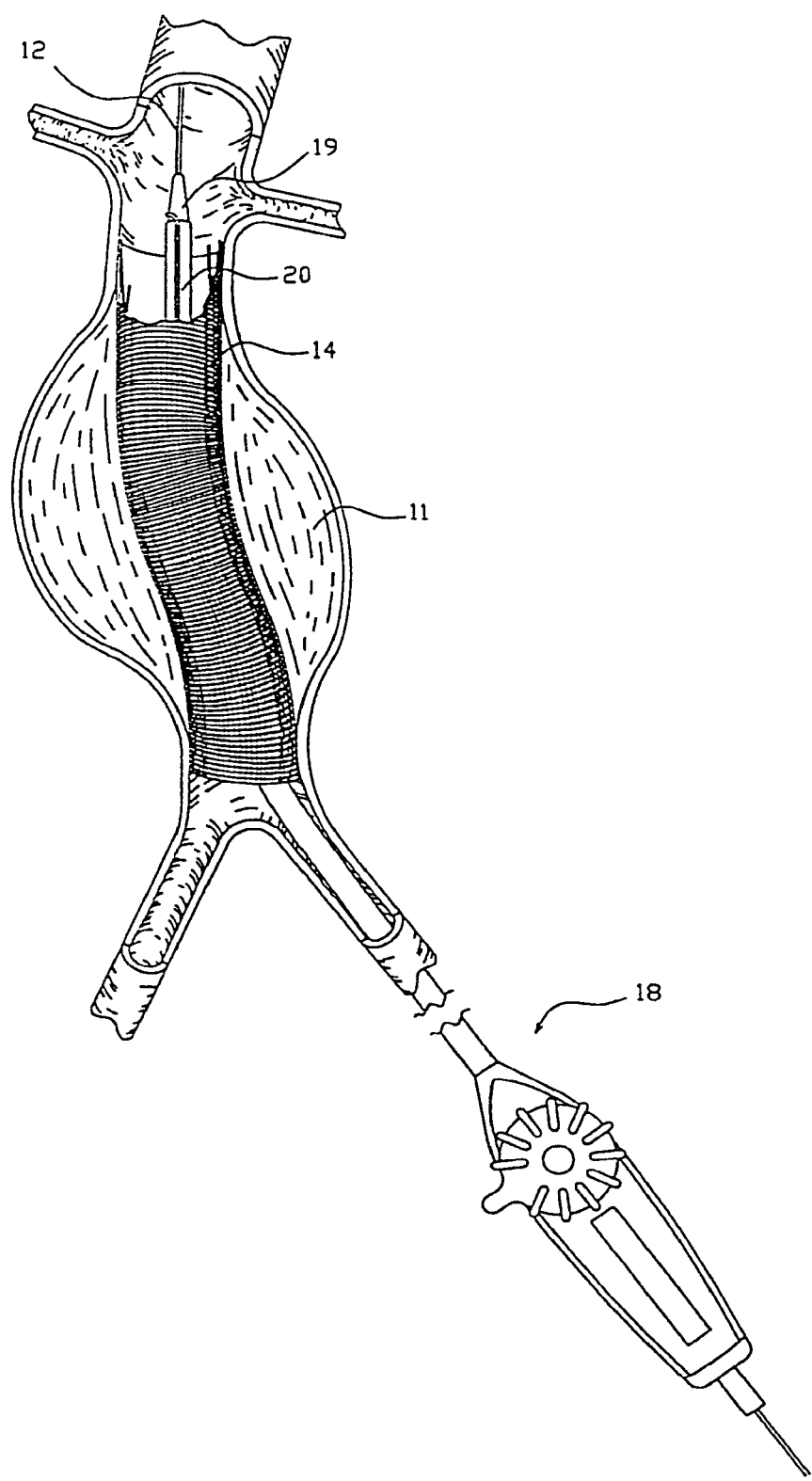
FIG. 7 is a perspective view showing the device of FIG. 6 upon insertion within the deployed endovascular graft of FIG. 3 with both the graft and scaffolding broken away.

FIG. 6 depicts one embodiment of the directing or guide component 18 that forms a part of the fastener attachment assembly. The component 18 includes an interior lumen that accommodates passage of an obturator 19. The obturator 19 has a lumen to allow for delivery of the directing component 18 over the guidewire 12, as shown in FIG. 7. Once deployed in a desired location, the obturator 19 and guidewire 12 are removed, leaving the central lumen open for passage of the fastener applier component 27, as will be described later.

Figure 8:
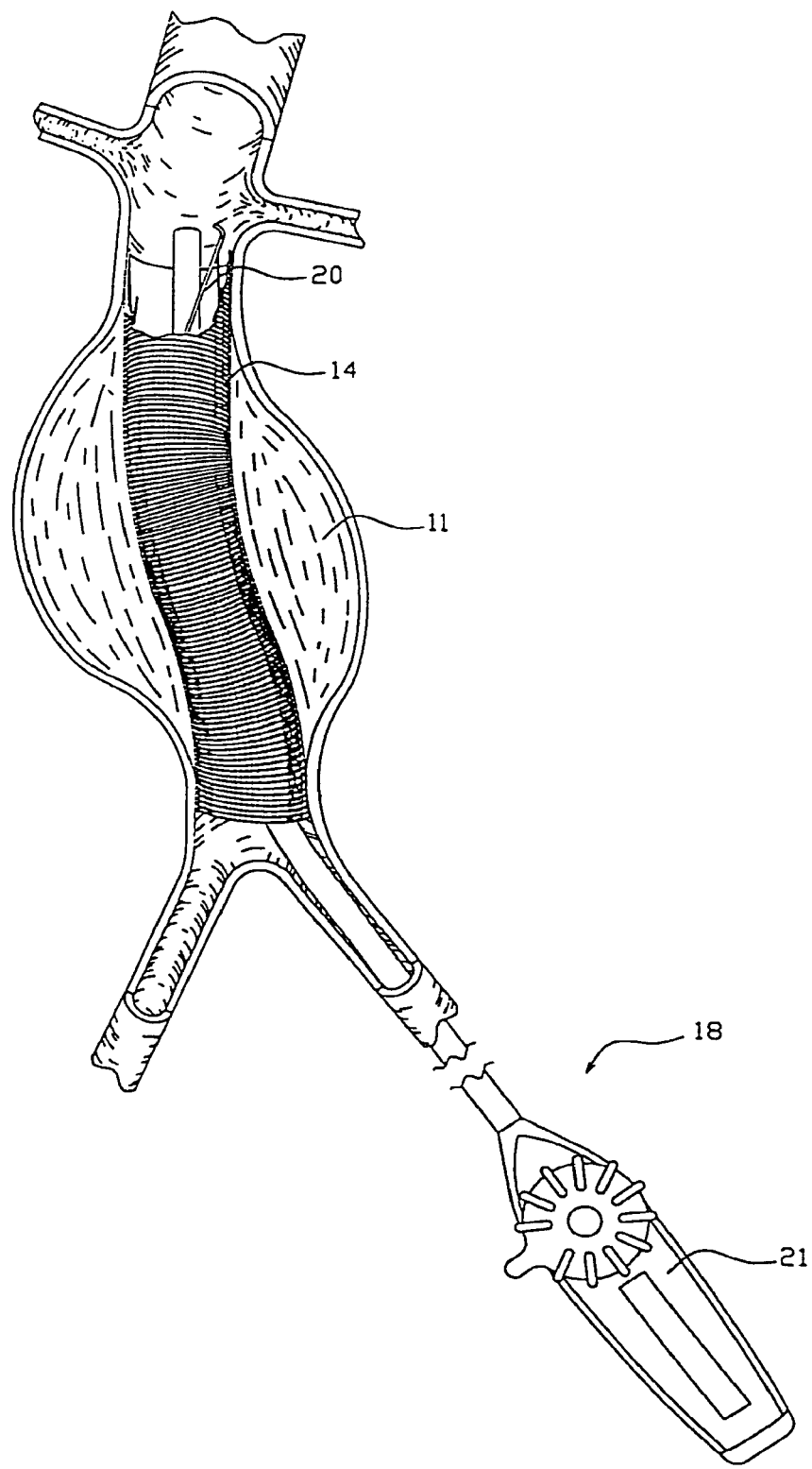
FIG. 8 is a perspective view of the device of FIG. 6 showing activation of one embodiment of a stabilizing device attached to the directing device.
Figure 9:
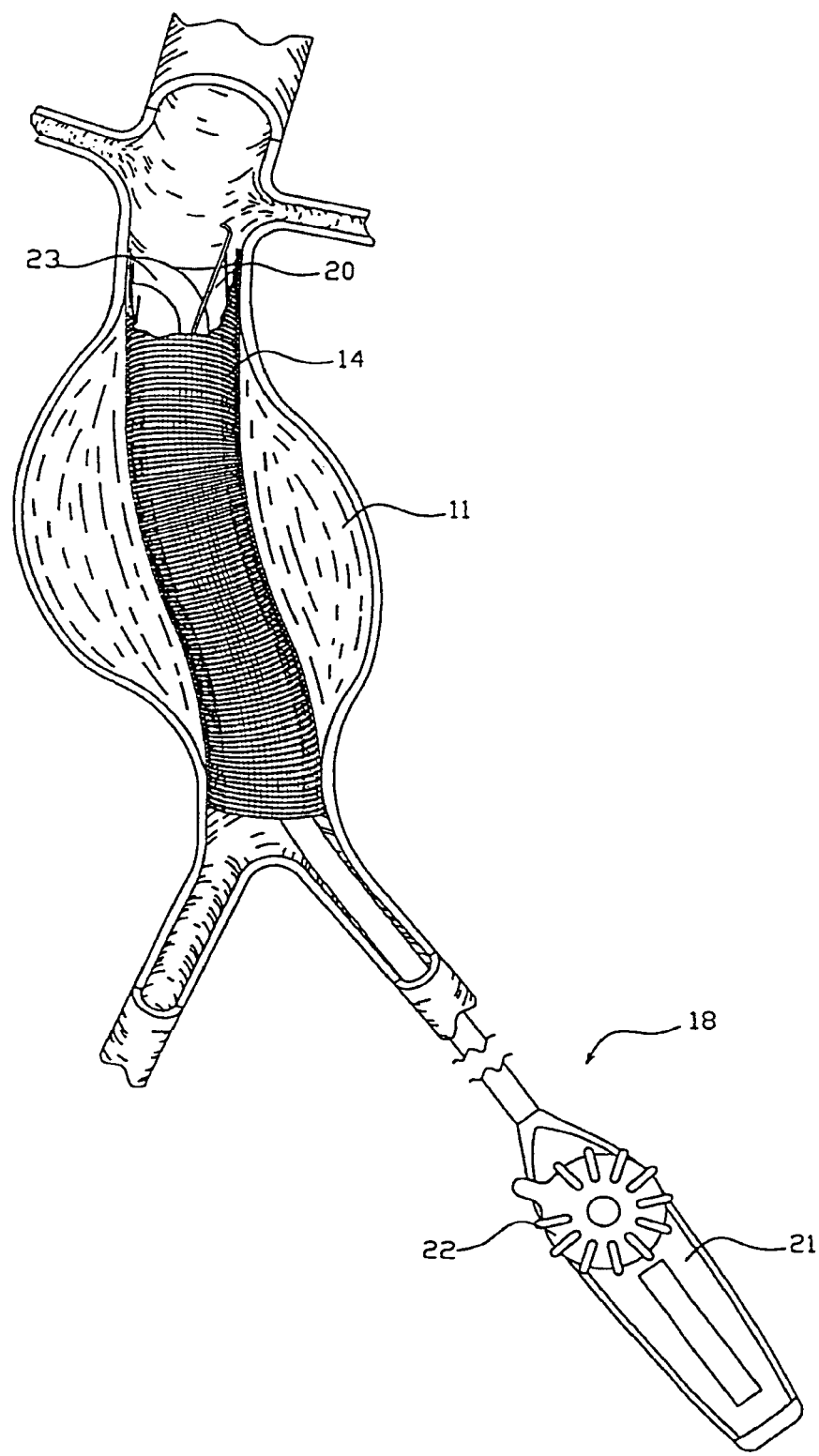
FIG. 9 is a perspective view of the control assembly in FIG. 8 articulating the directing device of FIG. 6.

In the illustrated embodiment (see FIG. 8), the directing component 18 includes a control assembly 21. In one embodiment the control assembly 21 features a movable wheel or lever 22, which operate interior steering wires in a conventional fashion to deflect the distal tip 23 of the directing component 18 toward a desired location, as seen in FIG. 9. It is contemplated that the control assembly 21 for the directing component 18 could be activated mechanically, electrically, hydraulically or pneumatically. The control assembly 21 has a through lumen to allow for the passage of the obturator 19 (as just described) and the fastener applier component 27, as will be described next.

2. Fastener Applier Component

Figure 14A:
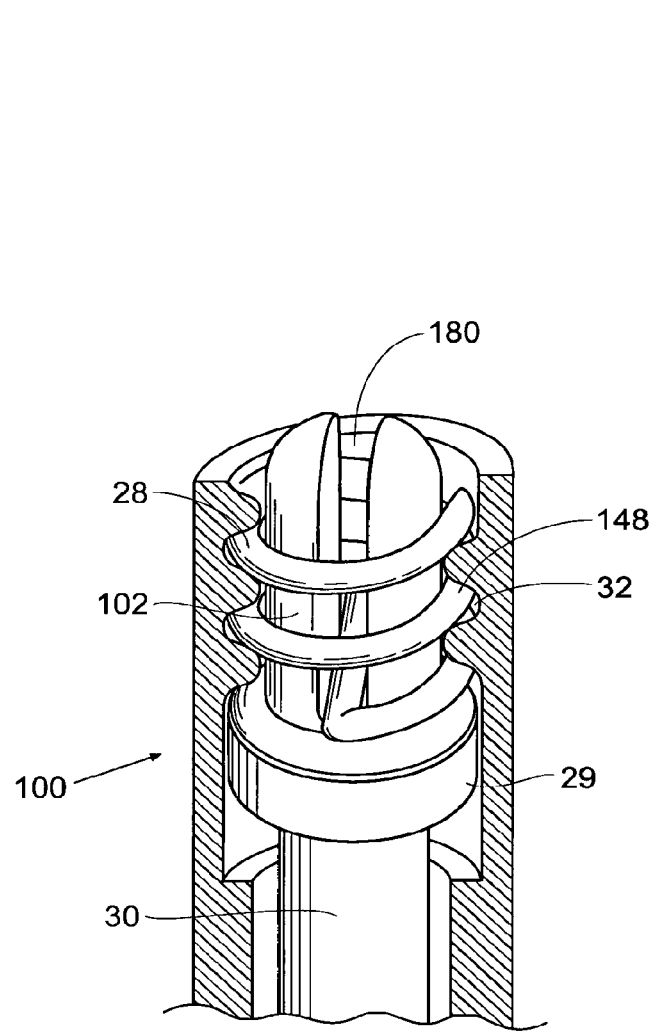
FIG. 14A is an enlarged view of the distal end of the fastener applier shown in FIG. 14, showing the details of the fastener drive mechanism.
Figure 14:
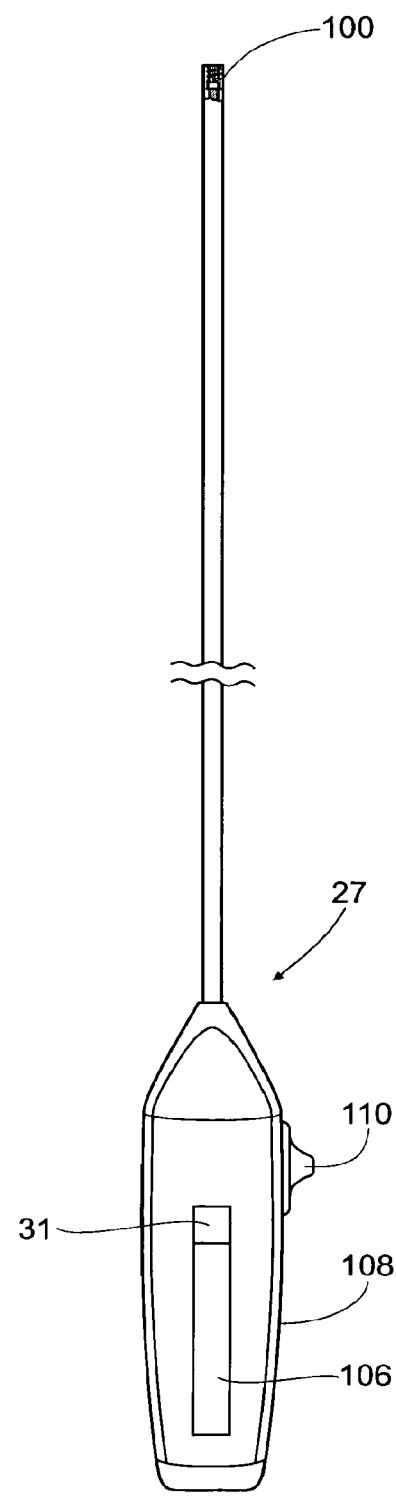
FIG. 14 is one embodiment of the fastener applier.
Figure 15:
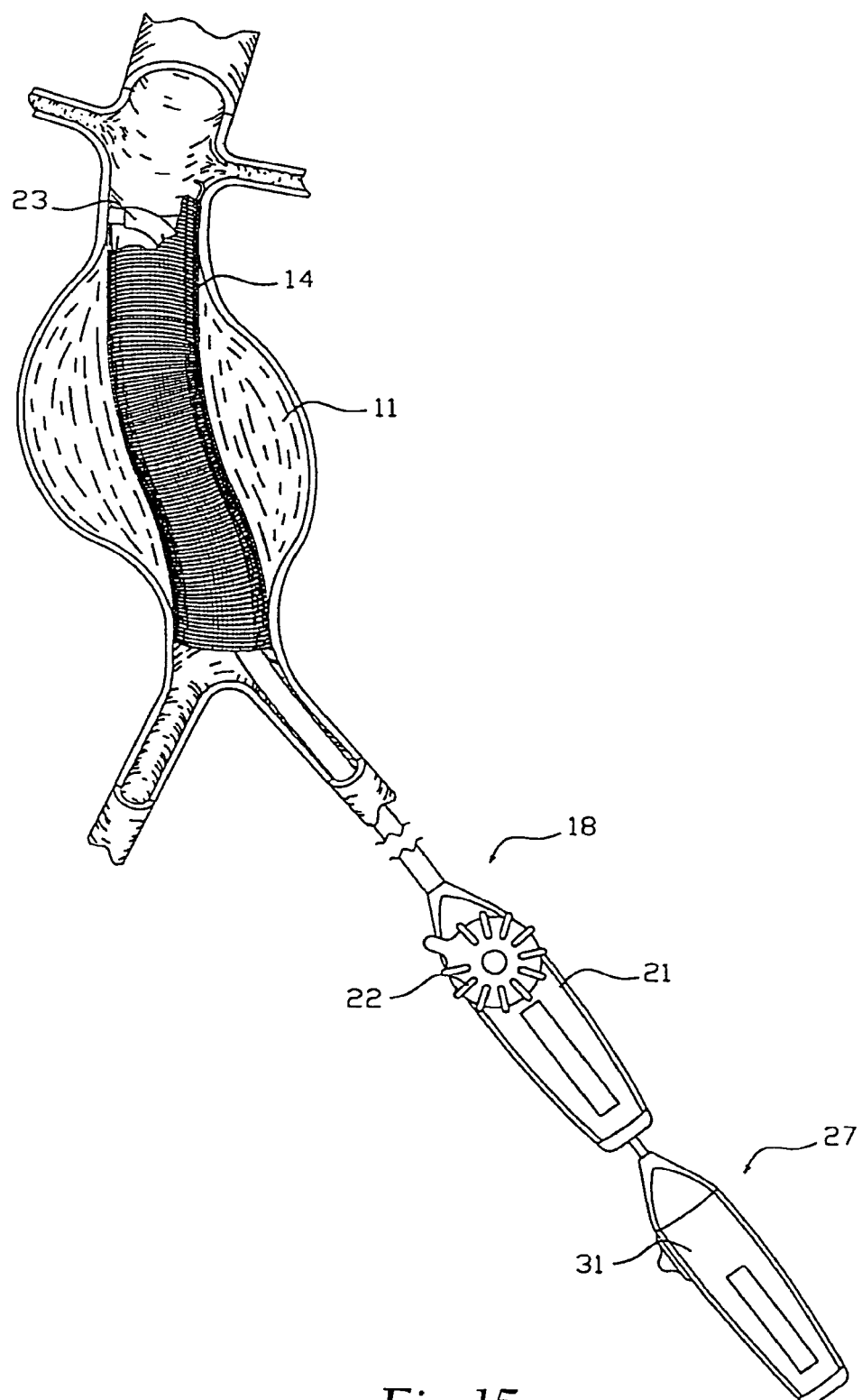
FIG. 15 is a perspective view of the fastener applier of FIG. 14 being positioned within directing device of FIG. 6.

FIG. 14 shows one embodiment of the fastener applier component 27 that forms a part of the fastener attachment assembly. As FIG. 15 depicts, the fastener applier component 27 is deployed through the central lumen of the directing component 18 to the site where a fastener 28 will be installed.

Located at the distal end of the fastener applier component 27 (see FIG. 14) is a fastener drive mechanism 100. In the illustrated embodiment (see FIG. 14A), the drive mechanism 100 includes a driver 29 that is coupled to a carrier 102. The coupling between the driver 29 and carrier 102 can take different forms—e.g., magnets, graspers, or other suitable mechanical connection. In the embodiment illustrated in FIG. 14A, the driver 29 and carrier 102 are integrally connected as a single unit.

Figure 18:
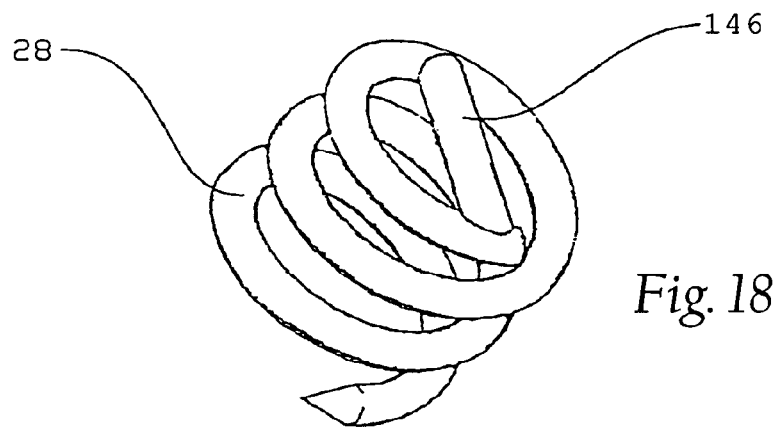
FIG. 18 is a enlarged perspective view of one embodiment of the helical fastener of FIG. 16.

The carrier 102 is sized and configured to engage a selected fastener 28. In FIG. 14A, the fastener takes the form of a helical fastener of the type shown in FIGS. 18 and 27.

Figure 26A:
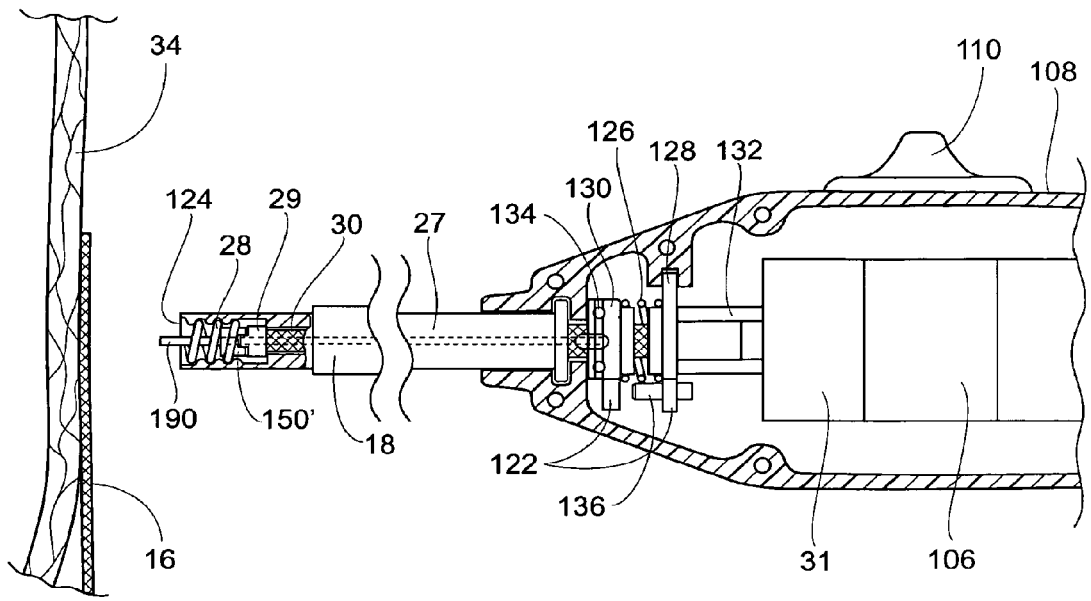
FIG. 26A is an enlarged section view of the drive mechanism of the fastener applier shown in FIGS. 25A and 25B showing a contact/force sensing assembly that disables the applier in the absence of desired contact between the fastener and a targeted tissue region.
Figure 26B:
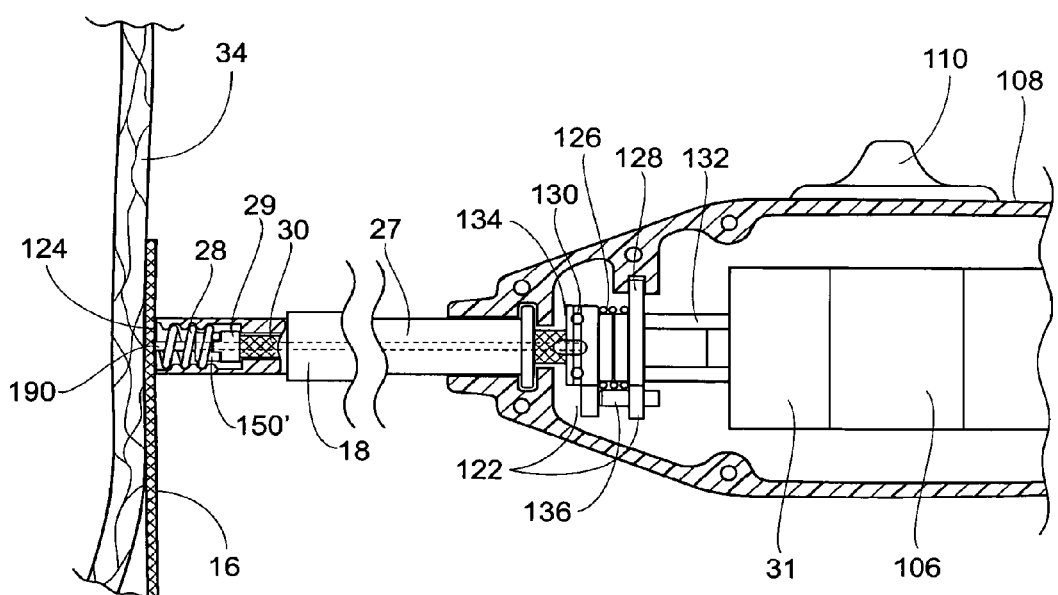
FIGS. 26B and 26C are enlarged section views of the drive mechanism of the fastener applier shown in FIGS. 25A and 25B, showing the contact/force sensing assembly enabling use of the applier in response to desired contact between the fastener and the targeted tissue region.
Figure 26C:
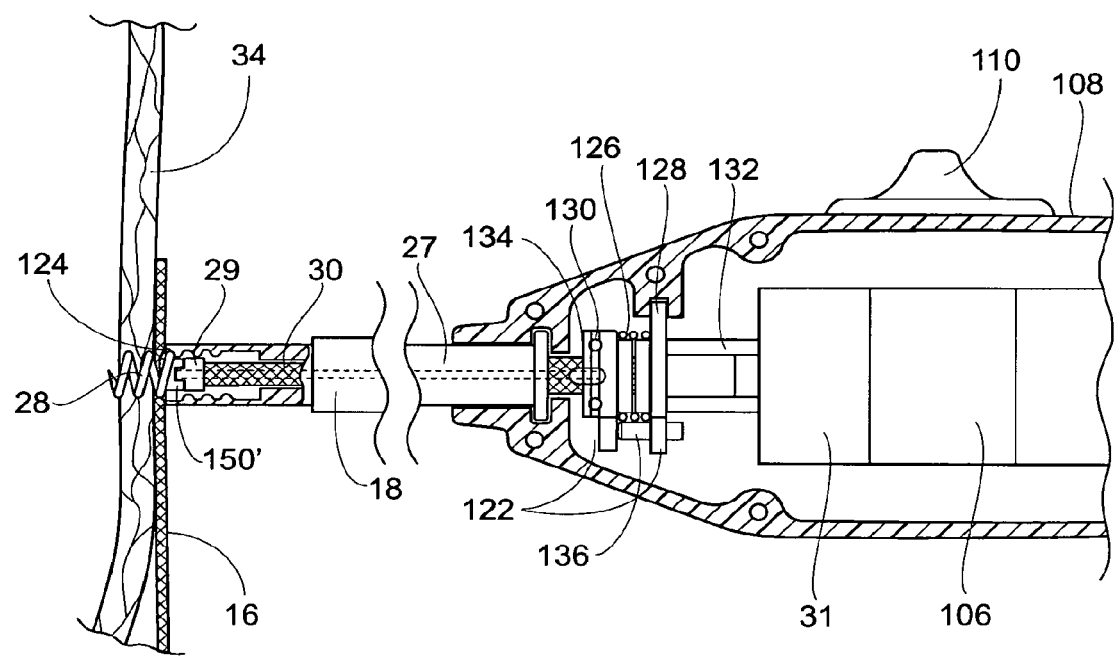
Figure 27:
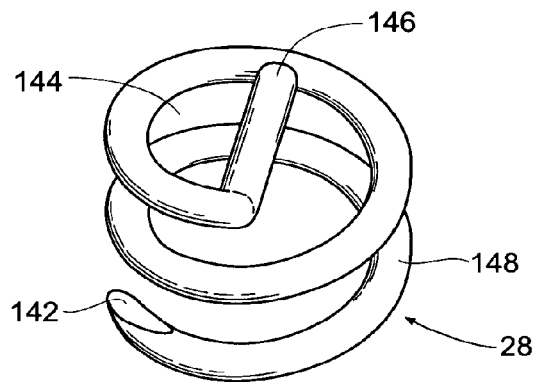
FIG. 27 is a perspective view of a helical fastener that can be used in association with the fastener applier shown in FIGS. 14, 23, and 24.

As best shown in FIG. 27, and as will be described in greater detail later, the helical fastener 28 in FIG. 26 is an open coil 148 with a sharpened leading tip 142. The proximal end 144 of the fastener 28 includes an L-shaped leg 146. The L-shape leg 146 desirably bisects the entire interior diameter of the coil 148; that is, the L-shaped leg 146 extends completely across the interior diameter of the coil 148, as FIG. 27 shows. The L-shaped leg 146 serves to engage the carrier 102 of the fastener applier 27, which rotates the helical fastener to achieve implantation. The L-shaped leg 146 also serves as a stop to prevent the helical fastener from penetrating too far into the tissue.

The carrier 102 in FIG. 14A includes a slot 180, which receives the L-shaped leg 146 to couple the fastener 28 for rotation with the carrier 102. The turns of the coil 148 rest in complementary internal grooves 32 that surround the carrier 102. The grooves 32 could be positioned along the entire length of the fastener 28 or within a portion of its length.

The actuation of the drive mechanism 100 can, of course, be accomplished in various ways, e.g., mechanical (i.e., manual or hand-powered), electrical, hydraulic, or pneumatic. In the illustrated embodiment (see FIG. 14B), a drive cable 30 couples the fastener driver 29 to an electric motor 106 carried in the applier handle 108. The drive cable 30 is desirably made of a suitable material that allows for both bending and rotation. Driven by the motor 106 (which is, in turn, under the control of motor control unit 31, as will be described later), the drive cable 30 rotates the driver 29 and, with it, the carrier 102. The carrier 102 imparts rotation and torque to the helical fastener 28 for implantation in tissue.

Figure 16:
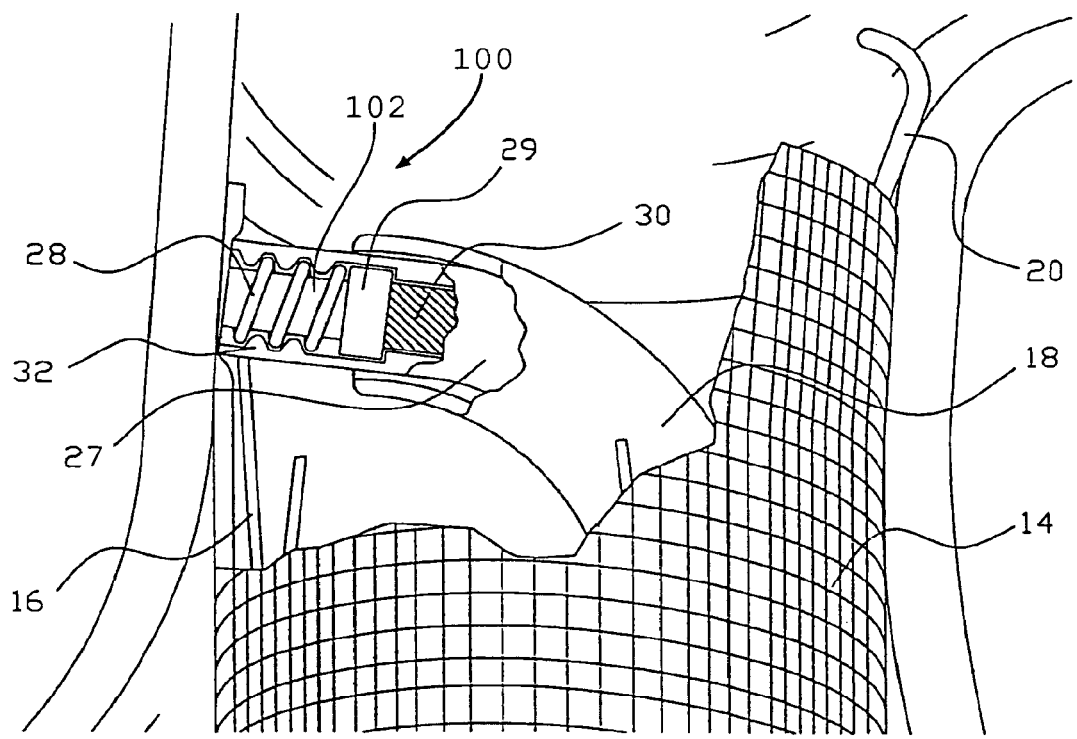
FIG. 16 is an enlarged cross-sectional view of one embodiment of the fastener applier of FIG. 14.
Figure 17:
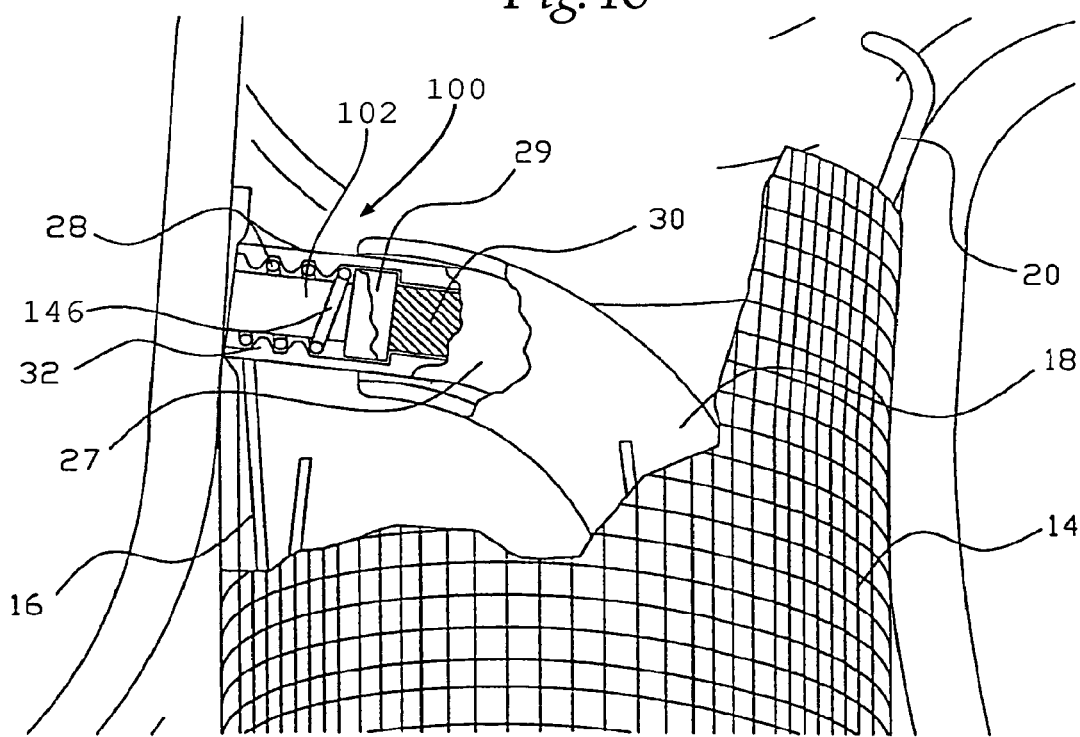
FIG. 17 is an enlarged cross-sectional view of the attachment applier showing one embodiment of the proximal end of the helical fastener and the drive mechanism.
Figure 19:
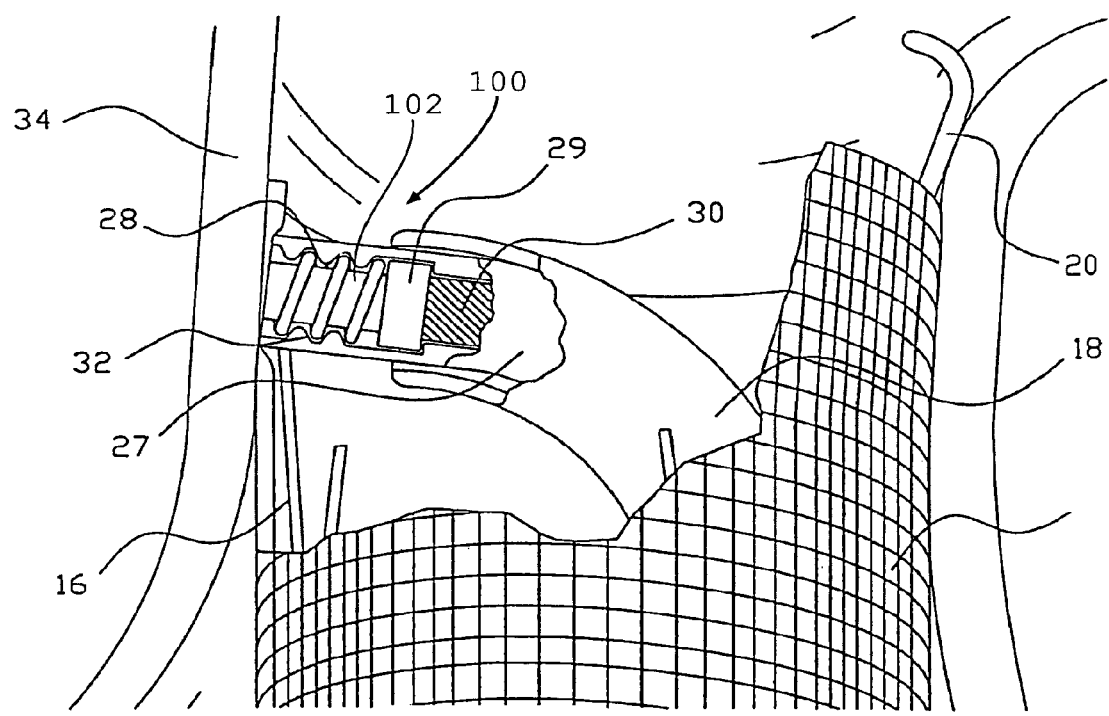
FIG. 19 is an enlarged view of the attachment applier showing one embodiment of the control assembly that activates the fastener applier.
Figure 20:
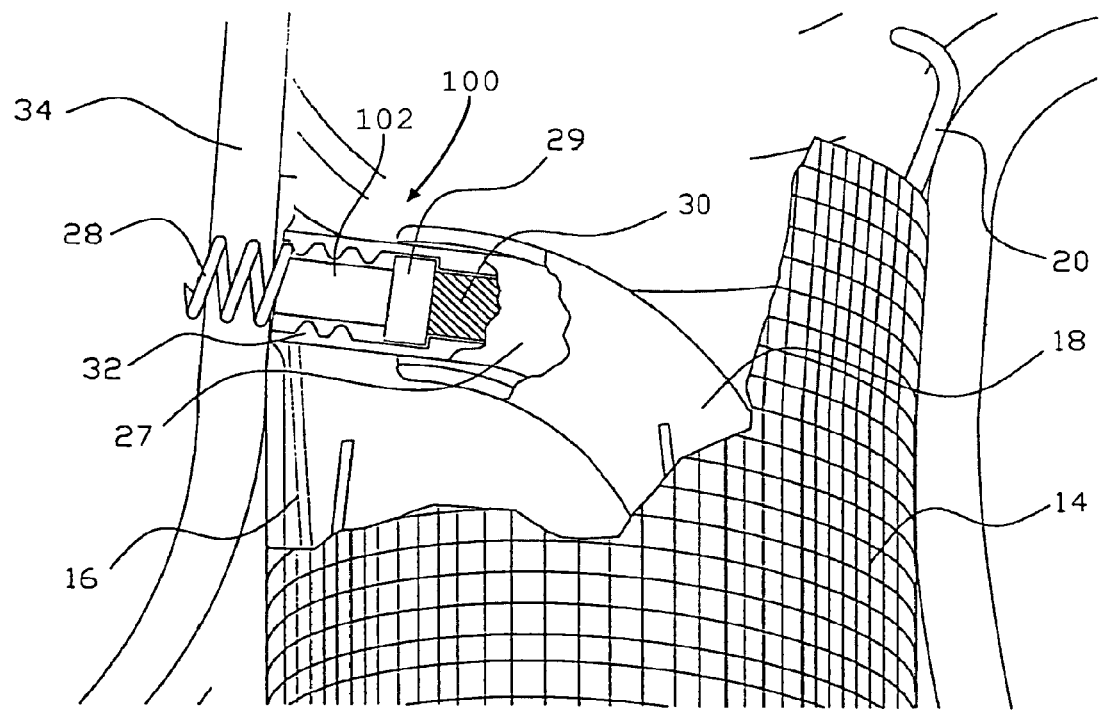
FIG. 20 is an enlarged view of the attachment applied activated with a fastener implanted into the graft and vessel wall.
Figure 21:
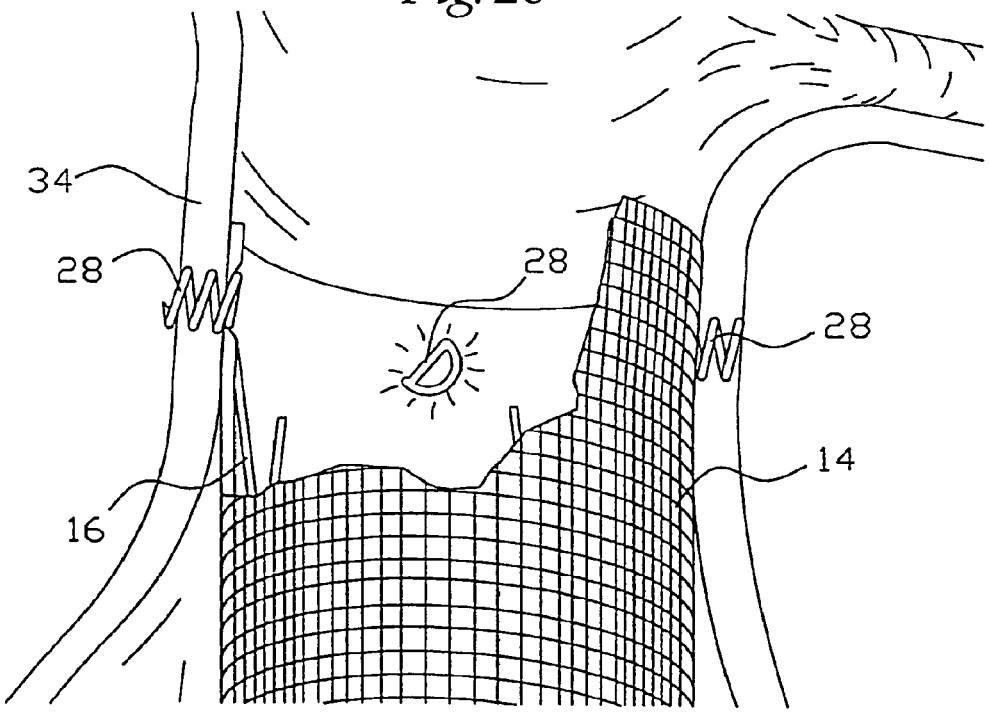
FIG. 21 is an enlarged view of the completed attachment of the proximal graft of FIG. 3 to the vessel wall with fasteners.

FIG. 16 is an enlarged cross-sectional view of fastener applier 27 and directing device 18. FIG. 17 is an enlarged cross-sectional view of the fastener applier with a cross-section of the fastener driver 29 depicting the engagement between the fastener driver 29 and helical fastener 28. FIG. 19 depicts the fastener applier 27 during activation of the fastener drive mechanism 100. Activation of the drive mechanism 100 rotates, as a unit, the drive shaft 30, the driver 29, the carrier 102, and helical fastener 28. This rotation causes the helical fastener 28 to travel within the internal grooves 32 of the fastener applier and into the prosthesis 14 and vessel wall 34 (see FIG. 20). FIG. 21 illustrates a completed helical fastener 28 attachment of the graft 14 to the vessel wall 34.

In use, the applier component 27 is advanced through the directing component 18 and into contact with the prosthesis. The operator actuates the control unit 31 by contacting a control switch 110 (see FIGS. 14 and 14B). This action causes the helical fastener 28 to be rotated off the carrier 102 and through the prosthesis 14 and into the vessel wall 34. The motor control unit 31 desirably rotates the drive cable 30 a specific number of revolutions with each activation command. This can be accomplished by incorporating a mechanical or electrical counter.

With the deployment of a fastener 28, the fastener applier component 27 is retrieved through the directing component 18, and another fastener 28 is loaded into the carrier 102. The directing component 18 is repositioned, and the applier component 27 is advanced again through the directing component 18 and into contact with the prosthesis 14. The operator again actuates the control unit 31 by contacting the control switch 110 to deploy another fastener 28. This process is repeated at both proximal and/or distal ends of the prosthesis 14 until the prosthesis 14 is suitably attached and sealed to the vessel wall 34. It is contemplated that from about two to about twelve fasteners 28 may be applied at each end of the prosthesis 14 to affect anchorage. The fasteners 28 can be applied in a single circumferentially space-apart row, or may be applied in more than one row with individual fasteners being axially aligned or circumferentially staggered.

Figure 22:
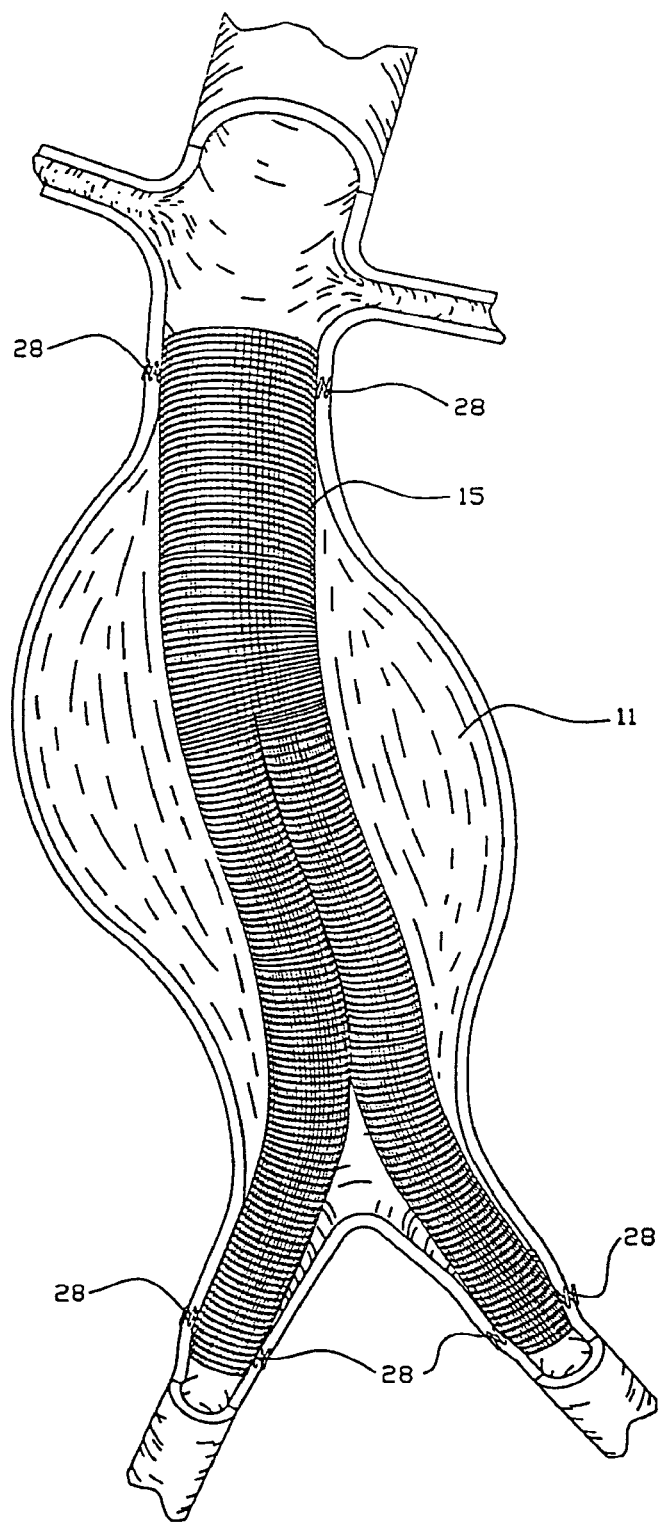
FIG. 22 is a perspective view of the graft of FIG. 4 completely attached to the vessel.

FIG. 22 illustrates a perspective view of a graft prosthesis attached to the vessel wall both proximally and distally. It is contemplated that the present invention can be used for graft attachment of both straight and bifurcated grafts within the aorta and other branch vessels.

Figure 25A:
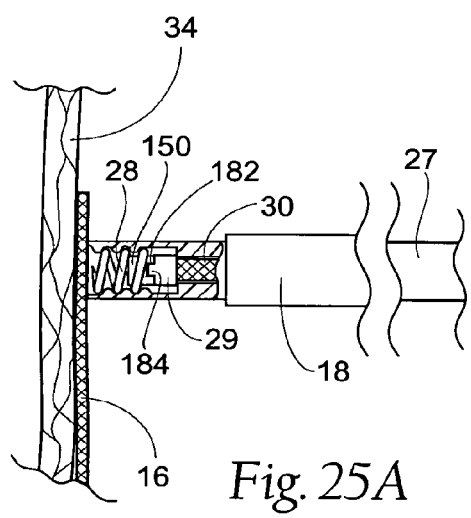
FIGS. 25A and 25B are enlarged views of the distal end of a fastener applier showing the details of an alternative embodiment of the fastener drive mechanism.
Figure 25B:
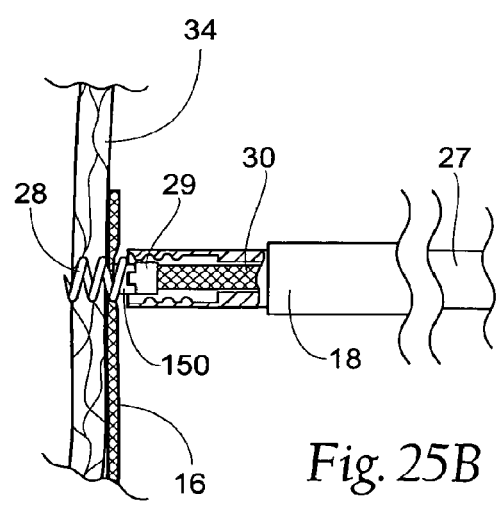
Figure 28A:
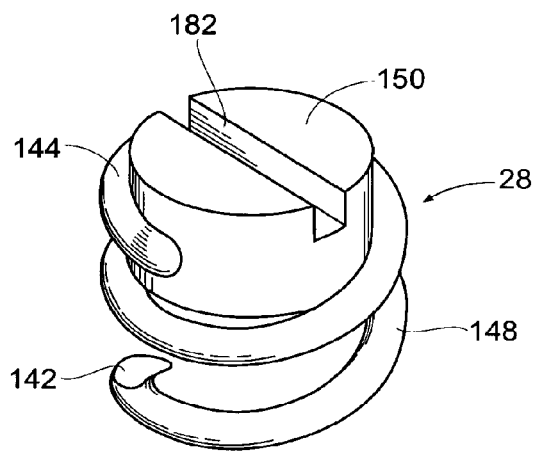
FIG. 28A is a perspective view of a helical fastener that can be used in association with the fastener applier shown in FIGS. 25A and 25B.

An alternative embodiment of the drive mechanism 100 is shown in FIGS. 25A and 25B. In this embodiment, the driver 29 is coupled to a carrier 150, which forms a part of the helical fastener 28 itself, as also shown in FIG. 28A. As shown in FIG. 28A, the helical fastener 28 is, like the fastener shown in FIG. 27, an open coil 148 with a sharpened leading tip 142. The proximal end 144 of the fastener 28 includes the carrier 150.

The carrier 150 includes a slot 182. The slot 182 engages a drive flange 184 on the driver 29 (see FIG. 25A) to impart rotation of the driver 29 to rotation of the helical fastener 28 during the implantation process. Like the L-shaped leg of the fastener shown in FIG. 27, the carrier 150 also serves as a stop to prevent the helical fastener from penetrating too far into the tissue.

The coupling engagement between the carrier 150 and the driver 29 could be accomplished in various ways, e.g., by separate graspers or grippers, a magnetic couple, or any other suitable mechanical connecting means. In the illustrated embodiment, the driver 29 is made of a magnetized material, and the carrier 150 is made from a material that is magnetically attracted toward the magnetized material. Of course, a reverse arrangement of magnetized and magnetically attracted materials could be used.

In this arrangement, the motor coupling 132 between the drive cable 30 and the motor 106 accommodates axial displacement of the motor cable 30 (left and right in FIGS. 25A and 25B) without interrupting the drive connection with the motor 106. With the distal tip of the applier device 27 in contact with the prosthesis 14 (see FIG. 25A), the operator actuates the control unit 31 by contacting a control switch 110. The control unit 31 commands the motor 106 to rotate the drive cable 30 to impart rotation to the driver 29 and the magnetically attached helical fastener 28. This action causes the magnetically attached helical fastener 28 to be rotated into prosthesis 14 and the vessel wall 34 (see FIG. 25B). Due to the magnetic coupling, as the fastener 28 is deployed to the left in FIG. 25B, the driver 29 moves in tandem with carrier 150 (also to the left in FIG. 25B). Due to the magnetic coupling between the carrier 150 and the driver 29, the operator must exert a deliberate separation force to decouple the carrier 150 (and, with it, the fastener 28) from the driver 29. This arrangement prevents inadvertent release of a fastener 28.

As before described, with the deployment of a fastener 28, the applier component 27 is retrieved through the directing device 18, and another fastener 28 is magnetically coupled to the driver 29. The directing component 18 is repositioned, and the applier component 27 is advanced again through the directing component 18 and into contact with the prosthesis 14. The operator again actuates the control unit 31 by contacting a control switch 110 to deploy another fastener 28. This process is repeated at both proximal and/or distal ends of the prosthesis 14 until the prosthesis 14 is suitably attached and sealed to the vessel wall 34.

As indicated in the above description, the outer diameter of the applier component 27 is desirably sized and configured to pass through the lumen of the directing component 18, which can take the form of a suitable steerable guide catheter, to direct the applier component 27 to the desired location. As also above described, the applier component 27 is desirably configured to implant one fastener 28 at a time (a so-called "single fire" approach). This is believed desirable, because it reduces the complexity of the design and accommodates access of the applier component 27 through tortuous anatomy. A fastener applier component 27 which carries a single fastener can have a lower profile and may be more effective and less traumatic than fastener appliers which carry multiple fasteners. Still, in alternative embodiments, the applier component 27 may, if desired, be configured to carry multiple fasteners. Moreover, the fastener applier 27 may simultaneously deploy multiple fasteners in the preferred circumferentially spaced-apart space pattern described above.

3. Force Resolution

Penetration and implantation of the fastener 28 into tissue using the applier component 27 requires the applier component 27 to exert an implantation force at or near the prosthesis 14 and vessel wall 34. In the illustrated embodiment, the applier component 27 comprises a driven member for implanting a helical fastener. However, the applier component 27 can comprise virtually any actuated member for exerting an implantation force using, e.g., ultrasonic, laser, or impact concepts.

Regardless of the particular way that the implantation force is generated, the implantation force of the applier component 27 is desirably resolved in some manner to provide positional stability and resist unintended movement of the applier component 27 relative to the implantation site. Stated differently, a resolution force is desirably applied to counteract and/or oppose the implantation force of the applier component 27. It is desirable to resolve some or all or a substantial portion of the implantation force within the vessel lumen (or other hollow body organ) itself, and preferably as close to the implantation site as possible.

The tubular body of the directing component 18 and/or the shaft of the fastener applier component 27 can be sized and configured to possess sufficient column strength to resolve some or all or at least a portion of the implantation force within the vessel lumen or hollow body organ. In addition, or alternatively, the directing component 18 and/or the fastener applier component 27 can include stabilization means 20 for applying a counteracting force at or near the driven member of the fastener applier component 27 that implants the fastener.

Figure 10:
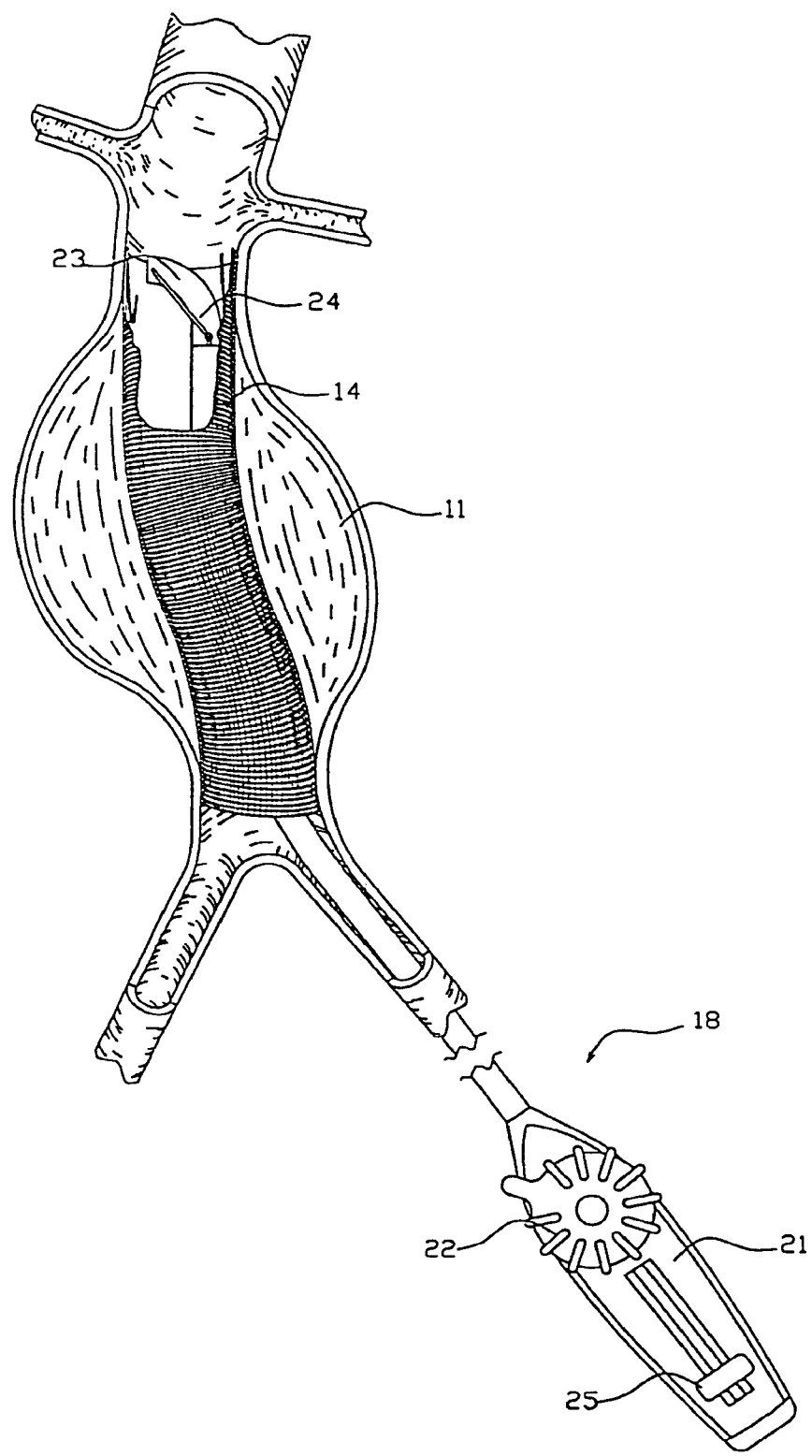
FIG. 10 is a perspective view of an alternative embodiment of the stabilization device of FIG. 8.
Figure 11:
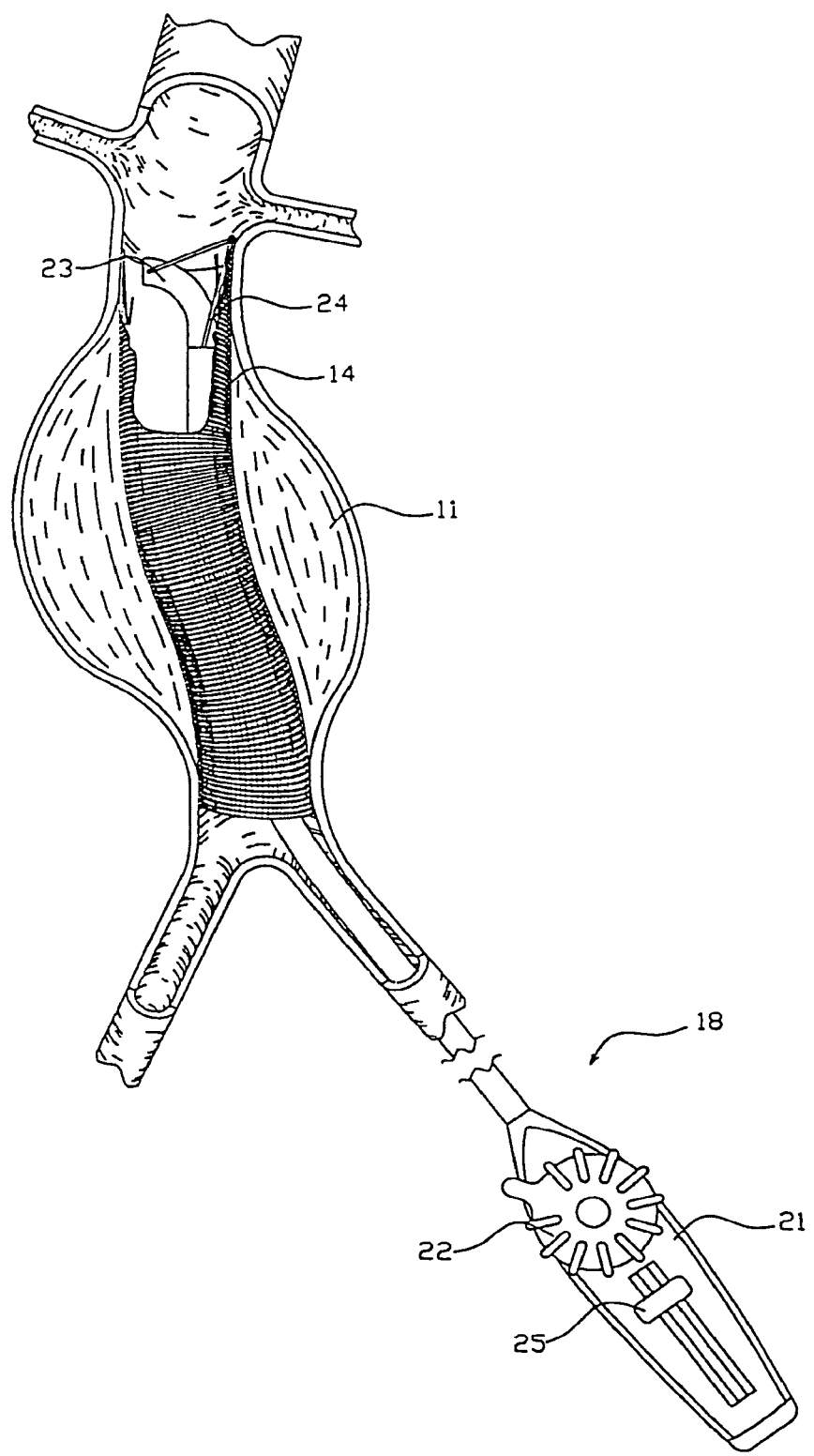
FIG. 11 is a perspective view showing the activation of the alternative stabilization device of FIG. 10.
Figure 12:
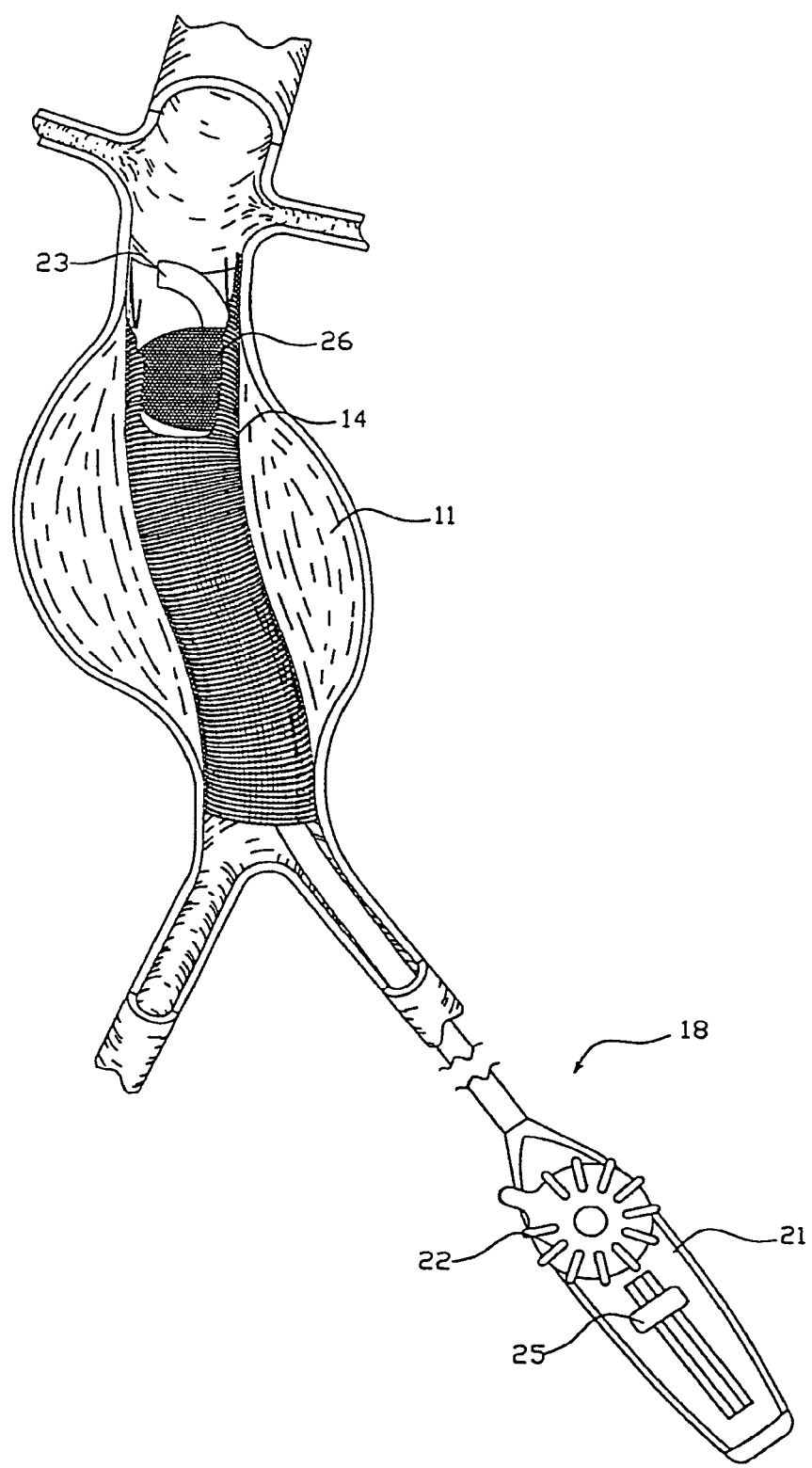
FIG. 12 is a perspective view showing another embodiment of the stabilization device of FIG. 8.
Figure 13:
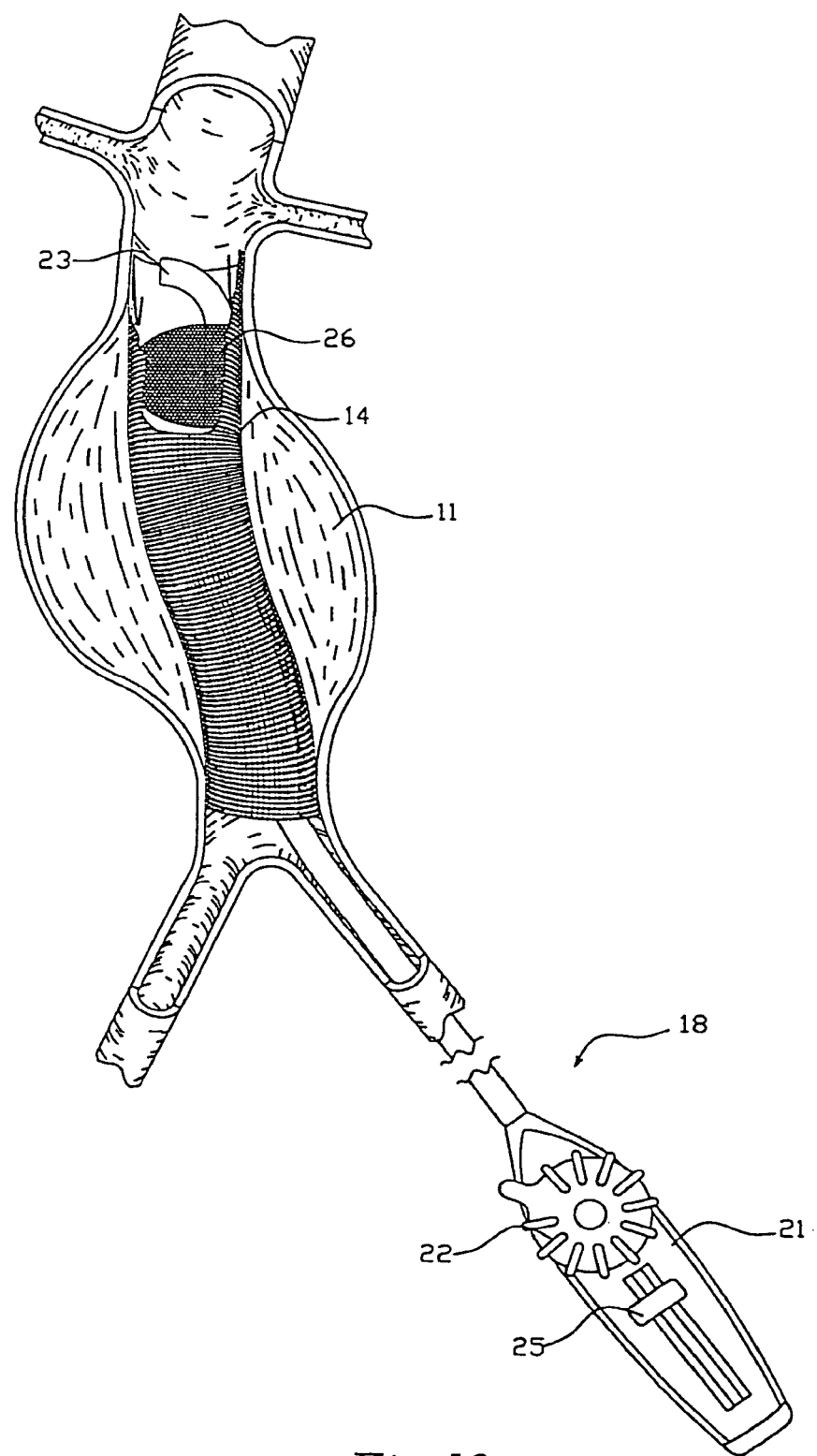
FIG. 13 is a perspective view showing activation of the stabilization device of FIG. 12.
Figure 43:
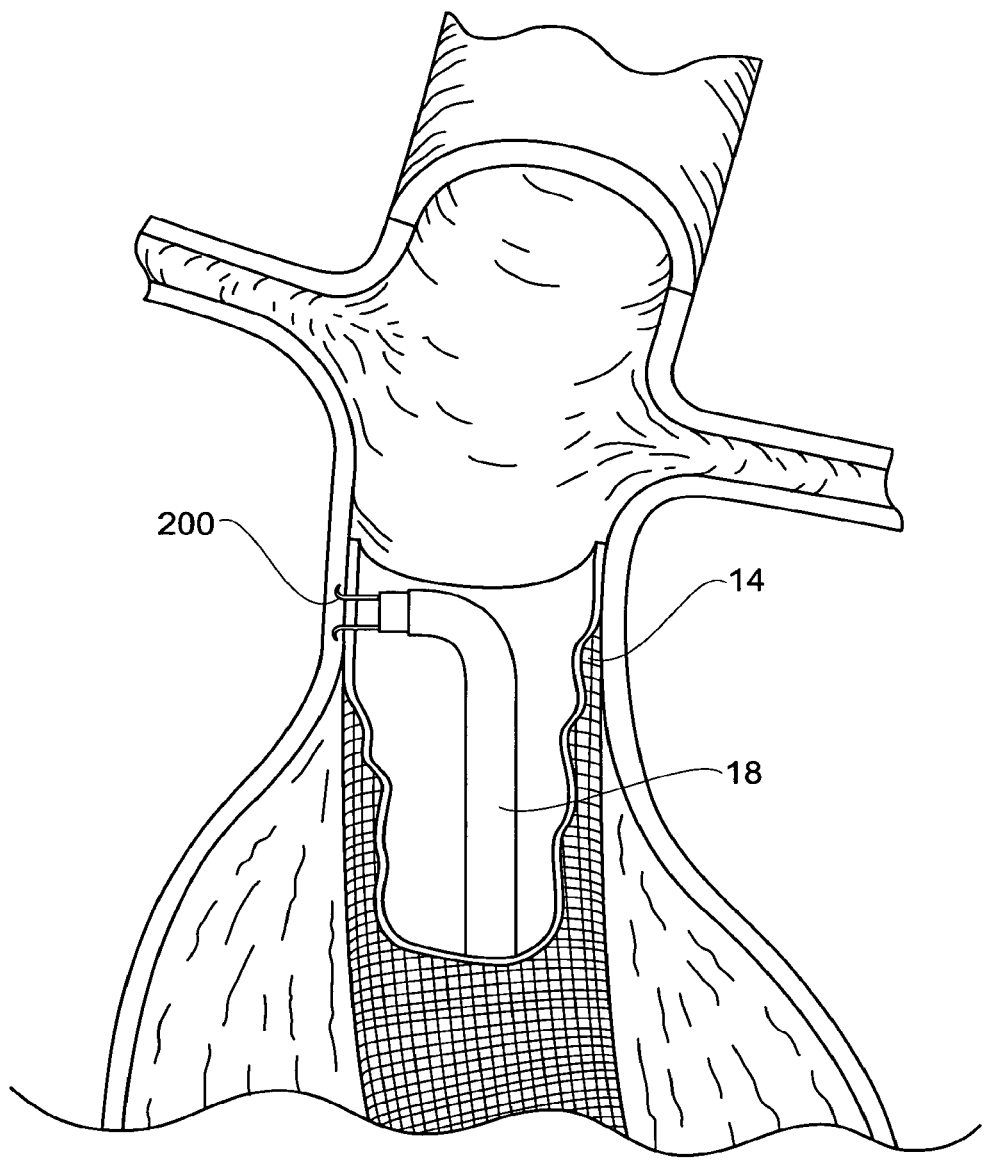
FIG. 43 is an elevation view of an alternative stabilization device, comprising tissue gripping elements.

The illustrated embodiments show various alternative embodiments for the stabilization means 20. As shown in FIGS. 8 and 9, the stabilization means 20 takes the form of a spring-loaded arm on the directing component 18 for contacting tissue. In this arrangement, the spring-loaded stabilizing means 20 is positioned for deployment when the obturator 19 and guidewire 12 are removed from the directing component 18 (see FIG. 8). In the alternative embodiment shown in FIGS. 10 and 11, the stabilization means 20 takes the form of a movable strut assembly 24 on the directing component 18, which contacts tissue. In this alternative arrangement, the movable strut assembly 24 can be activated, e.g., through a lever 25 on the control assembly (see FIG. 11). In both embodiments (FIGS. 7 and 10) the stabilizing device 20 is distal to the end of the directing component 18. In the alternative embodiment shown in FIG. 12, the stabilization means 20 takes the form of an expandable member 26 positioned adjacent the distal tip of the directing component 18. In this alternative arrangement (see FIG. 13), the expandable member 26 can be activated, e.g., through a lever 25 on the control assembly 21. However it also contemplated that this type of stabilizing means 20 could also be inflatable. In another alternative embodiment (see FIG. 43), the stabilization means 20 includes means 200 carried by the directing component 18 and/or the fastener applier component 27 for grasping and/or anchor to the wall of the hollow body organ, vessel or prosthesis prior to implanting a fastener. The grasping or anchoring means 200 can include penetrating needles and/or hooks or barbs that are deployed by a control assembly or the like prior to implantation of a fastener.

In all embodiments the stabilizing means 20 could be use to stabilize the directing component 18 either concentrically or eccentrically within the vessel.

Of course, any of these alternative forms of the stabilization means 20 can be associated with the fastener applier 27 in the same fashion they are shown to be associated with the directing component 18, or take some other form of a stabilization mechanism having the equivalent function. In yet another embodiment, the stabilization means 20 can take the form of a separate stabilization device used in cooperation with the directing component 18 and/or the fastener applier component 27. In this arrangement, the separate stabilization device could incorporate any of the alternative forms of the stabilizing devices described above, or some other form of stabilization mechanism.

Figure 44B:
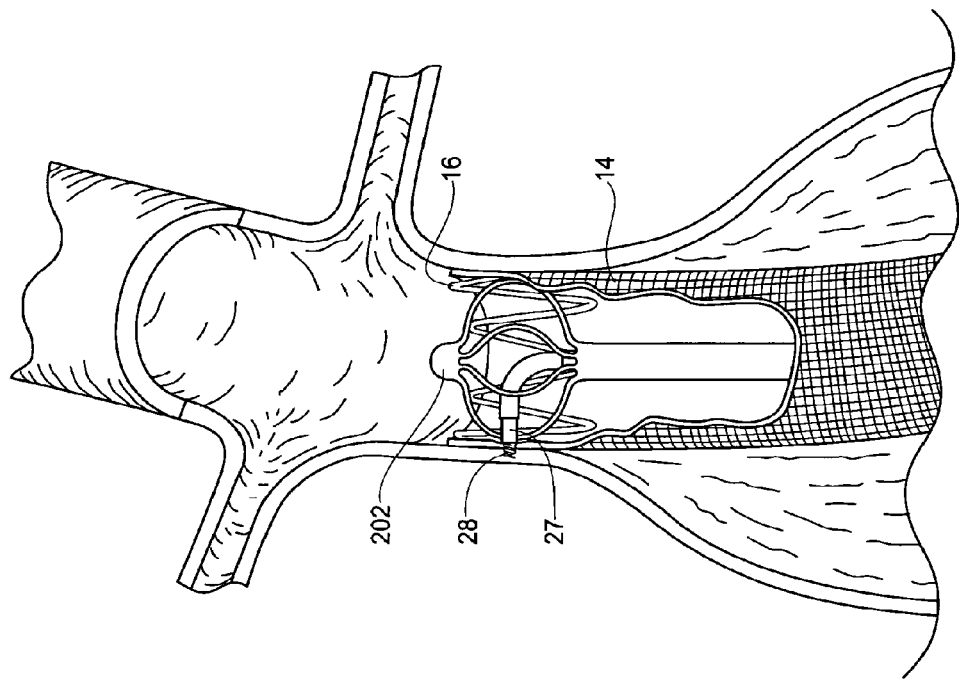
FIGS. 44A and 44B are elevation views of a fastener applier that carries an expandable basket-like structure that serves as a stabilization device, FIG. 44A showing the basket-like structure in a generally collapsed condition for intravascular deployment and FIG. 44B showing the basket-like structure in an expanded condition against a vessel wall and graft for deployment of a fastener.

For example (see FIGS. 44A and 44B), the fastener applier 27 can carry about its distal end an expandable basket 202 or basket-like structure. The basket structure 202 surrounds the fastener drive mechanism 100, which has been previously described. The basket structure 202 is operable between a low profile, generally collapsed condition (shown in FIG. 44A) and an expanded profile condition (shown in FIG. 44B) about the fastener drive mechanism 100.

Figure 44A:
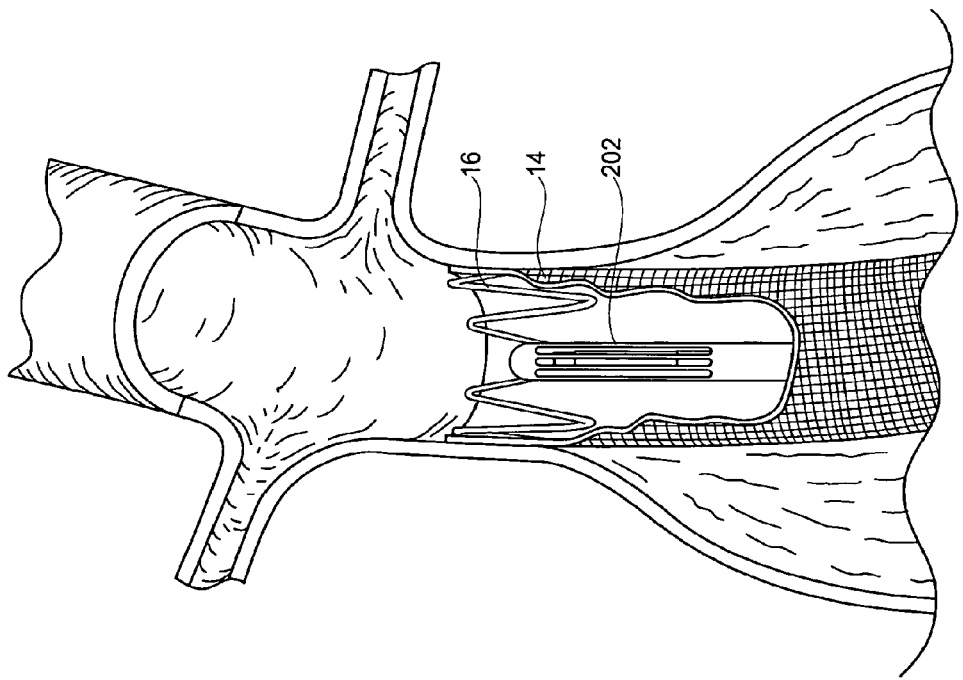

In the generally collapsed condition, the fastener applier 27 can be deployed through a vessel into proximity to a graft 14. FIG. 44A shows the graft 14 to include a self-expanding scaffold 16. When in the generally collapsed condition, the fastener applier 27 can be deployed in its low profile state through the vasculature to the targeted graft site either by itself, or through an associated directing component 18 or suitable guide sheath, which can steerable or non-steerable.

When situated at the graft site (see FIG. 44B), the basket structure 202 can be expanded (e.g., by a suitable push-pull control mechanism) into contact with the graft 14. The fastener applier 27 can be maneuvered within the expanded basket structure 202 into contact with the graft 14 and operated to deploy a fastener 28, as previously described. The basket structure 202 serves to resolve at least some of the implantation force to provide positional stability and resist unintended movement of the fastener applier 27.

Figure 45:
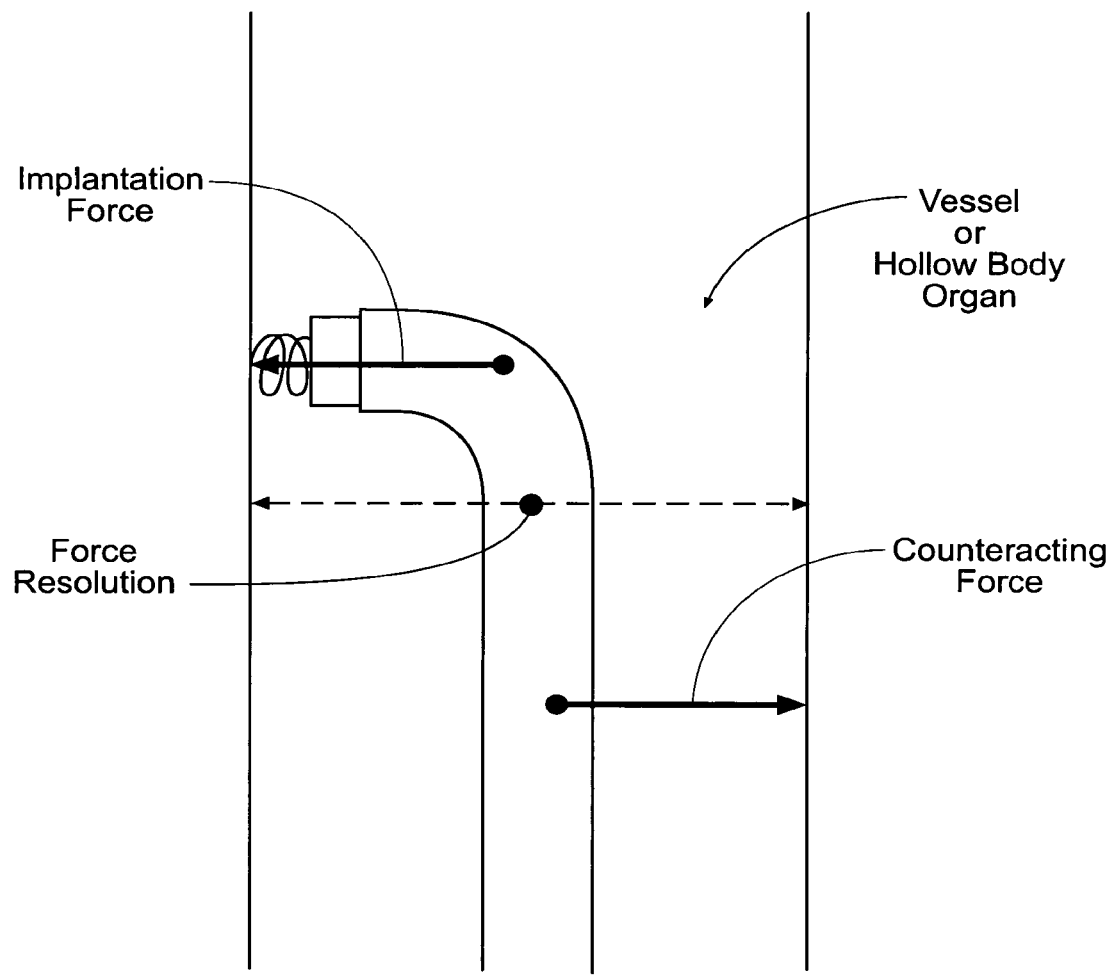
FIG. 45 shows, in diagrammatic fashion, the resolution of an implantation force with a counteracting force within a vessel or hollow body organ.

In all these alternative embodiments, the stabilization means 20 functions to apply a substantially equal and opposite counteracting resolution force within a vessel (see FIG. 45) to a location on the vessel wall, desirably generally opposite to the implantation site. As also just described, the column strength of the associated directing component 18 and/or fastener applier 27 can also serve in conjunction with the stabilization means 20 to resolve the intraluminal implantation force at the implantation site.

The force resolving function that the guiding component 18 and/or the fastener applier component 27 provide serves to counteract or oppose or otherwise resolve the tissue penetration and implantation force of the applier component 27. The force resolving function thereby also resists movement of the applier component 27 relative to the implantation site, thereby making possible a stable and dependable intraluminal (or intra organ) fastening platform.

4. Prosthesis/Tissue Contact Sensing

The fastener applier component 27 desirably incorporates a function that prevents actuation of the motor 106 until the tip of the applier component 27 is in a desired degree of contact with the prosthesis or tissue surface. This prevents inadvertent discharge of a fastener 28 and/or separation of the fastener 28. This function can be implemented, e.g., using a contact or force sensor, which is either mechanical or electrical in design.

Figure 14B:
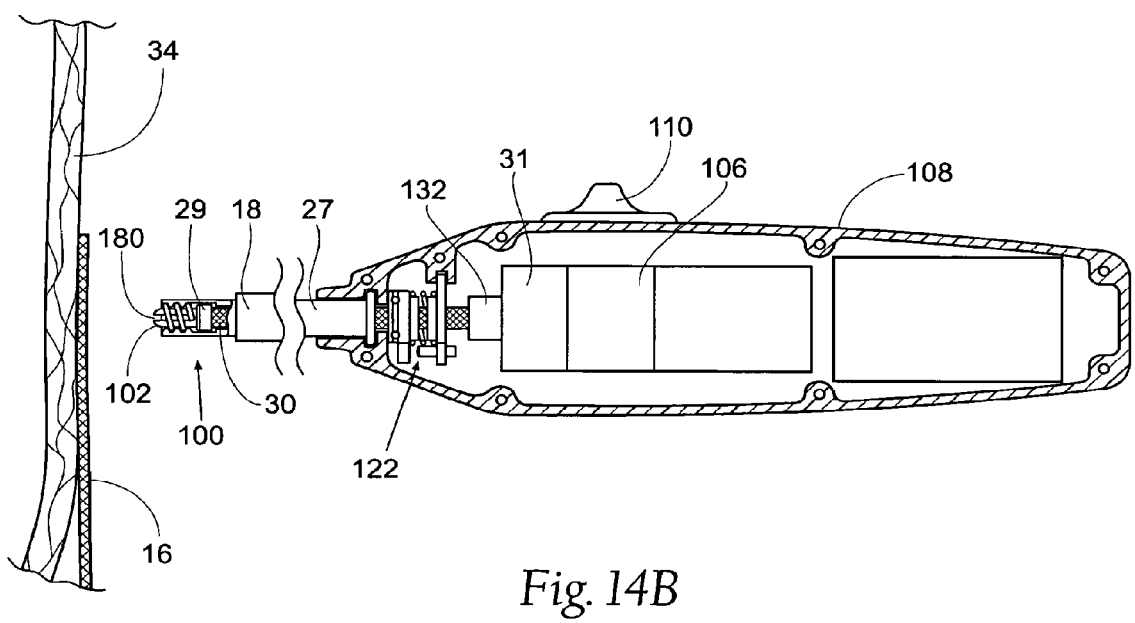
FIG. 14B is a section view of the interior of the handle of the fastener applier shown in FIG. 14.

When the fastener applier component 27 is of the type shown in FIGS. 14A, 14B, and 14C (see FIGS. 23 and 24), the contact or force sensing function can, e.g., utilize the distal tip 120 of the carrier 102 to transmit a contact force. This force can be transmitted to a force or contact sensing switch 122 located, e.g., within the fastener applier handle 108. In this arrangement, the switch 122 can be part of the electrical circuit between the actuator switch 110 and the control unit 31.

In the illustrated embodiment, the switch 122 includes a stationary switch element 128 (coupled to the interior of the handle 108) and a movable switch element 130 (carried by the drive cable 31). In this arrangement, the motor coupling 132 between the drive cable 30 and the motor 106 accommodates axial displacement of the motor cable 30 (left and right in FIGS. 23 and 24) without interrupting the drive connection with the motor 106. The drive cable 30 is coupled by a bearing 134 to the movable switch element 130, so that the switch element 130 moves in response to movement of the drive cable 30. The stationary switch element 128 is not coupled to the movable drive cable 30, which slidably passes through the switch element 130.

Due to this arrangement, axial displacement of the drive cable 30 moves the switch element 130 relative to the switch element 128. More particularly, displacement of the drive cable 30 to the left in FIG. 23 moves the switch element 130 to the left, away from the switch element 128. Conversely, displacement of the drive cable 30 to the right in FIG. 23 moves the switch element 130 to the right, toward the switch element 128.

A spring 126 normally biases the switch elements 128 and 130 apart, comprising an electrically opened condition. In this condition, operation of the actuating switch 110 does not serve to actuate the control unit 31, as the electrically open switch 122 interrupts conveyance of the actuation signal to the motor control unit 31. When the switch elements 128 and 130 are in the electrically opened condition, the drive cable 30 is displaced to the left to position the carrier tip 120 beyond the distal tip 124 of the fastener applier 27. The carrier tip 120 therefore makes contact with the prosthesis 14 or tissue in advance of the applier tip 124.

Figure 23:
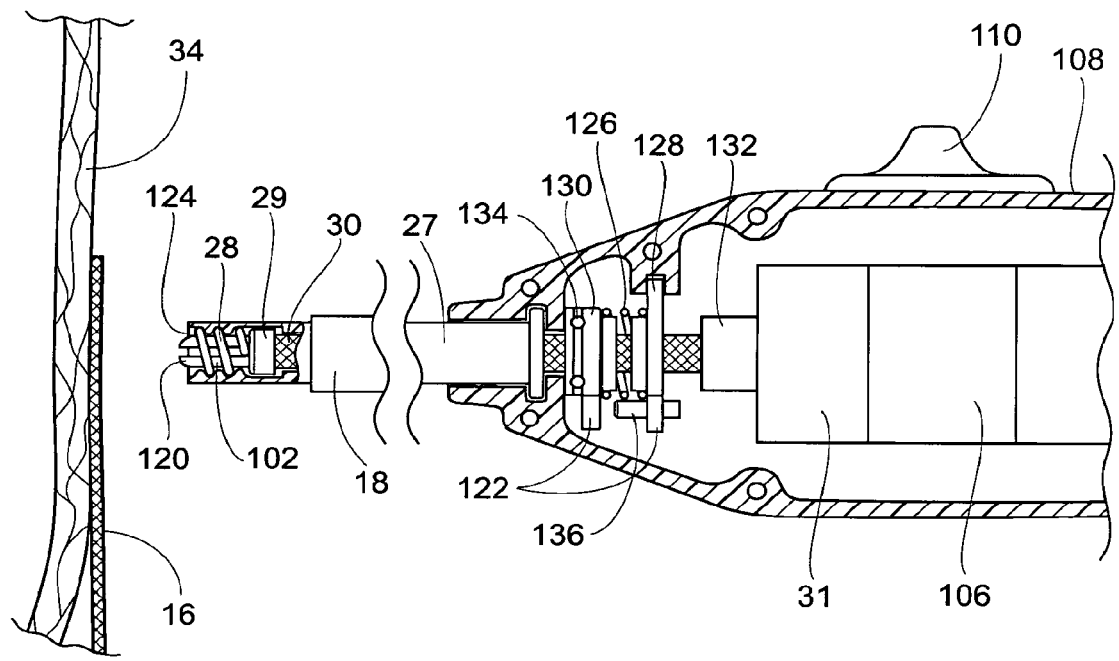
FIG. 23 is an enlarged section view of the drive mechanism of the fastener applier shown in FIG. 14, showing a contact/force sensing assembly that disables the applier in the absence of desired contact between the fastener and a targeted tissue region.
Figure 24:
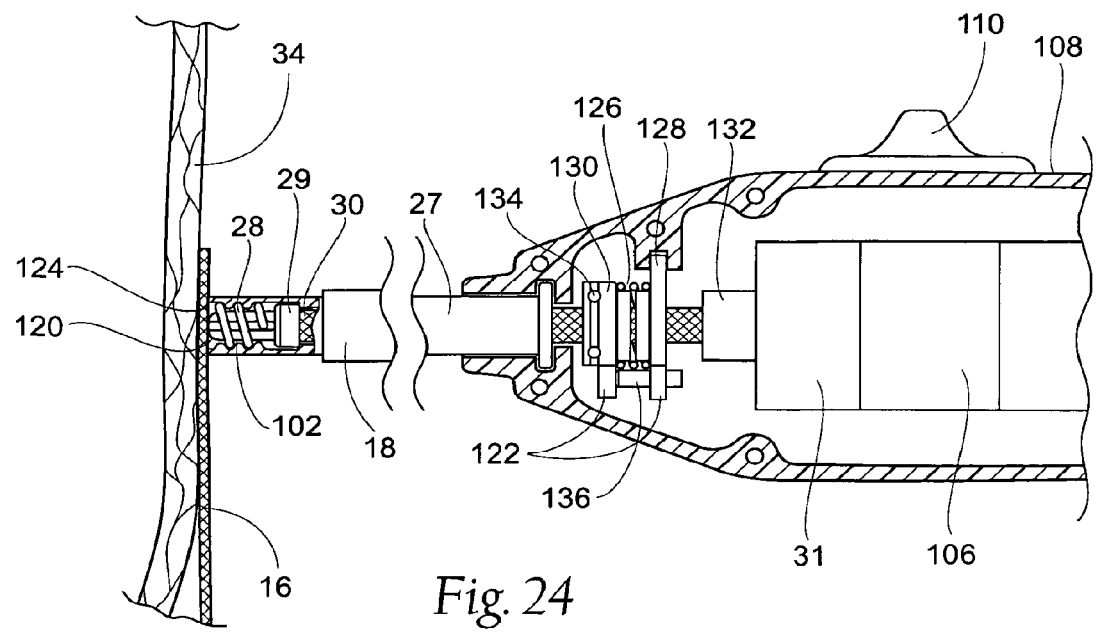
FIG. 24 is an enlarged section view of the drive mechanism of the fastener applier shown in FIG. 14, showing the contact/force sensing assembly enabling use of the applier in response to desired contact between the fastener and the targeted tissue region.

When the carrier tip 120 contacts the surface of the prosthesis or tissue with sufficient force to compress the spring 126, the drive cable 30 is displaced against the biasing force of the spring to the right in FIG. 23. This moves the switch element 130 to the right. Ultimately, contact between the switch elements 128 and 130 will occur, as shown in FIG. 24. The contact establishes an electrically closed, condition. In this condition, operation of the actuating switch 110 serves to actuate the control unit 31. As shown in FIGS. 23 and 24, a contact screw 136 can be provided to adjust the amount of displacement required to close the switch elements 128 and 130.

Upon removal of contact force, or in the absence of sufficient contact force, the spring 126 urges the switch elements 128 and 130 toward the electrically opened condition. The distal tip of the carrier 102 is located distally beyond the distal tip of the applier 27.

It should be appreciated that the translation of movement of the carrier tip 120 to the switch 122 need not occur along the entire length of the drive cable 30. For example, the switch 122 can be located in a translation space between the carrier 102 and the driver 29. In this arrangement, the driver 29, coupled to the drive cable 30 need not accommodate axial displacement. Instead, relative movement of the carrier 102 toward the driver 29 in response to contact with the prosthesis 14 will mechanically couple the carrier 10 with the driver 29 (e.g., through a slot and flange connection similar to that shown in FIGS. 25A and 25B), while also closing the switch 122 to energize the circuit between the actuator switch 110 and the motor control unit 31.

Figure 28B:
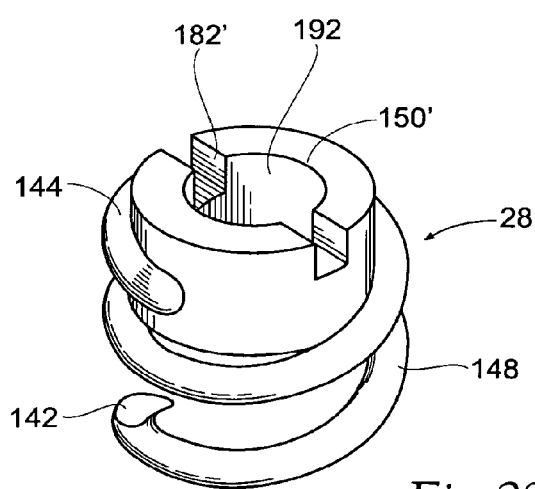
FIG. 28B is perspective view of a helical fastener that can be used in association with the fastener applier shown in FIGS. 26A to 26C.

When the fastener applier component 27 is of the type shown in FIGS. 25A and 25B (see FIGS. 26A, 26B, and 26C), the contact or force sensing function can, e.g., utilize a force sensing rod 190 that slidably passes through a central passage 192 in the carrier 150' (the carrier 150' is shown in FIG. 28B), the driver 29 and the drive cable 30. The rod 190 is coupled to the movable switch element 130. In this embodiment, the switch element 130 translates left and right over the drive cable 30, which rotates on a bearing 134 within the switch element 130.

As in the preceding embodiment, the spring 126 normally biases the switch elements 128 and 130 apart, comprising an electrically opened condition. When the switch elements 128 and 130 are in the electrically opened condition, the force sensing rod 190 is displaced to the left beyond the distal tip 124 of the fastener applier component 27. The force sensing rod 190 therefore makes contact with the prosthesis 14 or scaffold structure 16 in advance of the applier tip 124.

When the rod 190 contacts the surface of the prosthesis or scaffold structure with sufficient force to compress the spring 126, the rod 190 is displaced against the biasing force of the spring 126 to the right in FIG. 26A. This moves the switch element 130 to the right. Ultimately, contact between the switch elements 128 and 130 will occur, as shown in FIG. 26B. The contact establishes an electrically closed condition. In this condition, operation of the actuating switch 110 serves to actuate the control unit 31. This action causes the helical fastener 28 to be rotated into the scaffold structure 16 and into the vessel wall 34 (see FIG. 26C). Due to the magnetic coupling between the driver 29 and carrier 150', the driver 29 is moved in tandem with attached carrier 150' to the left in FIG. 26B, as the fastener 28 is deployed. Also, due to the magnetic coupling between the carrier 150 and the driver 29, the operator must exert a separation force to decouple the carrier 150 (and, with it, the fastener 28) from the driver 29. As before described, this arrangement prevents inadvertent release of a fastener 28. A contact screw 136 can be provided to adjust the amount of displacement required to close the switch elements 128 and 130.

Upon removal of contact force, or in the absence of sufficient contact force, the spring 126 urges the switch elements 128 and 130 toward the electrically opened condition, moving the tip of the rod 190 out beyond the distal tip 124 of the applier 27.

The contact or force sensing arrangements just described can also generate an audible and/or visual output to the operator, to indicate that sufficient contact force between the applier device 27 and the prosthesis or tissue exists.

B. Angled Component Fastener Guide and Attachment Assembly

In another arrangement (see FIG. 29), the fastener attachment assembly comprises a unitary, angled fastener guide and applier component 160. In this arrangement, the component 160 includes a fastener drive mechanism 162 that places the carrier 164 holding the fastener 28 in a perpendicular or near perpendicular position with respect to the prosthesis or tissue. This configuration eliminates the need for a separate steerable guide component 18 for the fastener component 27, previously described.

Figure 29:
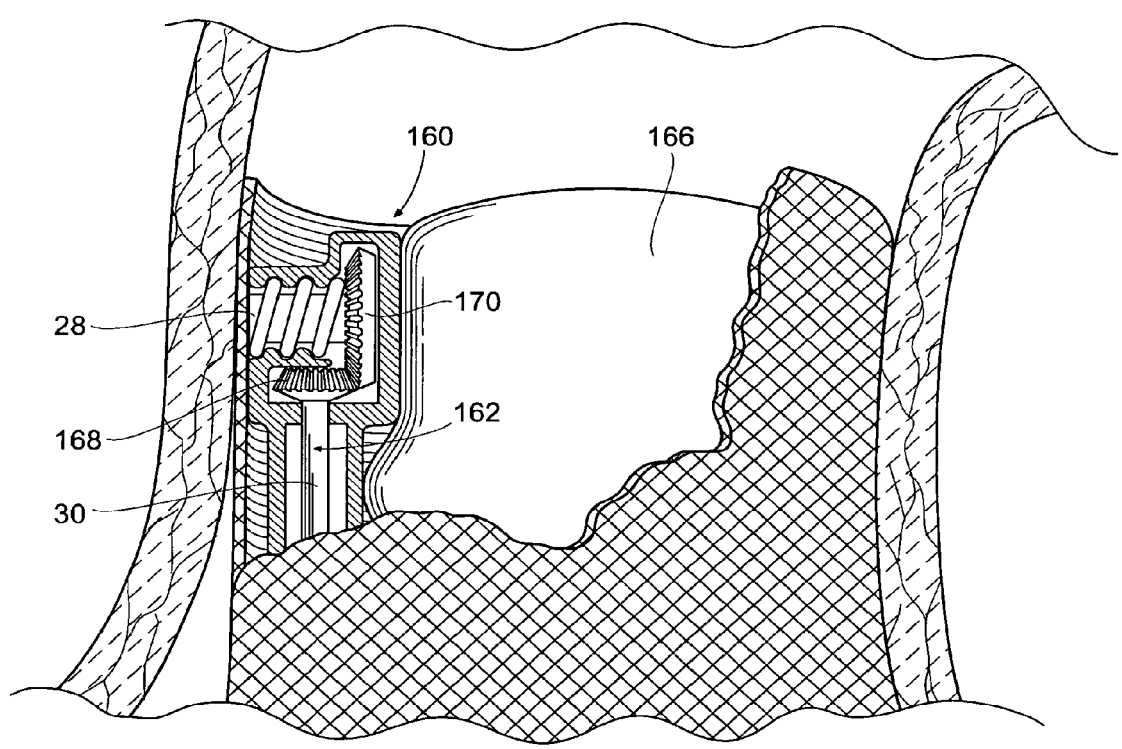
FIG. 29 is an enlarged side view, partially in section, of a fastener applier having an angled applicator end that can be used to deploy the helical fastener shown in FIG. 27 without use of a separate directing device.

The drive mechanism 162 can vary. In the illustrated embodiment (shown in FIG. 29), the mechanism 162 includes a beveled drive gear 168 coupled to the drive cable 30. The drive gear 168 operatively meshes with a transfer or pinion gear 170, which is coupled to the carrier 164. The axes of rotation of the drive gear 168 and pinion gear 170 are offset about ninety degrees, so that rotation of the drive cable 30 along the axis of the vessel is translated into rotation of the carrier 164 generally perpendicular to the wall of the vessel. The fastener guide and applier component 160 can be positioned and stabilized within the vessel in various ways, e.g., through the use external spring loaded strut or the like (as shown in association with the directing component 18 discussed above), or by use of an expandable member 166 (as FIG. 29 shows). The expansion member 166 can comprise either a balloon or mechanical expansion device. The expansion member 166 stabilizes the position of both the prosthesis and the fastener guide and applier component 160 within the vessel by resisting the force of blood until the prosthesis can be anchored.

Figure 30:
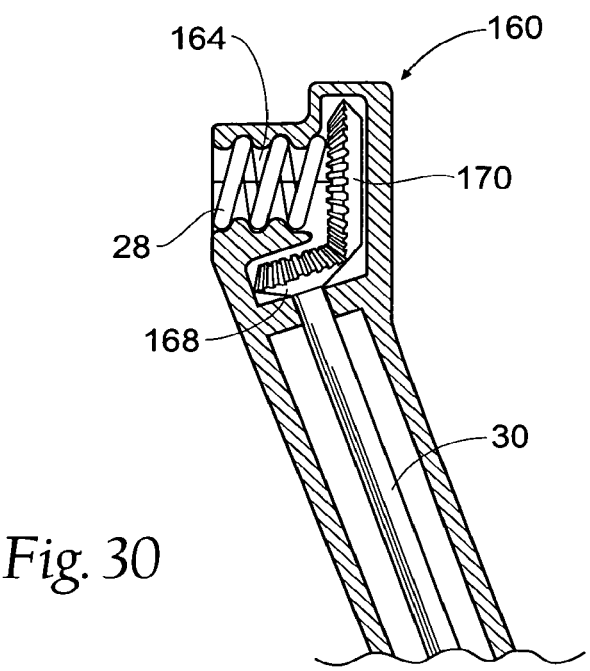
FIG. 30 is an enlarged side view, partially in section, of an alternative embodiment of an angled fastener applier that can be used to deploy the helical fastener shown in FIG. 27 without use of a separate directing device.
Figure 31:
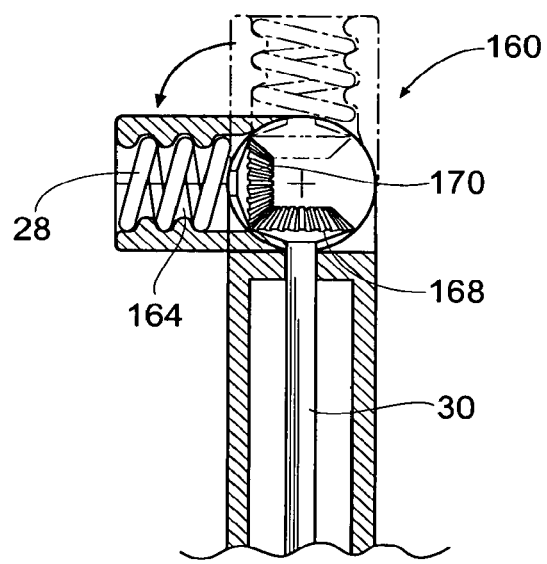
FIG. 31 is an enlarged side view, partially in section, of an alternative embodiment of an angled fastener applier that can be used to deploy the helical fastener shown in FIG. 27 without use of a separate directing device, the fastener applier having an articulating applicator end.

As FIG. 30 shows, the fastener guide and applier component 160 can, if desired, provide an angled deployment between the drive cable 30 and carrier 164 that is somewhat less than ninety-degrees, to aid in intraluminal manipulation of the carrier into perpendicular contact position against the wall of the vessel. As FIG. 31 shows, the fastener guide and applier component 160 can, if desired, be articulated between the drive cable 30 and carrier 164. In this arrangement, a remote control mechanism is desirable provided to move the carrier 164 from a first, generally straight position (shown in phantom lines in FIG. 31) for deployment to the targeted site, to a second, articulated position (shown in solid lines in FIG. 31) for alignment of the carrier 164 in contact against the vessel wall.

III. The Fasteners

As illustrated and described thus far, introduction of the fasteners 28 will typically be affected after the prosthesis 14 has been initially placed. That is, initial placement of the prosthesis 14 will be achieved by self-expansion or balloon expansion, after which the prosthesis 14 is secured or anchored in place by the introduction of a plurality of individual fasteners. The fasteners 28 may be placed only through the fabric of the prosthesis 14, i.e., avoiding the scaffold structure. Alternately, the fasteners 28 can be introduced into and through portions of the scaffold structure itself. The prosthesis 14 may include preformed receptacles, apertures, or grommets, which are specially configured to receive the fasteners. The fasteners 28 may be introduced both through the fabric and through the scaffold structure. The fasteners can be introduced singly, i.e., one at a time, in a circumferentially spaced-apart pattern over an interior wall of the prosthesis 14.

In the exemplary embodiment, the fasteners 28 are helical fasteners, so that they can be rotated and "screwed into" the prosthesis 14 and vessel wall. A desired configuration for the helical fastener 28 (see FIGS. 27, 28A, and 28B) is an open coil 148, much like a coil spring. This configuration allows the fastener 28 to capture a large area of tissue, which results in significantly greater holding force than conventional staples, without applying tissue compression, which can lead to tissue necrosis.

As FIGS. 27, 28A, and 28B show, the leading tip 142 of the helical fastener 28 is desirable sharp to allow it to penetrate thought the artery wall and/or calcified tissue. This distal tip 142 can be sharpened to cut a helical path through the tissue or it can be sharpened to a point to penetrate the tissue without cutting.

The proximal end 144 of the fastener serves two design functions. The first function is to engage the carrier 102 of the fastener applier 27, which rotates the helical fastener during the implantation process. The second function is to act as a stop to prevent the helical fastener from penetrating too far into the tissue.

In one embodiment (see FIG. 27), the proximal end 144 of the helical fastener 28 includes an L-shaped leg 146 of the coil 148 bisecting the fastener diameter. The leg 146 of the coil 148 comes completely across the diameter to prevent the fastener from being an open coil and to control the depth of penetration into the tissue. In addition, the leg 146 of the coil 148 can be attached to a previous coil to strengthen the entire structure and provide a more stable drive attachment point for the fastener applier. This attachment could be achieved via welding, adhesive or any other suitable means.

Alternatively (as shown in FIGS. 28A and 28B), the proximal end 144 of the fastener 28 could incorporate a separate cap or carrier 150 or 150' that serves the same function as the leg 146 of the coil 148 in FIG. 27. The carrier 150 or 150' could feature several methods to attach to the fastener applier drive mechanism 100. These include separate graspers or grippers, a magnetic couple (as previously described), or any other suitable mechanical connecting means. In FIGS. 28A and 28B, the carrier 150 and 150' includes a slot 180 and 182' to mate with a drive flange (as previously described). As also previously described, a magnetic coupling is implemented between the carrier 150 and 150' and the corresponding drive member, to prevent inadvertent separation during use.

In FIG. 28B, the carrier 150' also includes a passage 152 for holding the contact/force sensing rod 190 shown in FIGS. 26A, 26B, and 26C.

The fasteners 28 shown in FIGS. 27, 28A, and 28B can be made from stainless steel or other types of implantable metal, however it is also envisioned that the fasteners in the above descriptions could be made from implantable polymers or from a biodegradable polymer or combinations of all materials thereof. Desirably, a fastener 28 will have between 2 and 10 turns and will be between 1 mm and 10 mm long. The space between the individual coils will be between 0.25 mm and 3 mm. The diameter of the fastener 28 will be between 1 mm and 6 mm.

IV. Prosthesis with Integrated Fastener Assembly

Figure 32:
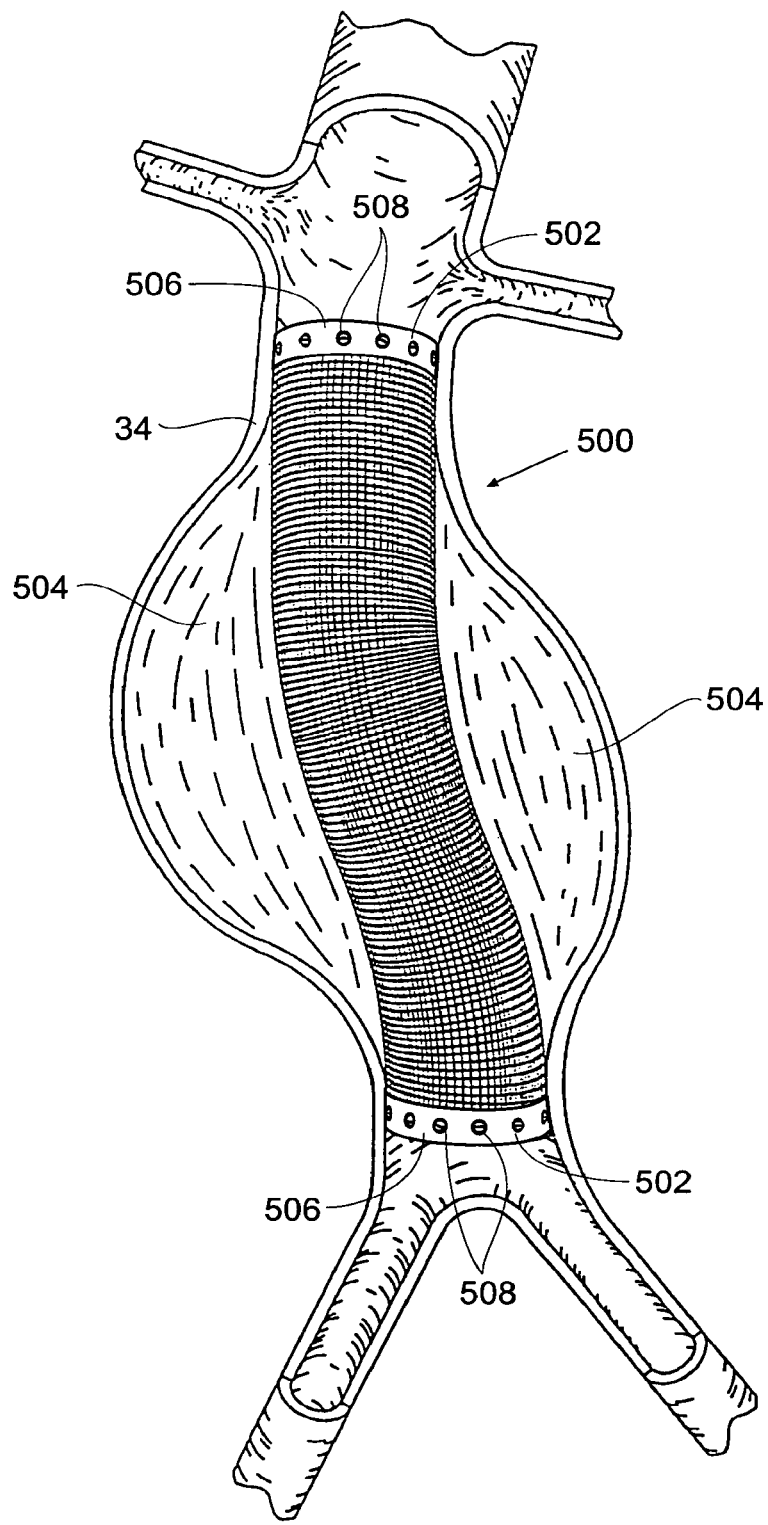
FIG. 32 is a perspective view of an endovascular prosthesis shown positioned within an abdominal aortic aneurysm, the prosthesis including an integrated fastener assembly.

FIG. 32 shows a prosthesis 500 that includes at least one integrated fastener assembly 502. FIG. 32 shows the prosthesis 500 deployed in a targeted intraluminal region, in particular, within an abdominal aortic aneurysm 504. The prosthesis 500 can be deployed elsewhere in the body.

The prosthesis 500 desirably includes a fabric material or the like carried by a support frame or scaffold 504, as previously described. The scaffold 504 can be made, e.g., from an elastic material that self-expands radially during deployment from a sheath, or from a malleable material that expands radially in response to a radially expansive force applied within the scaffold by a balloon or a mechanical expansion device.

Following deployment of the prosthesis 500 in the targeted region, the integrated fastener assembly 502 on the prosthesis 500 is manipulated to anchor the prosthesis 500 to the vessel wall. In the illustrated embodiment, the prosthesis 500 carries two integrated fastener assemblies 502, one in each end region of the prosthesis 500.

In the illustrated embodiment, each fastener assembly 502 is imbedded in a reinforced flange area 506 in the respective end region. Each fastener assembly 502 comprises an array of fasteners 508 circumferentially spaced about the flange 506. The number of fasteners 508 in the array can vary, e.g., from about two to about twelve fasteners on each flange area 506. The configuration of the array can also vary, e.g., in the circumferential array, the fasteners 508 can by axially spaced apart as well.

Figure 34:
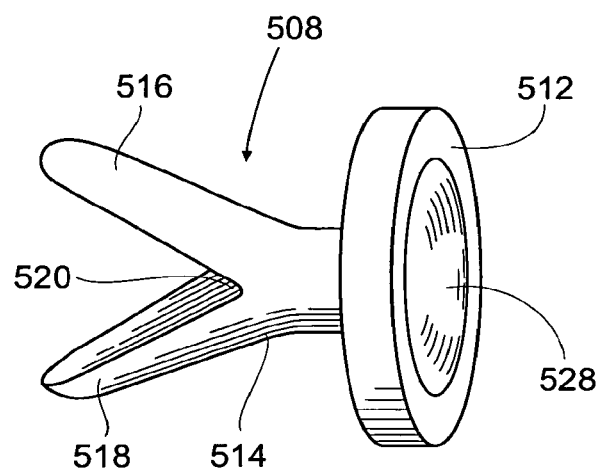
FIG. 34 is a side view of a fastener that forms a part of the integrated fastener assembly shown in FIG. 33, the fastener having a stem, which is shown in a normally spread-apart condition before its association with the integrated fastener assembly.

The fasteners 508 can be formed of a metal or plastic material and can be variously constructed. In the illustrated embodiment, each fastener 508 includes a disc-shaped head 512 and a stem 514 that is bifurcated into two wings 516 and 518, which are joined by a plastic or memory material hinge region 520. The material of the hinge region 520 is formed with a resilient memory that biases the wings 516 and 518 to a spread-apart condition (as FIG. 34 shows).

Figure 35:
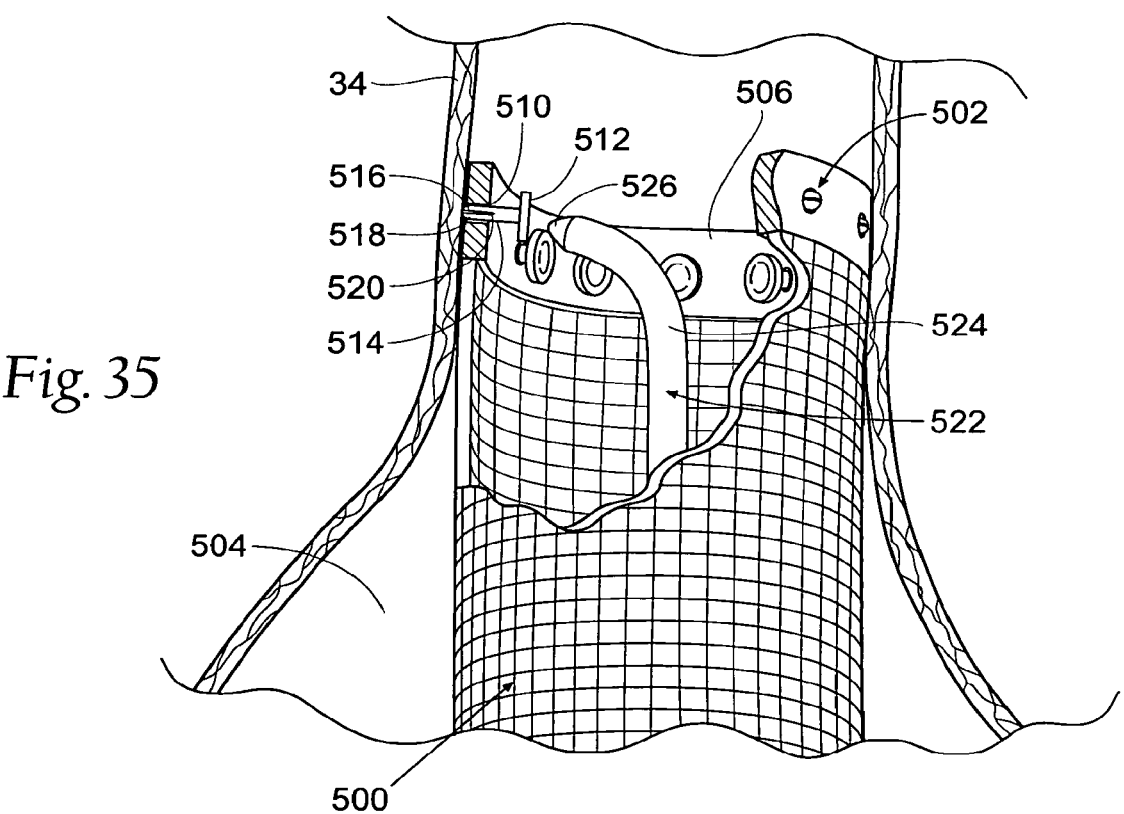
FIG. 35 is a side view of the fastener shown in FIG. 34, the fastener stem now being shown in a closed condition and housed within a grommet that forms a part of the integrated fastener assembly.

Each fastener 508 is carried within a grommet 510 on the flange area 506 (see FIG. 35). When the hinge region 520 is confined within the grommet 510 (as FIG. 35 shows), the wings 516 and 518 are retained against the resilient memory in an adjacent, closed condition. In response to the application of a pushing or punching force on the head 512 (see FIG. 35), the wings 516 and 518 are advanced in the closed condition out of the grommet 510, and into and through the adjacent vessel wall (see FIG. 36). Upon continued advancement, the hinge region 520 is freed from the confines of the grommet 510 (see FIG. 37). As a result, the wings 516 and 518 resiliently spring into their normal spread-apart condition.

Figure 33:
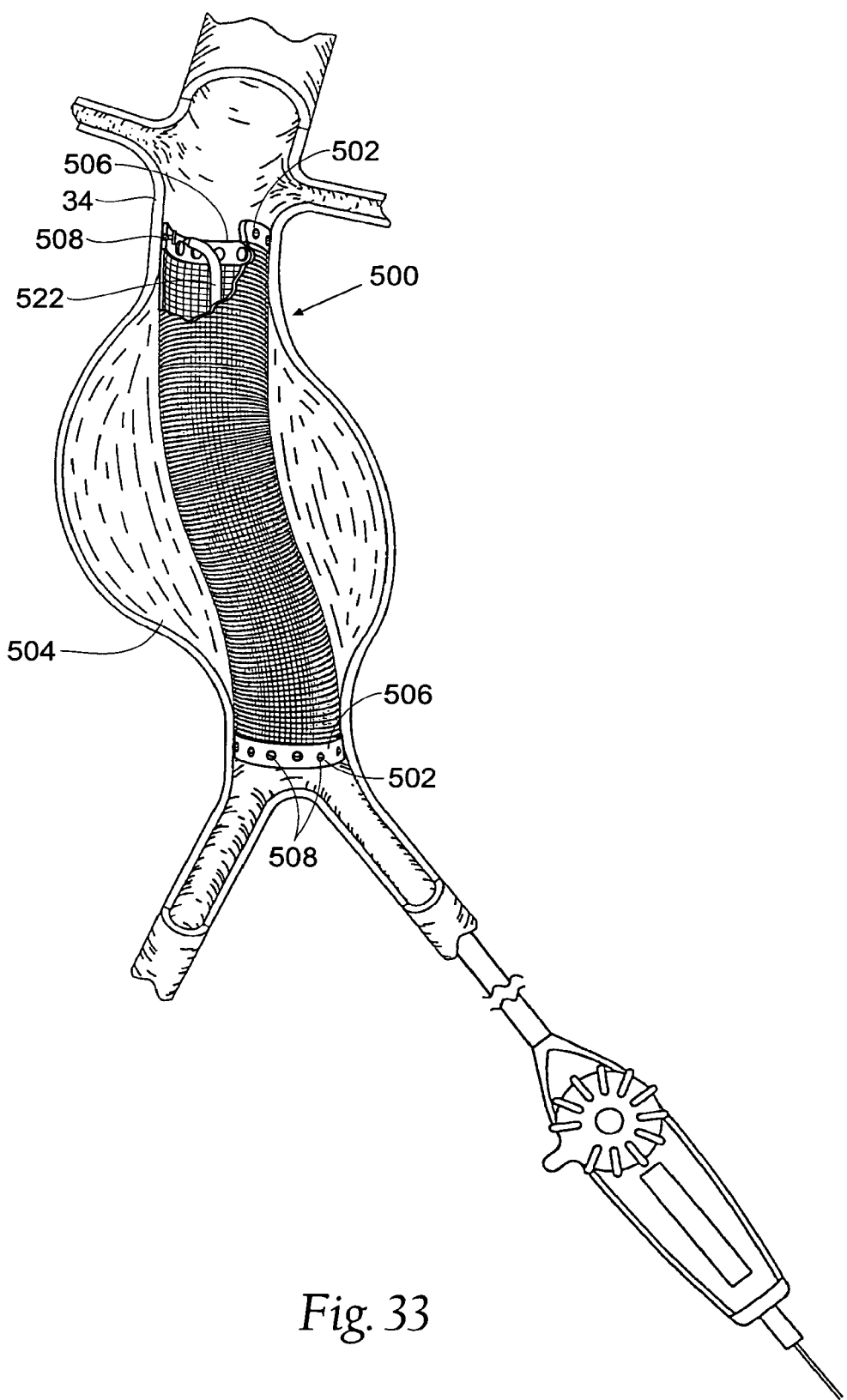
FIG. 33 is a perspective view of the endovascular prosthesis shown in FIG. 32, with an intraluminal tool deployed to operatively interact with the integrated fastener assembly, to temporarily or permanently anchor the prosthesis to the wall of the vessel.

In this arrangement, an intraluminal tool 522 (see FIG. 33) is deployed into the prosthesis 500 to exert a pushing or punching force upon the head 512 of a given fastener 508. In the illustrated embodiment, the tool 522 comprises a catheter 524 that carries a punch member 526 at its distal end. In a desired arrangement, the distal end of the catheter 524 is steerable, to aid in establishing point contact between the punch member 526 and the head 512 of the given fastener 508. The head 512 can include a recess 528 to receive and stabilize the tip of the punch member 526 with respect to the head 512 during use (see FIG. 34).

Figure 36:
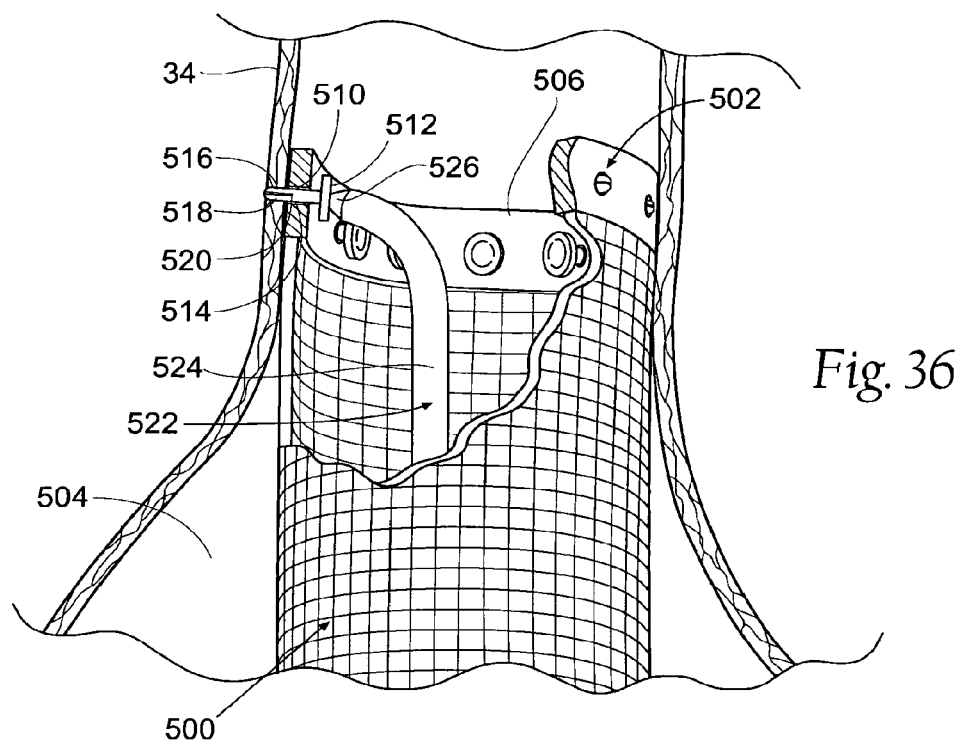
FIGS. 36 and 37 are side views showing the use of the intraluminal tool shown in FIG. 33 to apply force to drive the fastener from its position shown in FIG. 35 and through the vessel wall.
Figure 37:
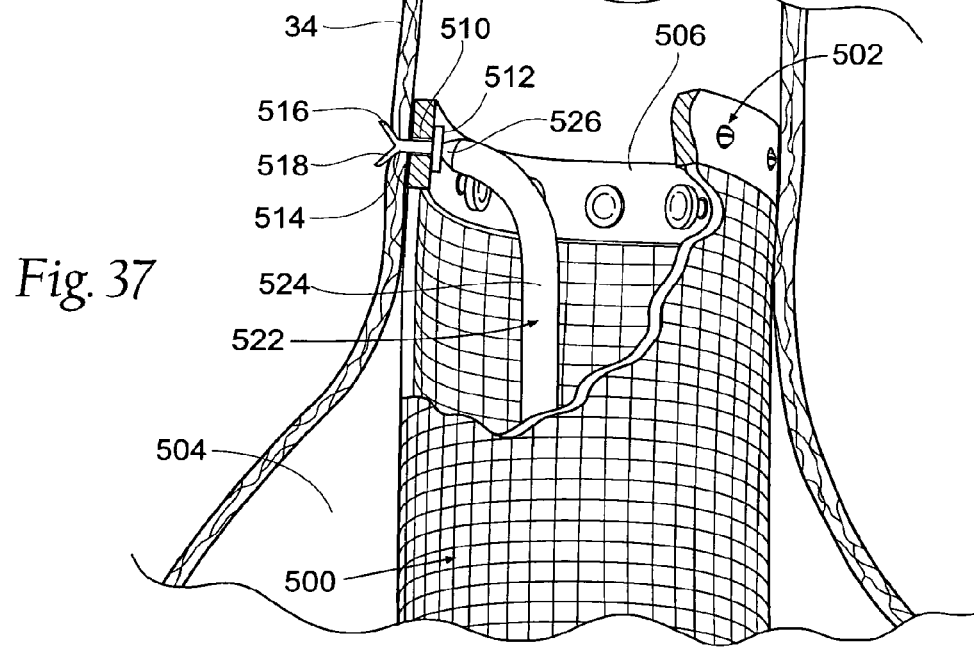
Figure 38:
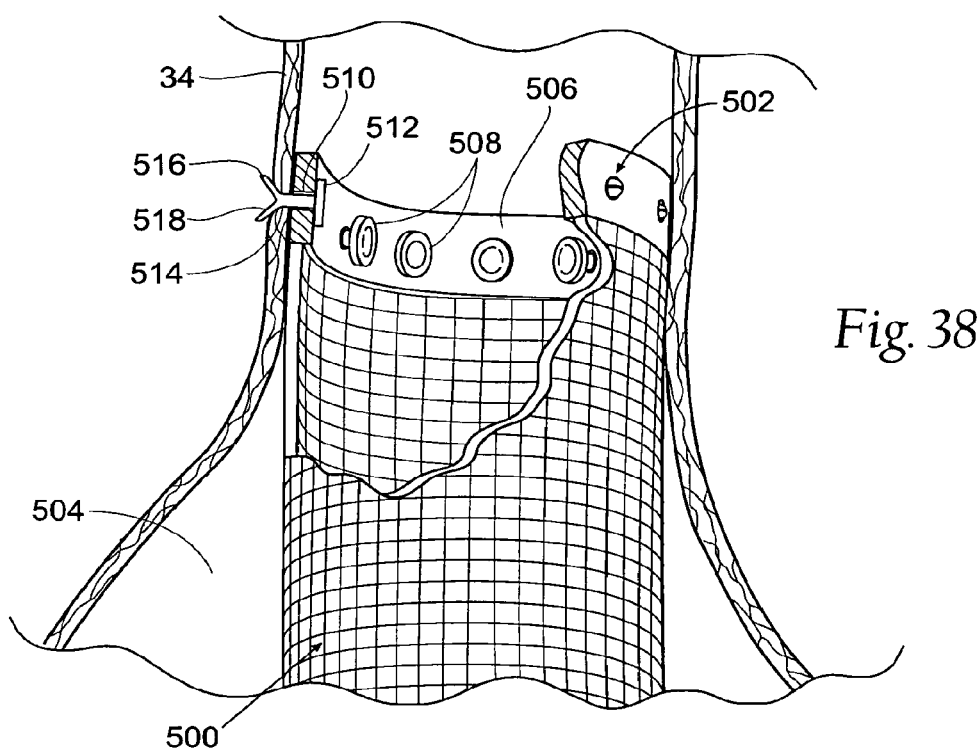
FIG. 38 is the integrated fastener assembly after deployment to anchor a prosthesis to a vessel wall.

In use, the punch member 526 is manipulated to apply a pushing or punching force upon the selected fastener head 512. As FIGS. 35 and 36 show, the application of the pushing force by the punch member 526 forces the wings 516 and 518 against the near side of the vessel wall 34. The wings 516 and 518 are still in their closed condition, because the hinge region 520 is still confined within the grommet 510. The closed wings 516 and 518 form an obturator that penetrates tissue as it advances to the far side of the vessel wall. As the hinge region 510 is freed from the grommet 510 (FIG. 37), the wings 516 and 518 resiliently return to their spread-apart condition against the far side of the vessel wall. Upon removal of the punch member 526 (see FIG. 38), the head 512 and spread-apart wings 516 and 518 remain in their mutually opposed condition in the vessel wall, to secure the prosthesis 500 against the vessel wall. In use, the physician locates and manipulates the punch member 526 in succession against each fastener 508, to complete the anchorage of the prosthesis 500 to the vessel wall.

Figure 39:
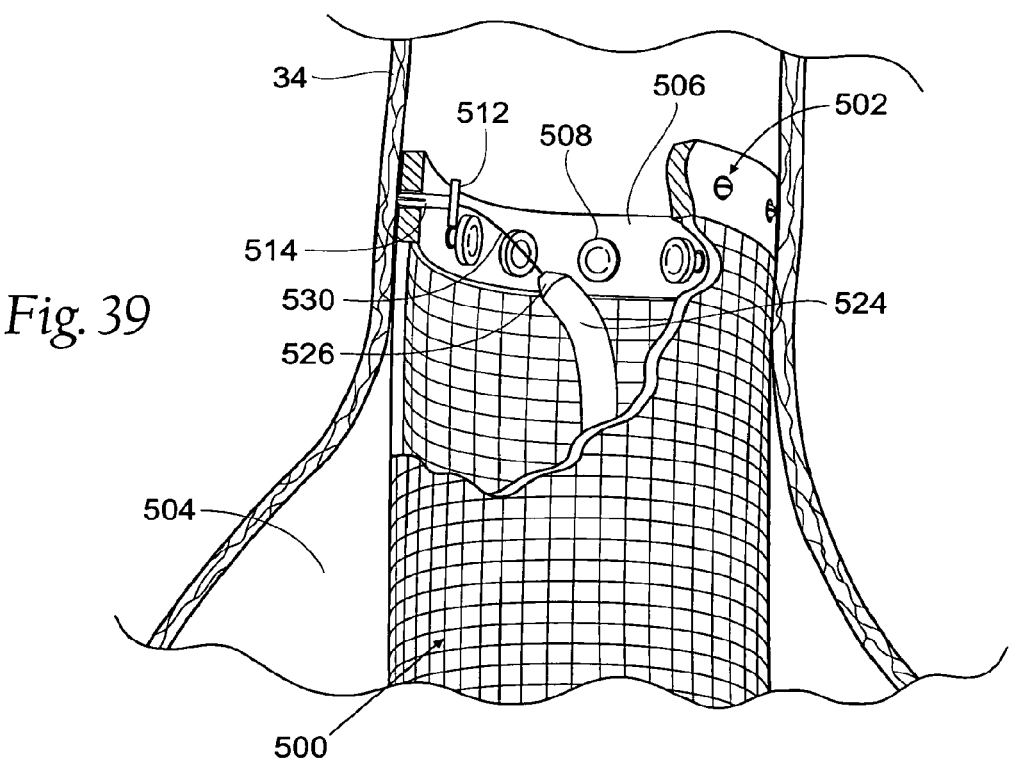
FIG. 39 is a side view showing the use of a tracking wire to guide a intraluminal tool into contact with a fastener, so that force can be applied to drive the fastener through the vessel wall.

In one embodiment (see FIG. 39), each fastener 508 can include a tracking wire 530 that is releasably coupled to the head 512. The tracking wire 530 extends from the head 512 outside the body for access outside the vessel. In this arrangement, the punch member 526 includes a lumen to accommodate passage of the tracking wire 530. The tracking wire 530 guides the punch member 526 in an intraluminal path to the respective fastener 508. After the punch member 526 is manipulated to drive the fastener 508 into the vessel wall, the punch member 526 can be withdrawn over the tracking wire 530. The tracking wire 530 can be released from the now-secured head 512, e.g., by applying a moderate pulling force upon the tracking wire 530. The tracking wire 530 can then be withdrawn. The punch member 526 is sequentially guided over another tracking wire 530 for interaction with another one of the fasteners 508, until a desired degree of anchorage is achieved.

In an alternative embodiment, an integrated fastener assembly 502 on the prosthesis 500 can be used to temporarily tack the prosthesis 500 in place while a permanent anchoring technique is carried out. For example, in this arrangement, after using the integrated fastener assembly 502 to temporarily hold the prosthesis 500 in a desired location, the separate helical fasteners 28 are deployed in the manner previously described, to permanently anchor the prosthesis 500 against the vessel wall.

It will be appreciated that the components and/or features of the preferred embodiments described herein may be used together or separately, while the depicted methods and devices may be combined or modified in whole or in part. It is contemplated that the components of the directing device, fastener applier and helical fastener may be alternately oriented relative to each other, for example, offset, bi-axial, etc. Further, it will be understood that the various embodiments may be used in additional procedures not described herein, such as vascular trauma, arterial dissections, artificial heart valve attachment and attachment of other prosthetic device within the vascular system and generally within the body.

The preferred embodiments of the invention are described above in detail for the purpose of setting forth a complete disclosure and for the sake of explanation and clarity. Those skilled in the art will envision other modifications within the scope and sprit of the present disclosure.

We claim:

1. A system comprising:
   at least one tissue-piercing fastener having a sharpened distal tip for piercing and penetrating tissue,
   a fastener attachment assembly sized and configured to be deployed from a remote access site to a targeted endovascular region, the fastener attachment assembly including:
   an intraluminal directing device defining an access lumen and including a deflectable distal region, and
   an intraluminal fastener applier separate from the intraluminal directing device, the intraluminal fastener applier along with the tissue-piercing fastener being sized and configured for introduction through the access lumen, the intraluminal fastener applier including an actuated member that is selectively operable to generate an implantation force in an implantation force direction to implant the tissue-piercing fastener by causing the sharpened distal tip to pierce and penetrate the tissue in the targeted endovascular region, and
   means associated with the fastener attachment assembly for applying a resolving force in a direction different than the implantation force direction within the targeted endovascular region to resolve at least a portion of the implantation force,
   wherein the means includes a stabilizing member carried by the intraluminal directing device and/or the intraluminal fastener applier, wherein the stabilizing member includes a spring-loaded arm adapted for contact with tissue opposite an implantation site of the tissue-piercing fastener.

2. A system according to claim 1 wherein the at least one tissue-piercing fastener comprises a helical fastener, and wherein the actuated member comprises a driven member for implanting a helical fastener.

3. A system according to claim 1 wherein the intraluminal fastener applier includes a catheter body that carries the actuated member, the catheter body having a column strength, and wherein the means includes, at least in part, the column strength of the catheter body.

4. A system according to claim 1 wherein the intraluminal directing device has a column strength, and wherein the means includes, at least in part, the column strength of the intraluminal directing device.

5. The system according to claim 1 wherein the stabilizing member consists of the spring-loaded arm.

6. The system according to claim 1 wherein the stabilizing member is positioned for deployment when an obturator is removed.

7. The system according to claim 6 wherein the intraluminal directing device comprises the obturator.

8. The system according to claim 1 wherein the stabilizing member is distal to an end of the intraluminal directing device.

9. A system comprising:
   at least one tissue-piercing fastener having a sharpened distal tip for piercing and penetrating tissue,
   a fastener attachment assembly sized and configured to be deployed from a remote access site to a targeted endovascular region, the fastener attachment assembly including:
   an intraluminal directing device defining an access path and including a deflectable distal region, and
   an intraluminal fastener applier separate from the intraluminal directing device and being sized and configured for introduction along the access path and including an actuated member that is selectively operable to generate an implantation force in an implantation force direction to implant the tissue-piercing fastener by causing the sharpened distal tip to pierce and penetrate the tissue in the targeted endovascular region, and
   means associated with the fastener attachment assembly for applying a resolving force in a direction different than the implantation force direction within the targeted endovascular region to resolve at least a portion of the implantation force,
   wherein the means includes a stabilizing member carried by the intraluminal directing device,
   wherein the stabilizing member includes an inflatable expandable member adapted for contact with tissue, the inflatable expandable member being spaced apart from an end of the intraluminal directing device.

10. A system comprising:
    at least one tissue-piercing fastener having a sharpened distal tip for piercing and penetrating tissue, a fastener attachment assembly sized and configured to be deployed from a remote access site to a targeted endovascular region, the fastener attachment assembly including:

an intraluminal directing device defining an access path and including a deflectable distal region, and an intraluminal fastener applier separate from the intraluminal directing device and being sized and configured for introduction along the access path and including an actuated member that is selectively operable to generate an implantation force in an implantation force direction to implant the tissue-piercing fastener by causing the sharpened distal tip to pierce and penetrate the tissue in the targeted endovascular region, and means associated with the fastener attachment assembly for applying a resolving force in a direction different than the implantation force direction within the targeted endovascular region to resolve at least a portion of the implantation force, wherein the means includes a stabilizing member carried by the intraluminal directing device and/or the intraluminal fastener applier, wherein the stabilizing member includes a tissue grasping element configured for penetrating into tissue.

11. The system according to claim 10 wherein the tissue grasping element is selected from the group consisting of penetrating needles, hooks, and barbs.

12. The system according to claim 10 wherein the tissue grasping element is configured to pass through a prosthesis and penetrate into the tissue.

* * * * *